(12) United States Patent
Huszar et al.

(10) Patent No.: US 9,713,418 B2
(45) Date of Patent: *Jul. 25, 2017

(54) EXPANDABLE SUPPORT STRUCTURE FOR DELIVERY THROUGH A WORKING CHANNEL

(71) Applicant: Covidien LP, Mansfield, MA (US)

(72) Inventors: Hillary K. Huszar, Redwood City, CA (US); David S. Utley, Redwood City, CA (US); Eric J. Gwerder, Fremont, CA (US); Robert C. Haggerty, Dove Canyon, CA (US); Gilbert Mata, Jr., Tracy, CA (US); Felicia P. Sein-Lwin, San Lorenzo, CA (US)

(73) Assignee: Covidien LP, Mansfield, MA (US)

( * ) Notice: Subject to any disclaimer, the term of this patent is extended or adjusted under 35 U.S.C. 154(b) by 70 days.

This patent is subject to a terminal disclaimer.

(21) Appl. No.: 14/189,865

(22) Filed: Feb. 25, 2014

(65) Prior Publication Data

US 2014/0296846 A1    Oct. 2, 2014

Related U.S. Application Data

(63) Continuation of application No. PCT/US2012/052326, filed on Aug. 24, 2012.
(Continued)

(51) Int. Cl.
*A61B 18/14* (2006.01)
*A61B 1/018* (2006.01)
(Continued)

(52) U.S. Cl.
CPC .......... *A61B 1/018* (2013.01); *A61B 1/00082* (2013.01); *A61B 17/00234* (2013.01);
(Continued)

(58) Field of Classification Search
CPC  A61B 2018/00214; A61B 2018/00577; A61B 2018/1467; A61B 2018/1465;
(Continued)

(56) References Cited

U.S. PATENT DOCUMENTS 5,100,423 A    3/1992  Fearnot
5,228,441 A    7/1993  Lundquist
(Continued)

FOREIGN PATENT DOCUMENTS

EP    0779059 A1    6/1997
EP    2151216 A1    10/2010
(Continued)

OTHER PUBLICATIONS

European Search Report, Application No. EP12826377, dated Sep. 8, 2014.
(Continued)

*Primary Examiner* — Michael Peffley
*Assistant Examiner* — Samantha Good

(57) ABSTRACT

Methods, systems, and devices for providing treatment to a target site are described. The system may include a guide assembly, an expandable support device coupled with the distal end of the guide assembly, and an operative member disposed on the expandable support device. The expandable support device may be configured to transition between a collapsed and expanded configuration. The expandable support device may be supported by one or more flexible supports aligned in parallel with an axis about which the expandable support device collapses and/or multiple splines arranged in a pattern configured to promote transitioning of the expandable support device between an expanded and collapsed configuration. The guide assembly may be configured to provide torque to the expandable support device. The operative member can include multiple electrodes
(Continued)

arranged in parallel to the axis about which the expandable support device collapses.

21 Claims, 53 Drawing Sheets

Related U.S. Application Data

(60) Provisional application No. 61/527,554, filed on Aug. 25, 2011.

(51) Int. Cl.
*A61B 1/00* (2006.01)
*A61M 25/00* (2006.01)
*B25J 18/06* (2006.01)
*A61B 17/00* (2006.01)
*A61B 18/00* (2006.01)

(52) U.S. Cl.
CPC ..... *A61B 18/1492* (2013.01); *A61M 25/0074* (2013.01); *B25J 18/06* (2013.01); *A61B 2017/00238* (2013.01); *A61B 2018/0016* (2013.01); *A61B 2018/00214* (2013.01); *A61B 2018/00577* (2013.01); *A61B 2018/1465* (2013.01); *A61B 2018/1467* (2013.01); *A61B 2018/1475* (2013.01); *A61M 25/008* (2013.01); *A61M 25/0082* (2013.01); *Y10T 74/20311* (2015.01)

(58) Field of Classification Search
CPC ............ A61B 2018/1475; A61B 1/018; A61B 1/00082; A61B 18/1492; A61B 17/00234; A61B 2017/00238; A61M 25/0074; A61M 25/008; A61M 25/0082; B25J 18/06
See application file for complete search history.

(56) References Cited

U.S. PATENT DOCUMENTS

| | | | |
|---|---|---|---|
| 5,322,064 A | 6/1994 | Lundquist |
| 5,327,905 A | 7/1994 | Avitall |
| 5,329,923 A | 7/1994 | Lunkquist |
| 5,374,261 A | 12/1994 | Yoon |
| 5,375,594 A | 12/1994 | Cueva |
| 5,377,682 A | 1/1995 | Ueno et al. |
| 5,391,200 A | 2/1995 | KenKnight et al. |
| 5,413,107 A | 5/1995 | Oakley et al. |
| 5,575,772 A | 11/1996 | Lennox |
| 5,672,153 A | 9/1997 | Lax et al. |
| 5,681,345 A | 10/1997 | Euteneuer |
| 5,720,743 A | 2/1998 | Bischof et al. |
| 5,722,401 A | 3/1998 | Pietroski et al. |
| 5,810,803 A | 9/1998 | Moss et al. |
| 5,846,196 A | 12/1998 | Siekmeyer et al. |
| 5,876,399 A | 3/1999 | Chia et al. |
| 5,881,727 A | 3/1999 | Edwards |
| 5,891,137 A | 4/1999 | Chia et al. |
| 5,902,328 A | 5/1999 | LaFontaine et al. |
| 5,916,235 A | 6/1999 | Guglielmi |
| 5,944,738 A | 8/1999 | Amplatz et al. |
| 5,997,534 A | 12/1999 | Tu et al. |
| 6,012,457 A | 1/2000 | Lesh |
| 6,023,638 A | 2/2000 | Swanson |
| 6,036,689 A | 3/2000 | Tu |
| 6,063,080 A | 5/2000 | Nelson et al. |
| 6,063,082 A | 5/2000 | DeVore et al. |
| 6,068,629 A | 5/2000 | Haissaguerre et al. |
| 6,071,279 A | 6/2000 | Whayne et al. |
| 6,071,280 A | 6/2000 | Edwards et al. |
| 6,074,398 A | 6/2000 | Leschinsky |
| 6,102,886 A | 8/2000 | Lundquist et al. |
| 6,149,647 A | 11/2000 | Tu et al. |
| 6,152,920 A | 11/2000 | Thompson et al. |
| 6,168,592 B1 | 1/2001 | Kupiecki et al. |
| 6,241,754 B1 | 6/2001 | Swanson et al. |
| 6,254,598 B1 | 7/2001 | Edwards et al. |
| 6,254,599 B1 | 7/2001 | Lesh et al. |
| 6,264,664 B1 | 7/2001 | Avellanet |
| 6,267,781 B1 | 7/2001 | Tu |
| 6,290,697 B1 | 9/2001 | Tu et al. |
| 6,292,702 B1 | 9/2001 | King et al. |
| 6,319,251 B1 | 11/2001 | Tu et al. |
| 6,363,937 B1 | 4/2002 | Hovda et al. |
| 6,375,654 B1 | 4/2002 | McIntyre |
| 6,415,187 B1 | 7/2002 | Kuzma et al. |
| 6,428,536 B2 | 8/2002 | Panescu et al. |
| 6,430,426 B2 | 8/2002 | Avitall |
| 6,432,104 B1 | 8/2002 | Durgin et al. |
| 6,442,435 B2 | 8/2002 | King et al. |
| 6,471,659 B2 | 10/2002 | Eggers et al. |
| 6,488,678 B2 | 12/2002 | Sherman |
| 6,514,246 B1 | 2/2003 | Swanson et al. |
| 6,522,932 B1 | 2/2003 | Kuzma et al. |
| 6,527,769 B2 | 3/2003 | Langberg et al. |
| 6,544,262 B2 | 4/2003 | Fleischman |
| 6,551,310 B1 | 4/2003 | Ganz et al. |
| 6,562,034 B2 | 5/2003 | Edwards et al. |
| 6,572,612 B2 | 6/2003 | Stewart et al. |
| 6,579,297 B2 | 6/2003 | Bicek et al. |
| 6,589,265 B1 | 7/2003 | Palmer et al. |
| 6,638,278 B2 | 10/2003 | Falwell et al. |
| 6,659,981 B2 | 12/2003 | Stewart et al. |
| 6,663,626 B2 | 12/2003 | Truckai et al. |
| 6,669,691 B1 | 12/2003 | Taimisto |
| 6,671,533 B2 | 12/2003 | Chen et al. |
| 6,702,843 B1 | 3/2004 | Brown et al. |
| 6,730,082 B2 | 5/2004 | Messing et al. |
| 6,738,673 B2 | 5/2004 | Desai |
| 6,740,082 B2 | 5/2004 | Shadduck |
| 6,740,083 B2 | 5/2004 | Messing et al. |
| 6,780,196 B2 | 8/2004 | Chin et al. |
| 6,805,131 B2 | 10/2004 | Kordis |
| 6,813,520 B2 | 11/2004 | Sampson et al. |
| 6,837,886 B2 | 1/2005 | Collins et al. |
| 6,852,091 B2 | 2/2005 | Edwards et al. |
| 6,866,662 B2 | 3/2005 | Fuimaono et al. |
| 6,887,236 B2 | 5/2005 | Gilboa |
| 6,893,438 B2 | 5/2005 | Hall et al. |
| 6,893,440 B2 | 5/2005 | Durgin et al. |
| 6,923,801 B2 | 8/2005 | Kurtzer et al. |
| 6,958,064 B2 | 10/2005 | Rioux et al. |
| 6,960,206 B2 | 11/2005 | Keane |
| 6,974,455 B2 | 12/2005 | Garabedian et al. |
| 6,986,769 B2 | 1/2006 | Nelson et al. |
| 6,997,925 B2 | 2/2006 | Maguire et al. |
| 7,004,938 B2 | 2/2006 | Ormsby et al. |
| 7,013,170 B2 | 3/2006 | Bowe |
| 7,025,768 B2 | 4/2006 | Elliott |
| 7,048,734 B1 | 5/2006 | Fleischman et al. |
| 7,074,178 B2 | 7/2006 | Connors et al. |
| 7,077,841 B2 | 7/2006 | Gaiser et al. |
| 7,097,643 B2 | 8/2006 | Cornelius et al. |
| 7,192,430 B2 | 3/2007 | Truckai et al. |
| 7,198,636 B2 | 4/2007 | Cully et al. |
| 7,229,438 B2 | 6/2007 | Young |
| 7,241,295 B2 | 7/2007 | Maguire |
| 7,285,117 B2 | 10/2007 | Krueger et al. |
| 7,285,120 B2 | 10/2007 | Im et al. |
| 7,301,131 B2 | 11/2007 | Gauthier et al. |
| 7,416,534 B2 | 8/2008 | Nair et al. |
| 7,416,549 B2 | 8/2008 | Young et al. |
| 7,474,909 B2 | 1/2009 | Phan et al. |
| 7,615,049 B2 | 11/2009 | West et al. |
| 7,670,337 B2 | 3/2010 | Young |
| 7,680,543 B2 | 3/2010 | Azure |
| 7,722,604 B2 | 5/2010 | Brown, III et al. |
| 7,774,039 B2 | 8/2010 | Koblish |
| 7,780,646 B2 | 8/2010 | Farnholtz |
| 7,844,319 B2 | 11/2010 | Susil et al. |
| 7,850,685 B2 | 12/2010 | Kunis et al. |

(56) References Cited

U.S. PATENT DOCUMENTS

| | | |
|---|---|---|
| 7,959,627 B2 | 6/2011 | Utley et al. |
| 7,970,480 B2 | 6/2011 | Swanson |
| 8,043,326 B2 | 10/2011 | Hancock et al. |
| 8,048,072 B2 | 11/2011 | Verin et al. |
| 8,052,679 B2 | 11/2011 | Young |
| 8,152,805 B2 | 4/2012 | Young |
| 8,172,838 B2 | 5/2012 | Schnitzler |
| 8,177,711 B2 | 5/2012 | Butler |
| 8,177,833 B2 | 5/2012 | Chuter et al. |
| 8,181,995 B2 | 5/2012 | DeCarlo |
| 8,192,426 B2 | 6/2012 | Stern et al. |
| 8,224,416 B2 | 7/2012 | de la Rama et al. |
| 8,229,538 B2 | 7/2012 | Koblish |
| 8,231,621 B2 | 7/2012 | Hutchins et al. |
| 8,235,983 B2 | 8/2012 | Webster et al. |
| 8,235,988 B2 | 8/2012 | Davis et al. |
| 8,241,280 B2 | 8/2012 | Bales et al. |
| 8,246,671 B2 | 8/2012 | Khairkhahan |
| 8,249,685 B2 | 8/2012 | Falwell et al. |
| 8,251,986 B2 | 8/2012 | Chornenky et al. |
| 8,260,394 B2 | 9/2012 | Anderson et al. |
| 8,273,084 B2 | 9/2012 | Kunis et al. |
| 8,273,101 B2 | 9/2012 | Garcia et al. |
| 8,287,531 B2 | 10/2012 | Mest |
| 8,287,532 B2 | 10/2012 | Carroll et al. |
| 8,290,582 B2 | 10/2012 | Lin et al. |
| 8,295,902 B2 | 10/2012 | Salahieh et al. |
| 2002/0128546 A1 | 9/2002 | Silver |
| 2004/0002747 A1 | 1/2004 | Ryan et al. |
| 2004/0215296 A1 | 10/2004 | Ganz |
| 2004/0243124 A1 | 12/2004 | Im et al. |
| 2005/0154435 A1 | 7/2005 | Stern et al. |
| 2005/0203602 A1 | 9/2005 | Wallace et al. |
| 2006/0253183 A1 | 11/2006 | Thagalingam |
| 2007/0066973 A1 | 3/2007 | Stern et al. |
| 2007/0142831 A1 | 6/2007 | Shadduck |
| 2007/0156130 A1 | 7/2007 | Thistle |
| 2007/0287994 A1 | 12/2007 | Patel |
| 2007/0299435 A1 | 12/2007 | Crowe |
| 2007/0299438 A1 | 12/2007 | Holzbaur |
| 2008/0009927 A1 | 1/2008 | Vilims |
| 2008/0125775 A1 | 5/2008 | Morris |
| 2009/0012513 A1 | 1/2009 | Utley et al. |
| 2009/0131930 A1* | 5/2009 | Gelbart ............. A61B 18/1492 606/41 |
| 2009/0182325 A1 | 7/2009 | Werneth et al. |
| 2009/0216221 A1* | 8/2009 | Davis ............... A61B 18/1492 606/33 |
| 2010/0137860 A1 | 6/2010 | Demarais et al. |
| 2010/0191235 A1 | 7/2010 | Moshe et al. |
| 2011/0054465 A1 | 3/2011 | Werneth et al. |
| 2012/0029354 A1 | 2/2012 | Mark et al. |
| 2012/0059366 A1 | 3/2012 | Drews et al. |
| 2012/0071870 A1 | 3/2012 | Salahieh et al. |
| 2012/0101495 A1 | 4/2012 | Young et al. |
| 2012/0101499 A1 | 4/2012 | Lagodzki |
| 2012/0116378 A1 | 5/2012 | Toth et al. |
| 2012/0209262 A1 | 8/2012 | Falwell et al. |
| 2012/0265186 A1 | 10/2012 | Burger et al. |
| 2012/0265198 A1 | 10/2012 | Crow et al. |
| 2012/0271301 A1 | 10/2012 | Fischell et al. |
| 2013/0338467 A1 | 12/2013 | Grasse et al. |
| 2014/0336640 A1 | 11/2014 | Beeckler et al. |

FOREIGN PATENT DOCUMENTS

| | | |
|---|---|---|
| EP | 2308540 A1 | 4/2011 |
| JP | H08511438 | 12/1996 |
| JP | 2000140118 A | 5/2000 |
| JP | 2002095677 A | 4/2002 |
| JP | 2010532702 A | 10/2010 |
| JP | 2014524789 A | 9/2014 |
| WO | 9613297 | 5/1996 |
| WO | 2005/070061 A2 | 4/2005 |
| WO | 2006009856 A1 | 1/2006 |

OTHER PUBLICATIONS

European Search Report, Application No. EP14162338, dated Sep. 10, 2014.
European Search Report, Application No. EP14162347, dated Sep. 22, 2014.
European Search Report, Application No. EP14162339, dated Sep. 12, 2014.
European Search Report, Application No. EP14162341, dated Sep. 15, 2014.
Communication pursuant to Article 94(3) EPC for Application No. 14162339.7 dated Jul. 15, 2015 for Applicant Covidien LP from the European Patent Office.
Communication pursuant to Article 94(3) EPC for Application No. 12826377.9 dated Jul. 16, 2015 for Application Covidien LP from the European Patent Office.
Communication pursuant to Article 94(3) EPC for Application No. 14162338.9 dated Jul. 14, 2015 for Applicant Covidien LP from the European Patent Office.
Examiner's Report for EP App. No. 14162347.0 dated Feb. 18, 2016 from the European Patent Office.
Examiner's Report for EP App. No. 14162338.9 dated Feb. 16, 2016 from the European Patent Office.
Chinese Application No. 201280049538.0 Office Action dated Dec. 9, 2015 from the Chinese Patent Office.
Memo Concerning the Official Action, translation of the requirements stated by the Examiner for Mexican Patent Appln. No. MX/A/2010/000168.
Patent Examination Report No. 2 from the Australian Government IP Australia, for Patent Application No. 2015203849, dated Aug. 16, 2016.
European Patent Office, Office Action for Application No. 14162339.7 dated Feb. 23, 2016.
Australian Government IP Australia Patent Examination Report No. 1 for Application No. 2015203849 dated Apr. 4, 2016.
European Patent Office, Office Action for Application No. 14162341.3 dated Feb. 23, 2016.
Notice of Reasons for Rejection for Japanese Patent Application No. 2015-119225, dated Jun. 23, 2016.
Examination Report dated Feb. 7, 2017, for EP 08781394.5 from the European Patent Office.
Examiner's Report for Canadian Application No. 2,692,669 dated Dec. 22, 2016, from the Canadian Intellectual Property Office.

* cited by examiner

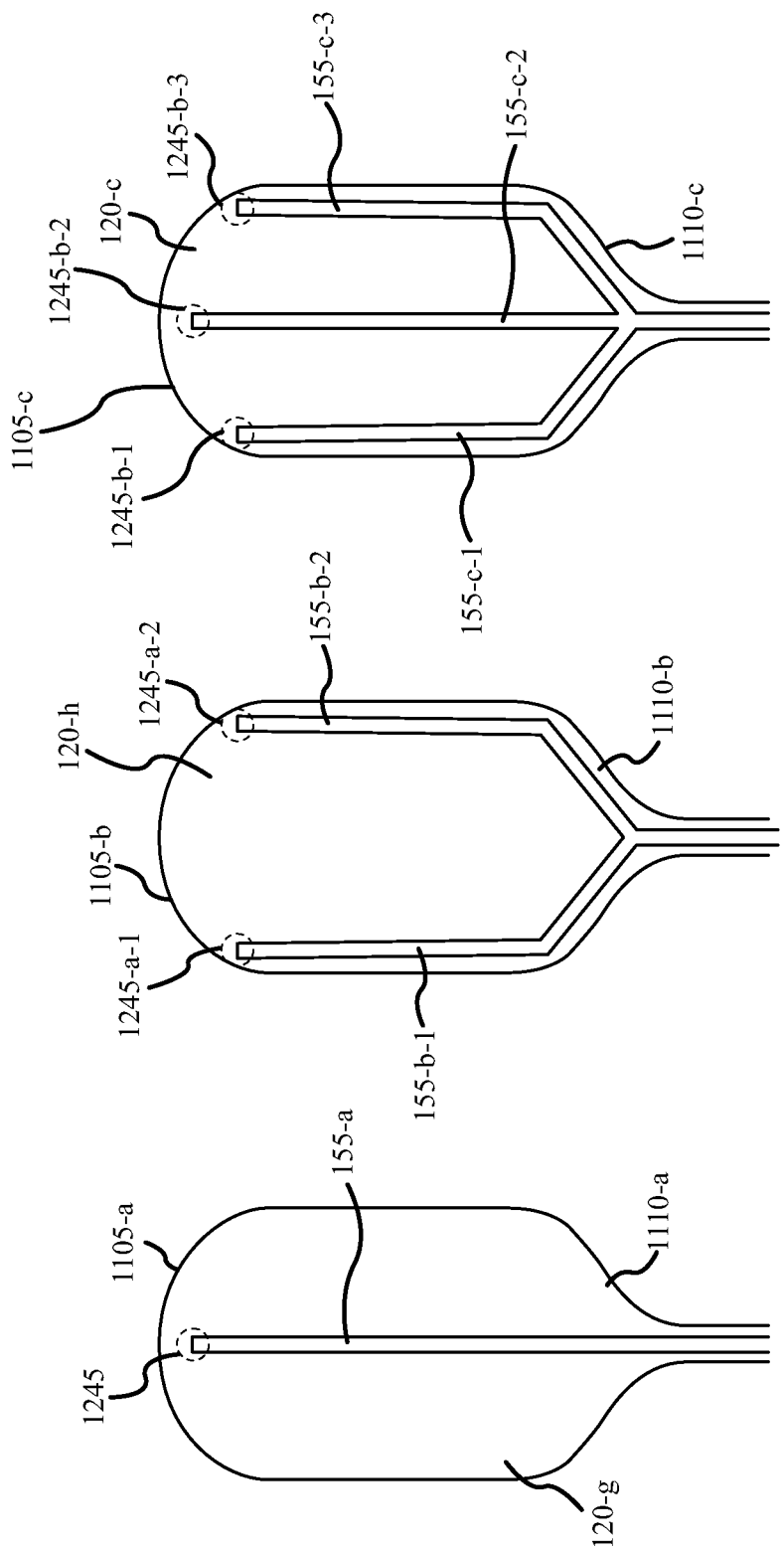

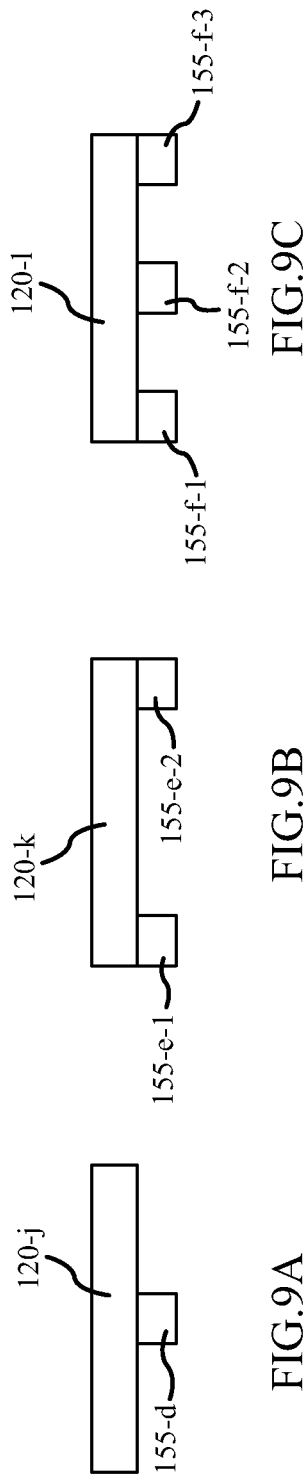
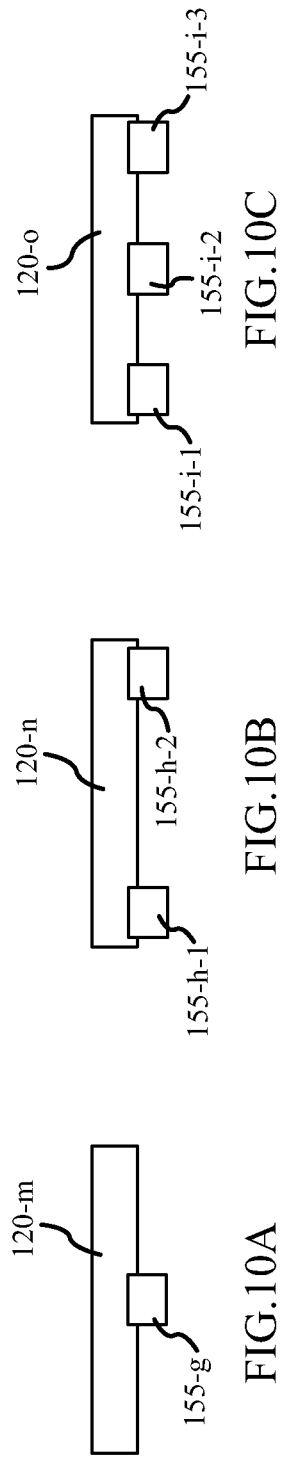

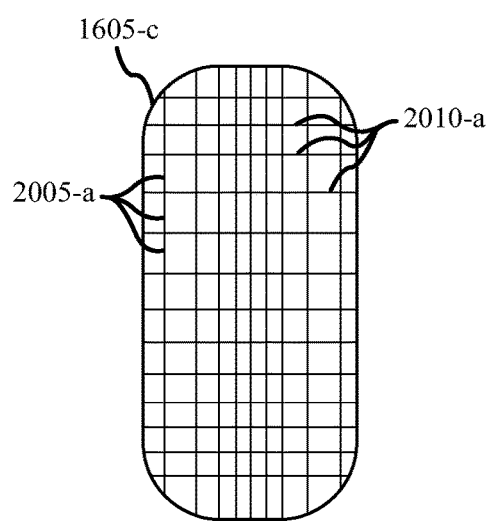
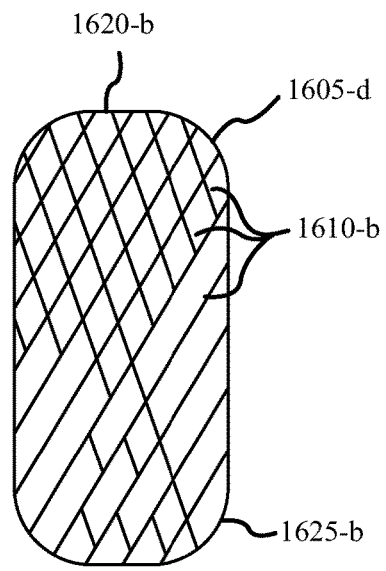
FIG.13A  FIG.13B
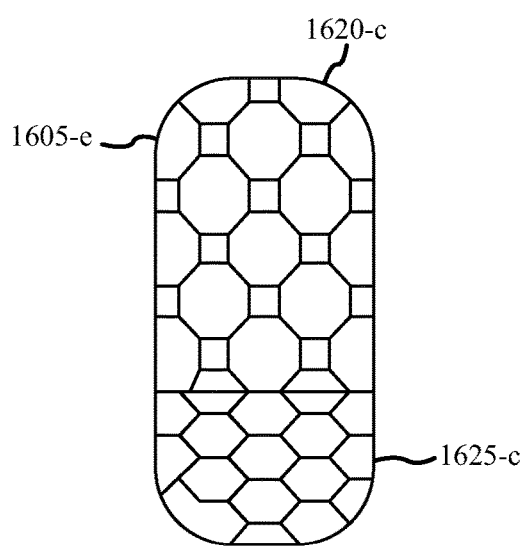
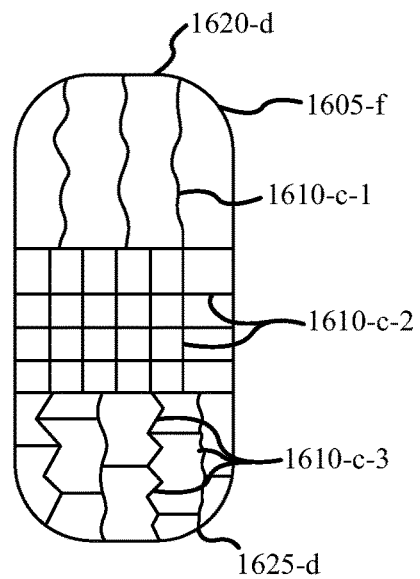
FIG.13C  FIG.13D

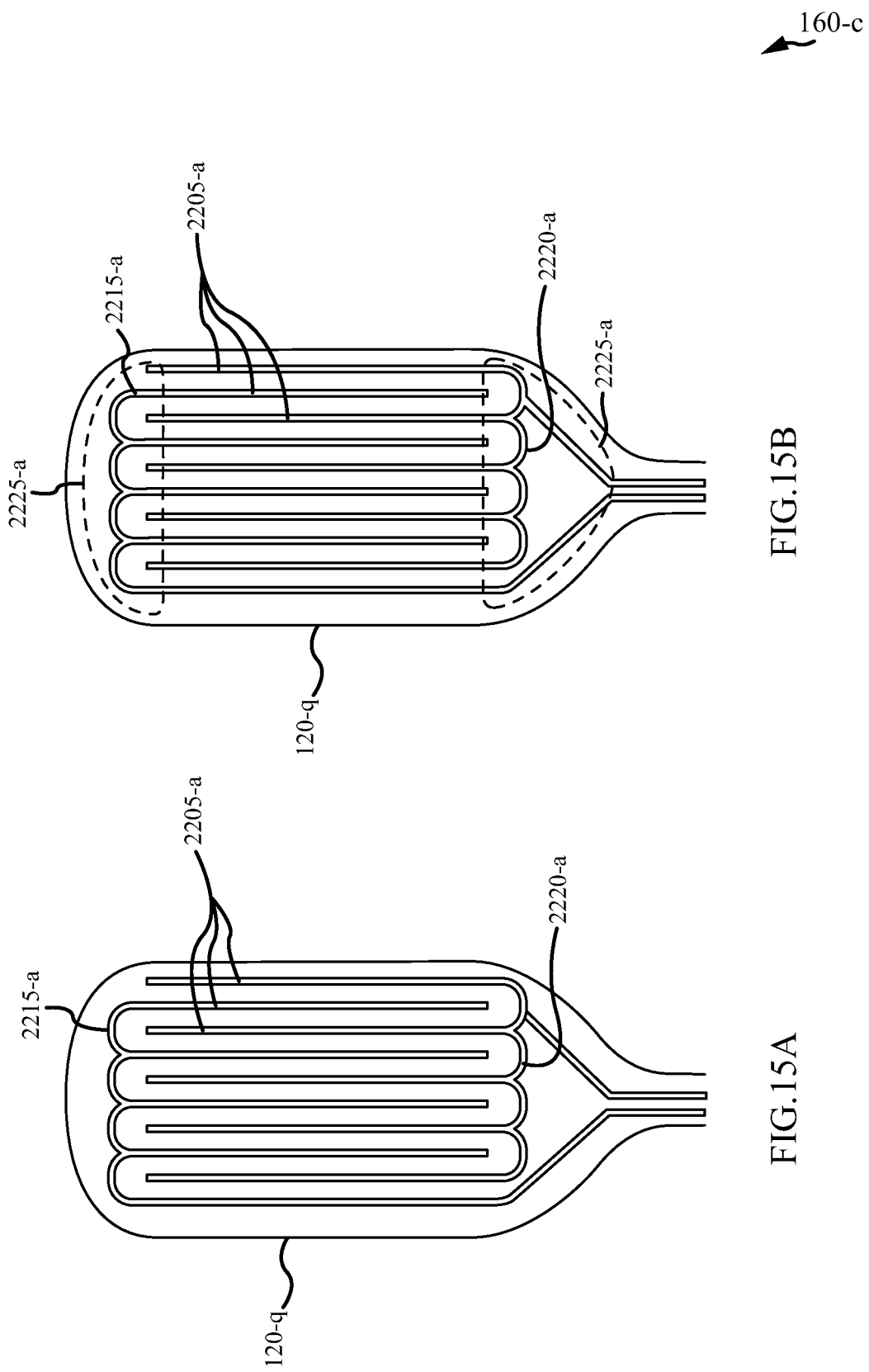

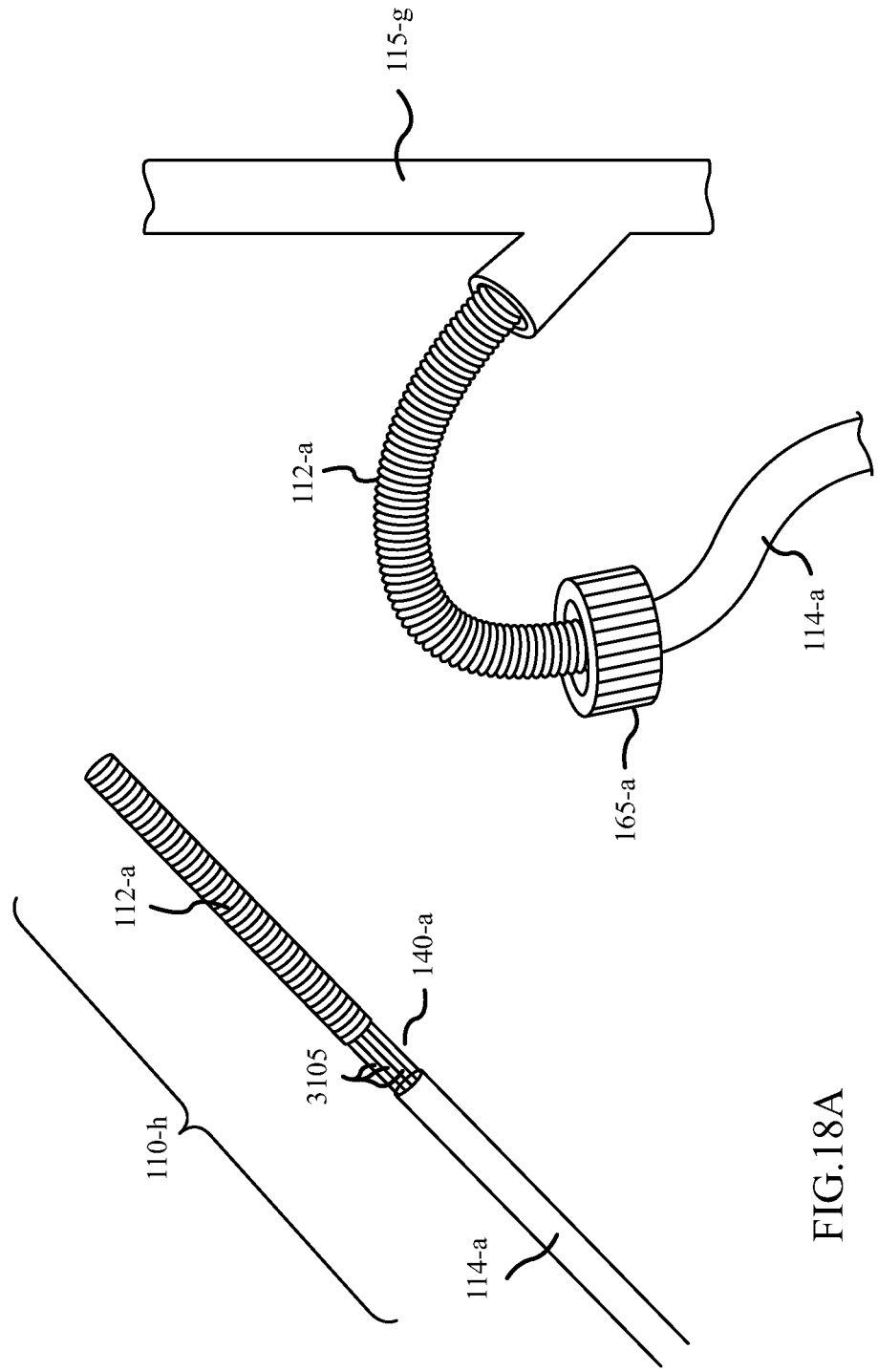

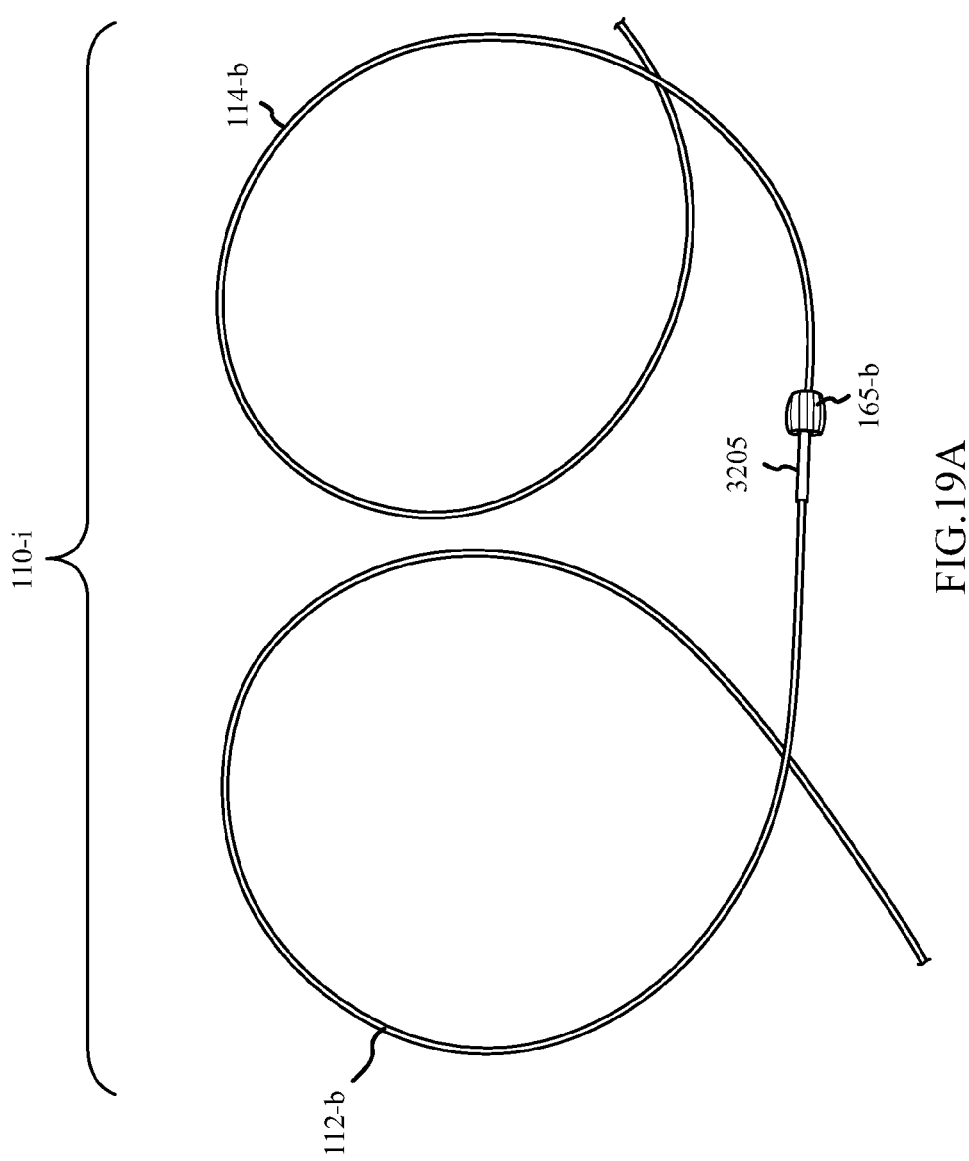

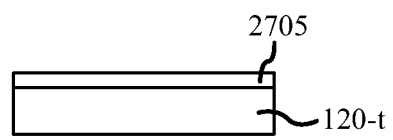
FIG.27A          FIG.27B
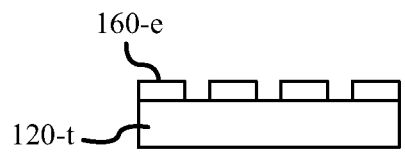
FIG.27C
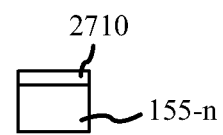
FIG.27D          FIG.27E
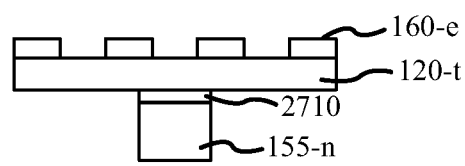
FIG.27F

EXPANDABLE SUPPORT STRUCTURE FOR DELIVERY THROUGH A WORKING CHANNEL

CROSS REFERENCES

This application is a continuation of PCT/US2012/052326, filed Aug. 24, 2012, entitled, "SYSTEMS, DEVICES, AND METHODS FOR TREATMENT OF LUMINAL TISSUE," which claims priority to U.S. provisional patent application No. 61/527,554, titled "DEVICES AND METHODS FOR TREATMENT OF LUMINAL TISSUE," filed Aug. 25, 2011, each of which are incorporated by reference in their entirety for all purposes. This application is also related to U.S. patent application Ser. No. 14/240,970, filed Feb. 25, 2014, entitled "EXPANDABLE SUPPORT STRUCTURE AND OPERATIVE ELEMENT FOR DELIVERY THROUGH A WORKING CHANNEL;" U.S. patent application Ser. No. 14/189,855, filed Feb. 25, 2014, entitled, "TRANSMITTING TORQUE TO AN OPERATIVE ELEMENT THROUGH A WORKING CHANNEL;" U.S. patent application Ser. No. 14/189,858, filed Feb. 25, 2014, entitled "TRANSMITTING TORQUE WITH A HANDLE TO AN OPERATIVE ELEMENT THROUGH A WORKING CHANNEL;" U.S. patent application Ser. No. 14/189,862, filed Feb. 25, 2014, entitled, "FLEXIBLE CIRCUIT FOR DELIVERY THROUGH A WORKING CHANNEL;" and U.S. patent application Ser. No. 14/189,867, filed Feb. 25, 2014, entitled, "EXPANDABLE SUPPORT STRUCTURE FOR DELIVERY THROUGH A WORKING CHANNEL," each of which are incorporated by reference in their entirety for all purposes.

BACKGROUND

Various devices and techniques exist for providing therapy in the body. A common approach to administering treatment or performing diagnostics at a tissue site in the body involves delivering an instrument to the site at a distal end of an elongate catheter or endoscope. A problem exists, however, in that many instruments and devices do not fit within the catheter or endoscope. Currently, some devices may be limited in use because the treatment surface of the device is too large for delivery to the site through a catheter or endoscope.

The delivery of many existing devices to a treatment site through the use of a catheter or endoscope can also be hindered by the location of the treatment site within the body. In some cases, for example, the device needs to be able to navigate a tortuous path or small diameter body lumens to reach a treatment site. Some known devices lack the ability to bend along tortuous delivery paths Another problem may exist with treating a target site significantly larger than the delivery pathway through which the device must pass. In order to treat a large target site, a device with a large treatment surface is often desired. However, if the treatment surface is too large, it may not be possible to deliver the device through narrow lumens. If the treatment surface is reduced to fit within the catheter or endoscope, it may provide too small a surface area for efficient and efficacious delivery of treatment to the relatively large target site.

There may thus be a need for systems, devices and methods that may overcome the above and/or other disadvantages of known systems and methods.

SUMMARY

Methods, systems, and devices are described for providing treatment to a target site, such as a site within a body lumen. Systems may include an expandable support device that may be coupled with a distal end of a guide assembly. An operative member may be disposed on the expandable support device such that moving the expandable support device to the target site using the guide assembly delivers the operative member to the target site. The guide assembly may be utilized to transmit torque and/or to rotate to the expandable support device and/or the operative member.

The expandable support member may include a solid body of elastomeric material. The elastomeric material may be flexible so that it may transition between a folded, or collapsed configuration and a planar, or expanded, configuration. One or more flexible supports may be coupled with the elastomeric body such that the flexible supports are each aligned parallel to a central axis of the elastomeric body. The flexible supports may be made from at least a highly elastic, such as spring steel, or a superelastic material, such as nitinol, and may be arranged in a single central axis configuration, a wishbone configuration, or a trident configuration.

The expandable support member may include a solid support member made from at least a highly elastic or superelastic material that is supported by multiple splines located within the perimeter of the solid support member. The multiple splines may be separated by voids so as to create a pattern of splines having a width and spacing that promotes transitioning of the solid support member between a collapsed configuration and an expanded configuration. The splines may be arranged in a pattern wherein a spline arranged to substantially overlap a central axis of the solid support member has splines extending away from the central spline in both directions towards a distal end of the solid support member.

The operative member may include a flexible circuit capable of bending with the expandable support device upon which it is disposed. The flexible circuit may include multiple electrodes aligned in parallel to one another. The electrodes may also be aligned in parallel to an axis about which the flexible circuit collapses from a planar configuration to a folded configuration so that the electrodes do not substantially impede the transition between an expanded configuration and a collapsed configuration. The flexible circuit may include a first bus at one end of the parallel electrodes and a second bus at the opposite end of the electrodes. The electrodes may be coupled with the first and second bus in an alternating pattern.

The guide assembly that may be used to move the expandable support device may include a first shaft portion and a second shaft portion separated by a break. Transmission lines may extend through both the first shaft and the second shaft. The break between the first shaft and the second shaft may allow the first shaft to rotate independently of the second shaft. The first shaft may be configured such that rotation of the first shaft transmits torque and/or rotation to the expandable support device.

In some embodiments, an expandable support device may be configured for delivering an operative member through a working channel to a target treatment area. The expandable support device may include an elastomeric body that is configured to support the operative member and promote expansion of the expandable support device between a collapsed configuration and an expanded configuration. The elastomeric body may include a proximal portion that is configured for coupling the elastomeric body with a guide assembly, a distal portion that is opposite the proximal portion, and a central axis that extends between the distal portion and the proximal portion of the elastomeric body.

The expandable support device may also include one or more supports that are coupled with the elastomeric body. The one or more supports may be aligned parallel to the central axis of the elastomeric body. At least one of the supports may include at least a highly elastic or superelastic material.

The expandable support device may include two supports that are arranged in a wishbone configuration. The expandable support may include three supports that are arranged in a trident configuration. The expandable support device may have a single support that extends along at least a portion of the central axis of the elastomeric body. The expandable support device may have one or more supports that are configured as at least linear supports or longitudinal supports. The expandable support device may include supports that are made from a superelastic material. The superelastic material may include nitinol. The expandable support may include supports that are made from highly elastic material. The highly elastic material may include spring steel. One or more of the supports coupled with the elastomeric body may include polyimide One or more of the supports including polyimide may be disposed at a periphery of the elastomeric body.

The expandable support device may also include an operative member disposed on the elastomeric body. The operative member disposed on the elastomeric body may be an ablation device. The expandable support device may also include protective padding that encompasses the distal end of each of the supports. The protective padding may include silicone.

The proximal portion of the elastomeric body may be tapered in a direction away from the distal end of the elastomeric support. The elastomeric body may also be configured to facilitate movement of the expandable support device into the working channel. The elastomeric body may include silicone. The elastomeric body may be transparent. The elastomeric body may be a molded elastomeric body. The working channel may include at least a portion of an endoscope or a catheter. The supports may be coupled with the elastomeric body using a silicone adhesive. One side of the proximal portion of the elastomeric body may include a marking or a texturing. The marking or texturing may facilitate identifying on which side of the elastomeric body the operative member is positioned.

Some embodiments include a system for delivering treatment to a target treatment that may include an expandable support device. The expandable support device may be configured for delivering an operative member through a working channel to a target treatment area. The expandable support device may include an elastomeric body, one or more supports coupled with the elastomeric body, and an operative member disposed on the elastomeric body. The elastomeric body may be configured to support an operative member and promote expansion of the expandable support device between a collapsed configuration and an expanded configuration. The elastomeric body may include a proximal portion configured for coupling the elastomeric body with a guide assembly, a distal portion opposite the proximal portion, and a central axis extending between the distal portion and the proximal portion of the elastomeric body. The one or more supports coupled with the elastomeric body may be aligned parallel to the central axis of the elastomeric body. At least one of the supports may include at least a highly elastic or superelastic material.

The system may also include a guide assembly. The guide assembly may include a guide shaft and a coupling mechanism that is configured to couple the expandable support device to the guide shaft. The system may also include a working channel. The working channel may be configured to receive the expandable support device and the guide assembly. The operative member of the system may include an ablation device. The working channel of the system may include at least a portion of an endoscope or a catheter.

Some embodiments include a method of delivering an expandable support device to a target treatment area that may a step of providing an expandable support device configured for delivering an operative member through a working channel to a target treatment area. The method may also include a step of inserting the expandable support device into a first end of the working channel and a step of moving the expandable support device through the working channel until the expandable support device passes out of a second end of the working channel. The expandable support device may include an elastomeric body and one or more supports coupled with the elastomeric body. The elastomeric body may be configured to support an operative member and promote expansion of the expandable support device between a collapsed configuration and an expanded configuration. The elastomeric body may include a proximal portion configured for coupling the elastomeric body with a guide assembly, a distal portion opposite the proximal portion, and a central axis extending between the distal portion and the proximal portion of the elastomeric body. The one or more supports may be aligned parallel to the central axis of the elastomeric body. At least one of the supports may include at least a highly elastic or superelastic material. The method may also include positioning the expandable support device into a collapsed position prior to inserting the expandable support device into the working channel.

Some embodiments include a guide assembly for delivering and positioning an operative member through a working channel to a target treatment area that may include one or more transmission lines, a first shaft enclosing at least a first portion of the one or more transmission lines, and a second shaft enclosing at least a second portion of the transmission lines. The transmission lines may operatively connect the operative member to a power source. The first shaft may be configured for transmitting torque to the operative member. The first shaft and the second shaft may be configured to allow the first shaft to rotate independently of the second shaft.

The first shaft may include a flexible shaft. The flexible shaft may include stainless steel. The flexible shaft may include two or more layers, with each layer including two or more stainless steel wires wound around a common axis. The flexible shaft may be configured to couple with an expandable support device configured to deliver the operative member through a working channel to a target treatment area.

The one or more transmission lines may be coupled with the first shaft at a distal end of the first shaft and decoupled from the first shaft at a proximal end of the first shaft. The guide assembly may also include a protection element. The protection element may be coupled with the first shaft and extend over a portion of the second shaft. The guide assembly may also include a control element. The control element may be coupled with the first shaft and configured to transmit rotational motion to the first shaft. The control element may be coupled with the first shaft for approximately one to one rotational movement between the control element and the first shaft. The control element may be coupled with the first shaft by a crimp tube fixed at one end of the control. A control element and a protection element may be integrated with each other as one element in some cases.

The first shaft may include a rigid section at the proximal end of the first shaft. The rigid section of the first shaft may be configured to be inserted into the working channel. The rigid section of the first shaft may have a length of at least 2 cm in some embodiments. The first shaft may also include a flexible section that is positioned between the rigid section and the operative member. The second shaft may be coupled with the power source. The second shaft may also be rotationally fixed relative to the power source. The one or more transmission lines may include electrical wires. The first shaft and the second shaft may be configured to axially move the operative member. The first shaft may be configured to axially move the operative member. The first shaft may be located between the operative member and the second shaft. The second shaft may be located between the first shaft and the power source.

The guide assembly may also include a handle that is coupled with the first shaft. The guide assembly may also include an introducer. The introducer may include a conical section, a cylindrical section, and a channel extending through the conical section and the cylindrical section. The first shaft may extend through the channel. The cylindrical section may be configured to insert into the working channel. The guide assembly may include a docking member. The docking member may include a first end, a second end, and a channel extending through the docking member. The first end of the docking member may be configured to couple with the introducer. The docking member may be configured at least to couple with or be integrated with at least a control element or a protection element.

Some embodiments include a system for delivering treatment to a target treatment that may include a guide assembly, an expandable support device, and an operative member. The guide assembly may be provided for delivering and positioning the operative member through a working channel to a target treatment area. The guide assembly may include one or more transmission lines, a first shaft enclosing at least a first portion of the one or more transmission lines, a second shaft enclosing at least a second portion of the transmission lines. The transmission lines may operatively connect the operative member to a power source. The first shaft may be configured for transmitting torque to the operative member. The first shaft and the second shaft may be configured to allow the first shaft to rotate independently of the second shaft. The expandable support device may be configured to deliver the operative member through the working channel to the target treatment area. The expandable support device may be coupled with a distal end of the guide assembly. The operative member may be coupled with the expandable support device.

The expandable support device of the system may include an elastomeric body configured to support the operative member. The elastomeric body may include a proximal portion configured for coupling the elastomeric body with the guide assembly, a distal portion opposite the proximal portion, and a central axis extending between the distal portion and the proximal portion.

The system may also include one or more supports coupled with the elastomeric body and aligned parallel to the central axis of the elastomeric body. At least one of the supports may include at least a highly elastic or superelastic material. The operative member of the system may be coupled with the transmission lines.

Some embodiments include a method of utilizing a guide assembly for delivering an operative member to a target treatment that may include a step of providing a system. The system may include a guide assembly for delivering and positioning the operative member through a working channel to the target treatment area, an expandable support device configured to deliver the operative member through the working channel to the target treatment area and coupled with a distal end of the guide assembly, and an operative member coupled with the expandable support device. The guide assembly may include one or more transmission lines for operatively connecting the operative member to a power source, a first shaft enclosing at least a first portion of the one or more transmission lines, and a second shaft enclosing at least a second portion of the transmission lines. The first shaft may be configured for transmitting torque to the operative member. The first shaft and the second shaft may be configured to allow the first shaft to rotate independently of the second shaft. The method may also include a step of inserting the expandable support device into a first end of the working channel, and a step of moving the expandable support device through the working channel utilizing the guide assembly until the expandable support device passes out of a second end of the working channel.

The method may also include a step of positioning the expandable support device into a collapsed position prior to inserting the expandable support device into the working channel. The method may also include a step of rotating the first shaft to provide torque to the operative member.

Some embodiments include a guide assembly configured for positioning an operative member through a working channel and to a target treatment area that may include one or more transmission lines for operatively connecting the operative member to a power source. The guide assembly may also include a flexible shaft enclosing at least a portion of the one or more power transmission lines. The flexible shaft may be configured for transmitting torque to the operative member. The guide assembly may also include a handle element. The handle element may include a body and a channel extending through the body. The flexible shaft may pass through the channel and the handle element may be configured such that the flexible shaft may move through the channel.

The guide assembly may also include a rigid shaft coupled with a first end of the handle element. The rigid shaft may be configured such that the flexible shaft may move through the rigid shaft. The rigid shaft may have a length of at least 2 cm in some embodiments. The rigid section may be configured to be inserted into the working channel.

The guide assembly may also include a power source side shaft. The power source side shaft may be configured to allow the flexible shaft to rotate independently of the power source side shaft. The power source side shaft may be located between the flexible shaft and the power source. The handle element may extend over a portion of the power source side shaft. The flexible shaft may include two or more layers. Each layer may include two or more stainless steel wires wound around a common axis. The flexible shaft may be configured to couple with an expandable support device configured to deliver the operative member through a working channel to a target treatment area. The power source side shaft may be coupled with the power source. The power source side shaft may also be rotationally fixed relative to the power source. The one or more transmission lines may include electrical wires.

The guide assembly may also include a locking mechanism that is coupled with the handle element. The locking mechanism may be secured to the flexible shaft inside the channel of the handle. The locking mechanism may be configured to move along an axis of the handle element to adjust a length of the flexible shaft extending out of the handle element. The locking mechanism may move along the axis of the handle element when in an unlocked position and may be fixed to the handle element when in a locked position. The handle element may be configured to slide along the flexible shaft and the locking mechanism may be configured to lock the handle element at a position along the flexible shaft.

The guide assembly may also include a protection element coupled with the flexible shaft. The protection element may extend over a portion of the second shaft. The protection element may be coupled with the flexible shaft at a position between the handle element and the power source side shaft. The flexible shaft and the power source side shaft may be configured to axially move the operative member.

Some embodiments include a method of delivering an operative member to a target treatment area that may include a step of providing a system. The system may include a guide assembly. The guide assembly may include one or more transmission lines for operatively connecting an operative member to a power source, a flexible shaft enclosing at least a portion of the one or more power transmission lines, and a handle element. The flexible shaft may be configured for transmitting torque to the operative member. The handle element may include a body and a channel extending through the body. The flexible shaft may pass through the channel. The handle element may be configured such that the flexible shaft moves through the channel. The system may also include an operative member coupled with a distal end of the flexible shaft. The method may also include a step of inserting the operative member into a first end of a working channel, a step of moving the operative member through the working channel until the operative member passes out of the second end of the working channel, and a step of rotating the handle element to transmit torque to the operative member. The method may further include a step of positioning the operative member into a collapsed position prior to inserting the operative member into the working channel.

Some embodiments include a system for delivering treatment to a target area that may include a guide assembly. The guide assembly may include one or more transmission lines for operatively connecting an operative member to a power source, a flexible shaft enclosing at least a portion of the one or more power transmission lines, and a handle element. The flexible shaft may be configured for transmitting torque to the operative member. The handle element may include a body and a channel extending through the body. The flexible shaft may pass through the channel. The handle element may be configured such that the flexible shaft may move through the channel. The system may also include an expandable support device coupled with a distal end of the flexible shaft and an operative member disposed on the expandable support device. The operative member of the system may include a flexible circuit.

Some embodiments include an ablation device that may be configured for delivery through a working channel to a target treatment area. The ablation device may include a flexible circuit configured to transition between a collapsed configuration and an expanded configuration. The flexible circuit may include multiple parallel electrodes configured to collapse around an axis parallel to the multiple parallel electrodes.

The flexible circuit may also include a first bus coupled with a first subset of the multiple parallel electrodes and a second bus coupled with a second subset of the multiple parallel electrodes. The first bus and the second bus may be at least partially covered by one or more insulation layers. The insulation layers may be configured to impede the first and second bus from ablating the target treatment area. The one or more insulation layers may include polyimide.

The first bus may be located at a first end of the multiple parallel electrodes. The second bus may be located at a second end of the multiple parallel electrodes. The multiple parallel electrodes may be arranged in a row. The first bus and the second bus may be coupled with alternating electrodes in the row. The first bus and the second bus may each be arched. The first bus and the second bus may each include multiple arches. The end of each arch in the multiple arches may be coupled with a single electrode. The first bus may be configured to couple with a positive terminal. The second bus may be configured to couple with a negative terminal or a ground terminal.

The ablation device may also include an elastomeric body having a first surface and a second surface opposite the first surface. The flexible circuit may be disposed on the first surface of the elastomeric body. In some embodiments, the multiple parallel electrodes may each substantially extend to a distal end of the elastomeric body.

The elastomeric body having the flexible circuit disposed thereon may be configured to collapse around an axis parallel to the multiple parallel electrodes when disposed within a working channel and expand to a substantially flat orientation when the elastomeric body emerges from the working channel.

The ablation device may also include a first bus and a second bus disposed on the second surface of the elastomeric body. The first bus may be coupled with a first subset of the multiple electrodes and the second bus may be coupled with a second subset of the multiple electrodes. The elastomeric body may include one or more vias through which the first subset of electrodes couple to the first bus and one or more vias through which the second subset of electrodes couple to the second bus. The first bus and the second bus may be aligned substantially perpendicular to the multiple parallel electrodes. The first bus and the second bus may include copper. The first bus and the second bus may have a hash pattern with multiple void spaces. The first and second bus may be located between a first end of the multiple parallel electrodes and a second end of the multiple parallel electrodes.

Some embodiments include a system for delivering treatment to a target treatment that may include a guide assembly having a central axis, an elastomeric body coupled with the guide assembly, and a flexible circuit disposed on the elastomeric body. The flexible circuit may include multiple parallel electrodes configured to collapse around an axis parallel to the multiple parallel electrodes and parallel to the central axis of the guide assembly.

The system may also include one or more supports coupled with the elastomeric body and aligned parallel to the central axis of the guide assembly. At least one of the supports may include a superelastic material. The system may also include a working channel configured to receive the guide assembly, the elastomeric body, and the flexible circuit disposed on the elastomeric body. The elastomeric body and the flexible circuit may be in a collapsed configuration when disposed inside of the working channel. The elastomeric body and the flexible circuit may expand to a substantially flat orientation when the elastomeric body is outside the working channel.

Some embodiments include a method of delivering an ablation device to a target treatment area that may include a step of providing an ablation device. The ablation device may include a flexible circuit configured to transition between a collapsed configuration and an expanded configuration. The flexible circuit may include multiple parallel electrodes configured to collapse around an axis parallel to the multiple parallel electrodes. The method may also include a step inserting the ablation device into a first end of a working channel, and a step of moving the ablation device through the working channel until the ablation device passes out of a second end of the working channel. The method may also include a step of positioning the flexible circuit into a collapsed configuration prior to inserting the ablation device into the working channel.

Some embodiments include an expandable support device configured for delivery through a working channel and to a target treatment area that may include a solid support member having a perimeter and highly elastic or superelastic properties. The expandable support device may also include multiple splines formed in a pattern interior to the perimeter of the solid support member. Multiple voids may be located between adjacent splines. The width and a spacing of the multiple splines may be configured to promote expansion of the support member between a collapsed configuration and an expanded configuration providing a support surface.

The solid support member may include a proximal end, a distal end, and a central axis extending from the proximal end to the distal end. The pattern of the multiple splines may include a central axis spline substantially overlapping the central axis of the solid support member, a first subset of splines extending from the central axis spline towards a first lateral peripheral edge of the solid support member, and a second subset of splines extending from the central axis spline towards a second lateral peripheral edge of the solid support member opposite the first lateral peripheral edge.

The first subset of splines may be arranged in parallel to one another. The second subset of splines may be arranged in parallel to one another. The first subset of splines and the second subset of splines may extend from the central axis spline at an angle such that the first and second subsets of splines extend from the central axis spline towards the distal end of the solid support member. The first subset of spines and the second subset of spines may extend from the central axis spline at an angle in the range of from greater than 0 degrees to 90 degrees. The first subset of splines and the second subset of splines may extend from the central axis spline at an angle of about 45 degrees. The first subset of splines and the second subset of splines may have a thickness less than a thickness of the central axis spline.

The solid support member may include of a metal having shape memory properties. The support surface may define a curved surface in the expanded configuration. The support surface may define a substantially planar surface in the expanded configuration. The predetermined shape may correspond to a tissue surface at a treatment site in a patient. The solid support member may have a thickness of about 0.003 inch in some embodiments.

The pattern of the multiple splines may include multiple equally spaced vertical splines interconnected by horizontal splines. The expandable support may also include an operative member supported by the multiple splines. The operative member may be coupled with the multiple splines with an elastomeric adhesive. The operative member may include a flexible circuit. The flexible circuit may include multiple electrodes patterned to mirror the pattern of the multiple splines. The operative member may extend across an entire width of the solid support member. The solid support member may include a rounded distal edge. The solid support member may include a tapered proximal edge for promoting retraction of the device into the working channel.

Some embodiments include a system for delivering treatment to a target area that may include a solid support member having a perimeter and at least a highly elastic or superelastic properties, multiple splines formed in a pattern interior to the perimeter of the solid support member, and multiple voids between adjacent splines. The width and a spacing of the multiple splines may be configured to promote expansion of the support member between a collapsed configuration and an expanded configuration providing a support surface. The system may also include an operative member disposed on the solid support member.

The solid support member may have a first surface and a second surface opposite the first surface. The multiple splines may be disposed on the first surface and the operative member may be disposed on the second surface. The operative member may include a flexible circuit.

Some embodiments include a method of delivering an expandable support device to a target treatment area that may include a step of providing an expandable support device. The expandable support device may include a solid support member having a perimeter and at least highly elastic or superelastic properties. The expandable support device may also include multiple splines formed in a pattern interior to the perimeter of the solid support member and multiple voids between adjacent splines. A width and a spacing of the multiple splines may be configured to promote expansion of the support member between a collapsed configuration and an expanded configuration providing a support surface. The method may also include a step of inserting the expandable support device into a first end of a working channel, and a step of moving the expandable support device through the working channel until the expandable support device passes out of a second end of the working channel. The method may also include positioning the expandable support device into a collapsed configuration prior to inserting the expandable support device into the working channel.

Some embodiments include an expandable support device configured for delivery through a working channel and to a target treatment area that may include an expandable support member configured for supporting an operative member. The expandable support member may include multiple splines having a width and a spacing selected to promote expansion of the support member between a collapsed configuration and an expanded configuration. A portion of the support member may define a surface in the expanded configuration.

The multiple splines may include a central axis spline, a first subset of splines extending away from the central axis in a first direction, and a second subset of splines extending away from the central axis spline in a direction opposite the first direction. The first subset of splines may be arranged in parallel to one another. The second subset of splines may be arranged in parallel to one another. The first subset of splines and the second subset of splines may extend away from the central axis spline at an angle such that the first and second subsets of splines extend from the central axis spline towards a distal end of the central axis spline. The first subset of splines and the second subset of splines may extend away from the central axis spline at an angle in the range of from greater than 0 degrees to 90 degrees. The first subset of splines and the second subset of splines may extend away from the central axis spline at an angle of about 45 degrees. The first subset of splines and the second subset of splines may have a thickness less than a thickness of the central axis spline. The multiple splines may include nitinol. The multiple splines may include a central axis spline, multiple secondary splines arranged in parallel to the central axis spline, equally space apart from one another, and on either side of the central axis spline, and multiple interconnecting splines arranged transverse to the secondary splines and interconnecting the secondary splines.

Some embodiments include a system for providing treatment to a target treatment area that may include an expandable support member configured for supporting an operative member. The expandable support member may include multiple splines having a width and a spacing selected to promote expansion of the expandable support member between a collapsed configuration and an expanded configuration. A portion of the expandable support member may define a surface in the expanded configuration. The system may also include a solid elastomeric body. The expandable support member may be disposed on the solid elastomeric body within a perimeter of the solid elastomeric body. The system may also include an operative member coupled with the solid elastomeric body.

The multiple splines may include a central axis spline, a first subset of splines extending away from the central axis in a first direction, and a second subset of splines extending away from the central axis spline in a direction opposite the first direction. The first subset of splines may be arranged in parallel to one another. The second subset of splines may be arranged in parallel to one another. The first subset of splines and the second subset of splines may extend away from the central axis spline at an angle such that the first and second subsets of splines extend from the central axis spline towards a distal end of the central axis spline. The first subset of splines and the second subset of splines may extend away from the central axis spline at an angle of about 45 degrees. The operative member may be coupled with the solid elastomeric body with an elastomeric adhesive.

The operative member may be a flexible circuit. The flexible circuit may include multiple electrodes patterned to mirror the multiple splines. The operative member may extend across an entire width of the solid elastomeric body.

Some embodiments include a method of delivering an expandable support device to a target treatment area that may include a step of providing an expandable support device configured for delivery through a working channel to a target treatment area. The expandable support device may include an expandable support member configured for supporting an operative member. The expandable support member may include multiple splines having a width and a spacing selected to promote expansion of the support member between a collapsed configuration and an expanded configuration. A portion of the support member may define a surface in the expanded configuration. The method may also include a step of inserting the expandable support device into a first end of the working channel, and a step of moving the expandable support device through the working channel until the expandable support device passes out of a second end of the working channel. The method may also include a step of positioning the expandable support device into a collapsed position prior to inserting the expandable support device into the working channel.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWING

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 6A is plan view of a flexible support coupled with an expandable support device according to various embodiments.

FIG. 6B is a plan view of two flexible supports coupled with an expandable support device according to various embodiments.

FIG. 6C is a plan view of three flexible supports coupled with an expandable support device according to various embodiments.

FIGS. 9A-9C are cross sectional views of varying numbers of flexible supports coupled with an expandable support device according to various embodiments.

FIGS. 10A-10C are cross-sectional views of varying numbers of flexible supports coupled with an expandable support device according to various embodiments.

FIGS. 13A-13L are plan views and side views of patterned solid substrates according to various embodiments.

FIGS. 15A-15B are plan views of an electrode structure for an operative member according to various embodiments.

FIGS. 18A-18B are perspective views of a guide assembly according to various embodiments.

FIGS. 19A-19B are perspective views of a guide assembly according to various embodiments.

FIGS. 27A-27F are cross-sectional views of a method for making an operative member and coupling it with a flexible support according to various embodiments.

DETAILED DESCRIPTION

Figure 1A:
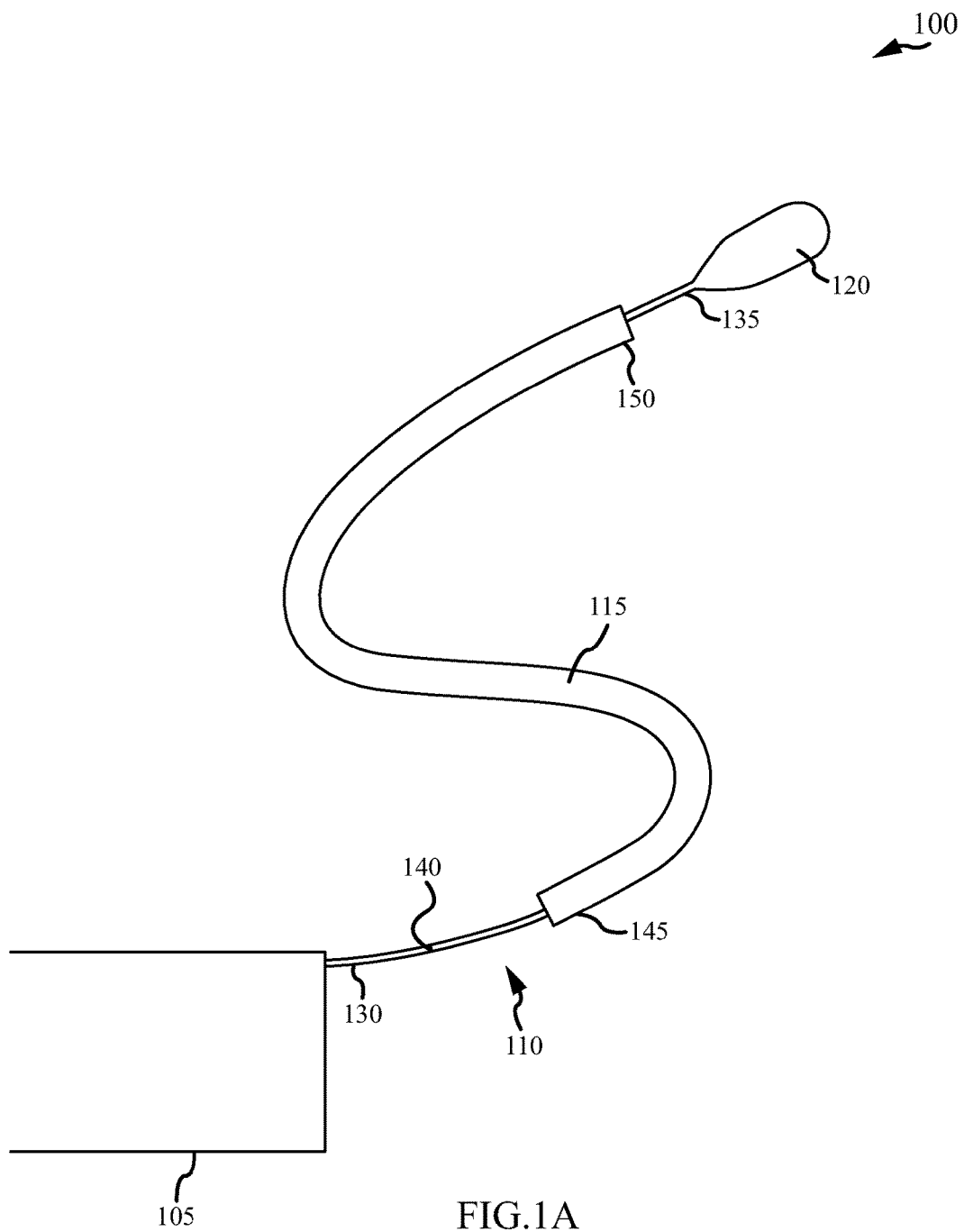
FIG. 1A is a schematic diagram of a system for delivering treatment to a target treatment area including components configured according to various embodiments.

Methods, systems, and devices are described for providing treatment to a target site, such as a site within a body lumen. Systems may include an expandable support device that may be coupled with a distal end of a guide assembly. An operative member can be disposed on the expandable support device such that moving the expandable support device to the target site using the guide assembly delivers the operative member to the target site. The guide assembly may be utilized to transmit torque and/or to rotate to the expandable support device and/or the operative member.

The expandable support member can include a solid body of elastomeric material. The elastomeric material can be flexible so that it may transition between a folded, or collapsed configuration and a planar, or expanded, configuration. One or more flexible supports can be coupled with the elastomeric body such that the flexible supports are each aligned parallel to a central axis of the elastomeric body. The flexible supports can be made from at least a highly elastic, such as spring steel, or a superelastic material, such as nitinol, and can be arranged in a single central axis configuration, a wishbone configuration, a trident configuration, or other configurations, including open and closed configurations.

The expandable support member can include a solid support member made from a highly elastic or superelastic material that is supported by multiple splines located within the perimeter of the solid support member. The multiple splines can be separated by voids so as to create a pattern of splines having a width and spacing that promotes transitioning of the solid support member between a collapsed configuration and an expanded configuration. The splines can be arranged in a pattern wherein a spline arranged to substantially overlap a central axis of the solid support member has splines extending away from the central spline in both directions towards a distal end of the solid support member.

The operative member can include a flexible circuit capable of bending with the expandable support device upon which it is disposed. The flexible circuit can include multiple electrodes aligned in parallel to one another. The electrodes can also be aligned in parallel to an axis about which the flexible circuit collapses from a planar configuration to a folded configuration so that the electrodes do not substantially impede the transition between an expanded configuration and a collapsed configuration. The flexible circuit can include a first bus at one end of the parallel electrodes and a second bus at the opposite end of the electrodes. The electrodes can be coupled with the first and second bus in an alternating pattern.

The guide assembly that can be used to move the expandable support device can include a first shaft portion and a second shaft portion separated by a break. Transmission lines can extend through both the first shaft and the second shaft. The break between the first shaft and the second shaft can allow the first shaft to rotate independently of the second shaft. The first shaft can be configured such that rotation of the first shaft transmits torque and/or rotation to the expandable support device.

With reference to FIG. 1A, a general system 100 for delivering treatment to a target treatment area is shown in accordance with various embodiments. The system 100 may be designed for providing treatment to a target area inside of a body, such as the wall of an organ or lumens in the gastrointestinal tract, for example. The system 100 can include a power source 105, a guide assembly 110, a working channel 115, and/or an expandable support device 120. The expandable support device 120 may generally be configured to support an operative member that is used to supply therapy to the target treatment area. The system 100 may operate by positioning at least a portion of the working channel 115 inside a body and passing the expandable support device 120 through the working channel 115 using the guide assembly 110 such that the expandable support device 120 may be delivered to a target treatment area inside the body. The power source 105 may then be used to supply power to an operative member disposed on the expandable support device 120 so that therapy can be applied to the target treatment area.

The expandable support device 120 can be a self-expanding device capable of transitioning between a collapsed configuration and an expanded configuration with little or no use of supplementary expansion mechanisms. The collapsed configuration may be generally used when the expandable support device 120 is inside of the working channel 115. When the expandable support device 120 emerges from the working channel 115, the expandable support device 120 may self-expand, such as by transitioning from a curved orientation (i.e., the collapsed configuration) to a substantially planar orientation (i.e., the expanded configuration).

The expandable support device 120 can be configured to support an operative member. In some embodiments, the operative member is a therapeutic or diagnostic instrument, such as an ablation element that can provide ablative energy to the target treatment area. Some operative members may be designed so that they make direct contact with a target treatment area, including pressing of the operative member against the target site.

The expandable support device 120 may be coupled with the guide assembly 110 such that the guide assembly 110 can be used to maneuver the expandable support device 120 through the working channel 115 and at the target treatment area. The guide assembly 110 may include a proximal end 130 and a distal end 135, with the proximal end 130 configured to be coupled with the power source 105 and the distal end 135 configured to be coupled with the expandable support device 120. In some embodiments, the guide assembly 110 includes a break 140 that allows the distal portion of the guide assembly 110 to rotate independently of the proximal portion of the guide assembly 110. The break 140 may typically be located outside of the working channel 115 and proximate the power source 105. Rotating the distal portion of the guide assembly 110 can provide torque to the expandable support device 120 and allow for better movement and control of the expandable support device 120 at the target treatment area.

The working channel 115 may include a proximal end 145 and a distal end 150, and can be configured such that the expandable support device 120 can be inserted into the working channel 115 at the proximal end 145 and guided through the length of the working channel 115 using the guide assembly 110 until it emerges from the distal end 150 of the working channel 115. In some embodiments, the expandable support device 120 is positioned in a collapsed configuration prior to being inserted into the working channel 115 so that the expandable support device 120 fits inside of the working channel 115 and remains in a collapsed configuration as the expandable support device 120 moves through the working channel 115. The working channel 115 can be oriented such that the distal end 150 is proximate the target treatment area. In such configurations, the expandable support device 120 may be located near or at the target treatment area when it emerges from the distal end 150 of the working channel 115.

The power source 105 can generally be provided to provide power to the operative member that may be coupled with the expandable support device 120 and/or the operative member disposed thereon. In some embodiments, power is provided from the power source 105 to the expandable support device 120 via one or more transmission lines extending between the power source 105 and the expandable support device 120 and housed within the guide assembly 110.

Figure 1B:
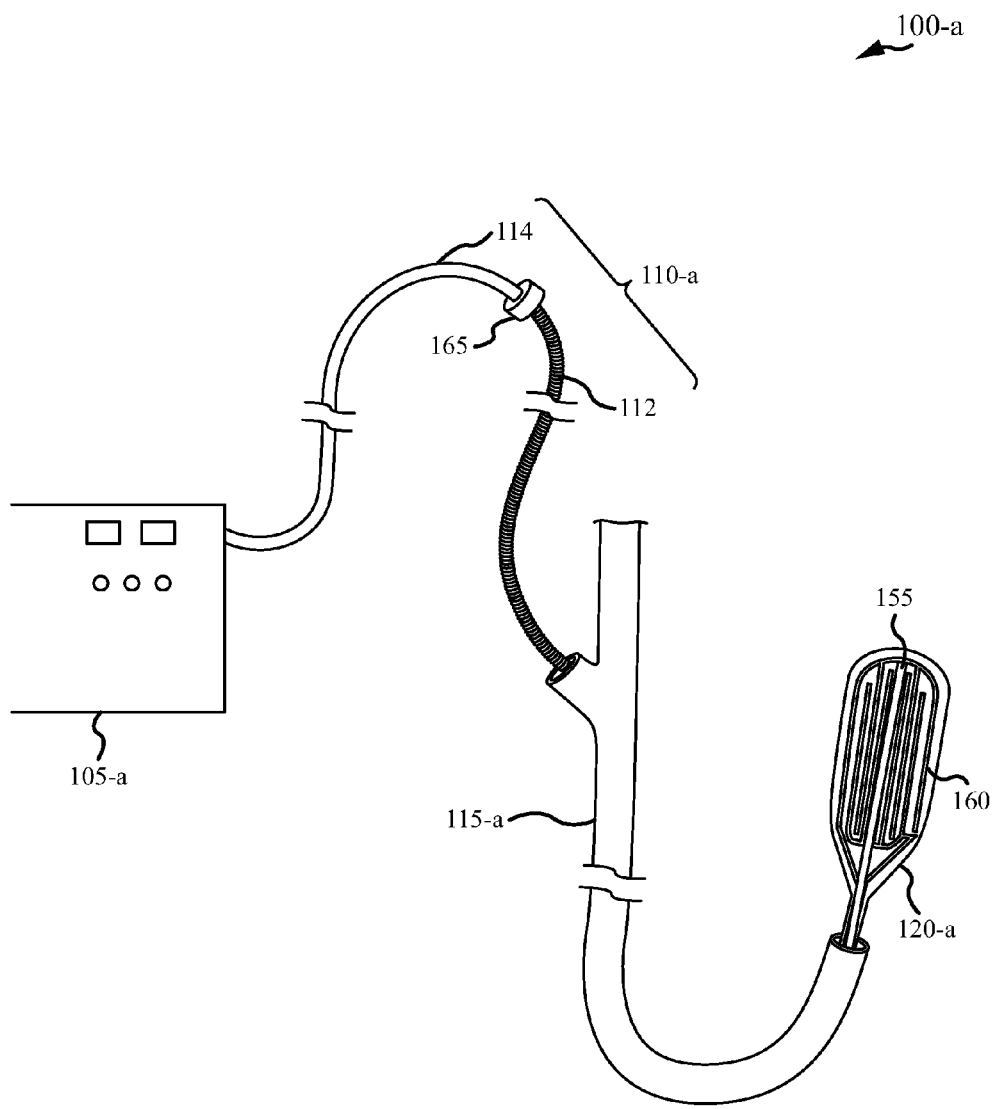
FIG. 1B is schematic diagram of one specific embodiment of the system shown in FIG. 1A.

FIG. 1B illustrates a system 100-a that may be an example of the system 100 shown in FIG. 1A according to various embodiments. The system 100-a may include a generator 105-a, a guide assembly 110-a that may include a first shaft 112 and a second shaft 114, an endoscope 115-a, an expandable support device 120-a, a flexible support 155 extending along the central axis of the expandable support device 120-a, and/or an operative member 160 supported by the expandable support device 120-a.

The expandable support device 120-a may include a solid elastomeric body on which the operative member 160 is supported. The expandable support device 120-a may thus be a flexible material capable of being curved or folded. The expandable support device 120-a may generally have a paddle shape, including a rounded distal end. The expandable support device 120-a may taper at the proximal end and couple to the guide assembly 110-a.

Disposed on one surface of the expandable support device 120-a may be an operative member 160 that may be configured to provide treatment to the target treatment area. As shown in FIG. 1B, the operative member 160 may be a series of electrodes aligned in parallel to one another and that extend from the proximal end of the expandable support device 120-a to the distal end of the expandable support device 120-a. The electrodes may be interlaced, with approximately half of the electrodes extending from a first bus located at the proximal end of the expandable support device 120-a and approximately half of the electrodes extending from a second bus located at the distal end of the expandable support device 120-a. The first bus or the second bus may be connected to a positive terminal and the other of the first bus or the second bus may be connected to a negative or ground terminal to thereby provide a bipolar electrode configuration. When connected to the generator 105-a, the electrodes can provide ablative energy to the target treatment area.

Also included on the expandable support device 120-a may be a flexible support 155, which can be made from nitinol so that the flexible support 155 exhibits superelastic properties. The flexible support 155 may generally extend from the proximal end of the expandable support device 120-a to the distal end of the expandable support device 120-a along a central axis of the flexible support device 120-a. The flexible support 155 can be located on a surface of the expandable support device 120-a opposite the surface on which the operative member 160 may be disposed. The flexible support 155 may give the expandable support device 120-a a desired amount of structure so that the flexible support device 120-a can be transported through the guide assembly 110 without crumpling upon itself. The flexible support 155 can also provide apposition force when the expandable support device 120-a is deflected against a target treatment area, such as tissue.

The expandable support device 120-a may be coupled with the guide assembly 110, which is split into a first shaft 112 and a second shaft 114. A common set of transmission wires may extend from the generator 105-a to the expandable support device 120-a and through both the first shaft 112 and the second shaft 114. The break 140 shown in FIG. 1A may serve as the dividing point between the first shaft 112 and the second shaft 114, and may allow the first shaft 112 to rotate independently of the second shaft 114. A protection element 165 may be coupled with the first shaft 112 and extend over a portion of the second shaft 114 to thereby cover the break 140 and protect the transmission lines running through the guide assembly 110. Because the protection element 165 may be coupled with the first shaft 112, the protection element 165 can also serves as a torque handle that can be rotated to rotate the first shaft 112 and provide torque to the expandable support device 120-a. The first shaft 112 may be flexible and can be made from stainless steel, such as coiled stainless steel wires.

The endoscope 115-a may be provided for accessing a target treatment area within a body. In some embodiments, the endoscope 115-a includes one working channels and the expandable support device 120-a and the guide assembly 110 can be passed through the one working channel in the endoscope 115-a to reach the target treatment area. The endoscope 115-a can include partitions to create multiple channels, where at least one of the channels may be a working channel, and the expandable support device 120-a and the guide assembly 110 can be passed through one of the channels in the endoscope 115-a to reach the target treatment area. In some embodiments, the endoscope 115-a is passed into the body through the mouth and provides access to the esophagus.

Figure 2:
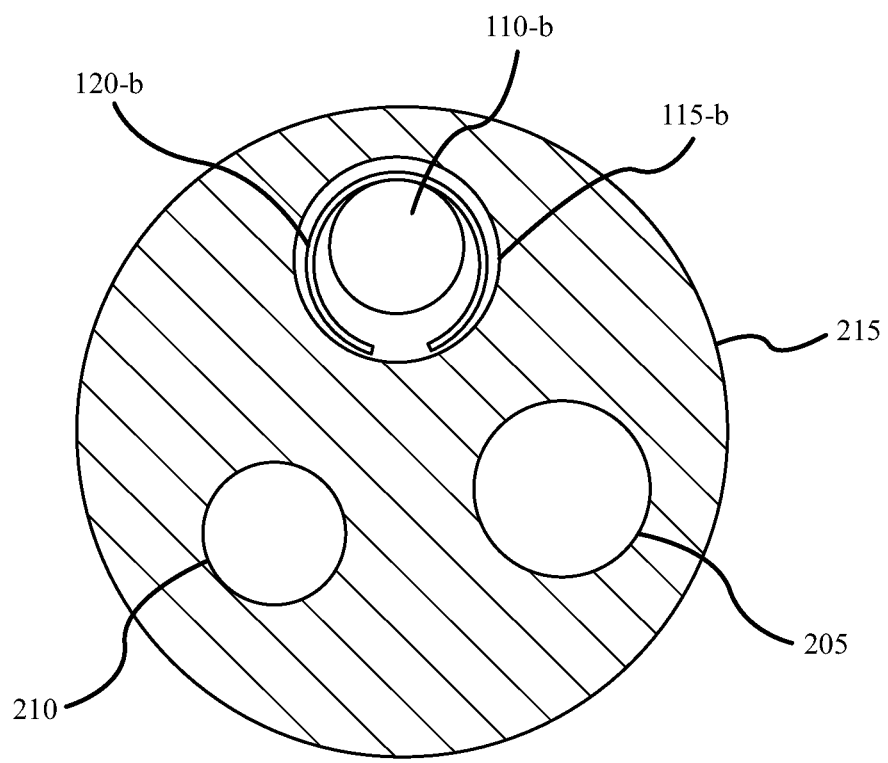
FIG. 2 is a cross-sectional view of an expandable support device in a working channel according to various embodiments

FIGS. 2-5 provide further detail on the expandable support device 120 illustrated in FIG. 1 in accordance with various embodiments. With reference to FIG. 2, the expandable support device 120-b may be coupled with the guide assembly 110-b. Although not shown in FIG. 2, the expandable support device 120-b may carry an operative member for delivering therapy to a target treatment area.

Expandable support device 120-b is shown in FIG. 2 in a collapsed configuration within the working channel 115-b in accordance with various embodiments. Two additional channels 205 and 210 may be provided, and the three channels 115-b, 205, 210 may be housed within an outer casing 215. While FIG. 2 shows the outer casing 215 having three channels, the outer casing 215 may have fewer or more channels. The additional channels may be used for a variety of purposes, including for providing suction, aspiration, illumination, magnification, and/or delivery of other instruments to the target treatment area. In some embodiments, the outer casing 215 is an endoscope having one or more channels within the endoscope. A typical endoscope arrangement may have three channels, with one working channel provided for the expandable support device, one channel for a camera and the associated wiring, and one channel for a light source. It may be desirable to provide a working channel capable of receiving two or more devices, such as the expandable support device 120-b and a suction device. In some embodiments, the expandable support device 120-b is removed when suction is activated.

One may appreciate that the term working channel may refer to a wide variety of channels used for providing instruments to target areas. For example, in a bronchoscope, a working channel may be referred to as a biopsy port. As will be described further herein, the expandable support device 120 in accordance with various embodiments described herein may be used with a variety of instruments depending on the medical application.

Figure 3A:
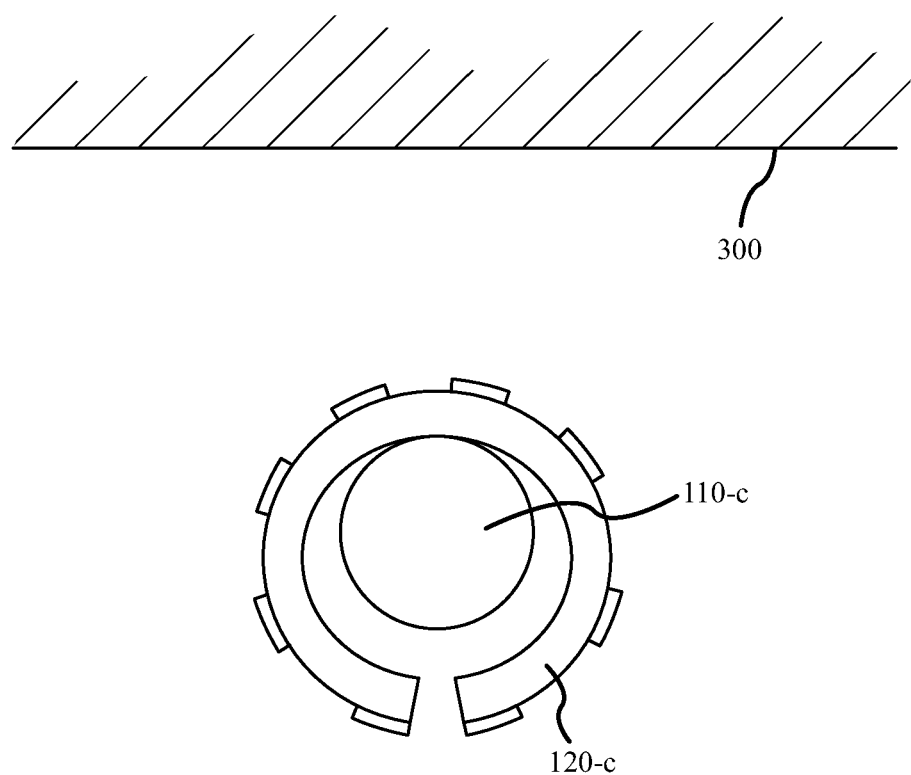
FIGS. 3A-3C are cross-sectional views of a collapsed and expanded expandable support device positioned proximate a target treatment area according to various embodiments.

With reference to FIG. 3A, the expandable support device 120-c is shown in a collapsed configuration in accordance with various embodiments. The expandable support device 120-c may be configured for transitioning between the collapsed configuration shown and an expanded configuration shown in FIG. 3B or FIG. 3C. The expandable support device 120-c may be configured for insertion into a working channel in the collapsed configuration. When the expandable support device 120-c is delivered out of an end of the working channel, it may transition to the expanded configuration. In the expanded configuration, at least one dimension of the expandable support device 120-c may have increased. When an operative member is disposed on the expandable support device 120-c, the operative member may also transition between an expanded configuration and a collapsed configuration. In various embodiments, the expanded configuration is significantly larger than the collapsed configuration and allows the expandable support device 120-c to contact a treatment surface 300. As will be described below, the expandable support device 120-c itself does not necessarily increase in size. Rather, in various respects, "expansion" refers to the radial expansion, increase in three-dimensional space, and/or opening of the device.

In various embodiments, the expandable support device 120-c is releasably retained in the collapsed configuration by a working channel (not shown in FIG. 3A). One may appreciate from the description herein that the collapsed and expanded configuration may be reversed. In various embodiments, the expandable support device 120-c is configured to self-collapse from an expanded configuration.

As shown, for example, in FIG. 3A, the expandable support device 120-c may have a rounded or curved shape in the collapsed configuration. The exemplary collapsed shape may generally conform to the inner wall surface of a working channel. The outer surface of the expandable support device 120-c may generally remain in contact with the wall of the working channel along its entire surface. In some cases, the expandable support device 120-c may be configured such that the collapsed configuration results in different shapes. The expandable support device 120-c may tend to have a rounded shape without creases or sharp radiuses when it collapses. This can be due in part to the operative member disposed on the expandable support device 120-c resisting bending. In some embodiments, the expandable support device 120-c collapses into a U-shape.

It may be desirable to have a generally uniform radius in the collapsed configuration. It may be desirable for the whole collapsed expandable support device 120-c to expand against the inner wall surface of a working channel. As would be understood by one of skill in the art, this may maximize the chord length and enable the delivery of a larger surface in the working channel.

One may appreciate that the collapsed configuration size and shape may depend on the particular application and instruments being used. The outer casing 215 may be an endoscope having one or more working channels. A typical endoscope working channel may have a diameter of about 1 mm, about 2 mm, about 3 mm, about 5 mm, about 8 mm, or about 10 mm. In various embodiments, the expandable support device 120-c collapses to permit insertion through a working channel diameter of about 1.2 mm, about 1.7 mm, about 2.0 mm, about 2.6 mm, about 2.8 mm, about 3.7 mm, about 5.0 mm, or about 6.0 mm. Some endoscope working channels may have other diameters.

Although reference has been made to the outer casing 215 being an endoscope, one may appreciate that the expandable support device 120-c may be used with a variety of delivery instruments including, but not limited to, a catheter. Moreover, the expandable support device 120-c may be delivered through various types of working channels, such as catheter lumens, a cannula lumen, or a lumen in the body of a patient. The expandable support device 120-c may also be configured for use with a variety of other instruments as would be understood by one of skill in the art. For example, the expandable support device 120-c may be delivered using an introducer or other delivery device. The expandable support device 120-c may be held in a collapsed configuration with a sheath, a fastener, or a similar device.

Figure 3B:
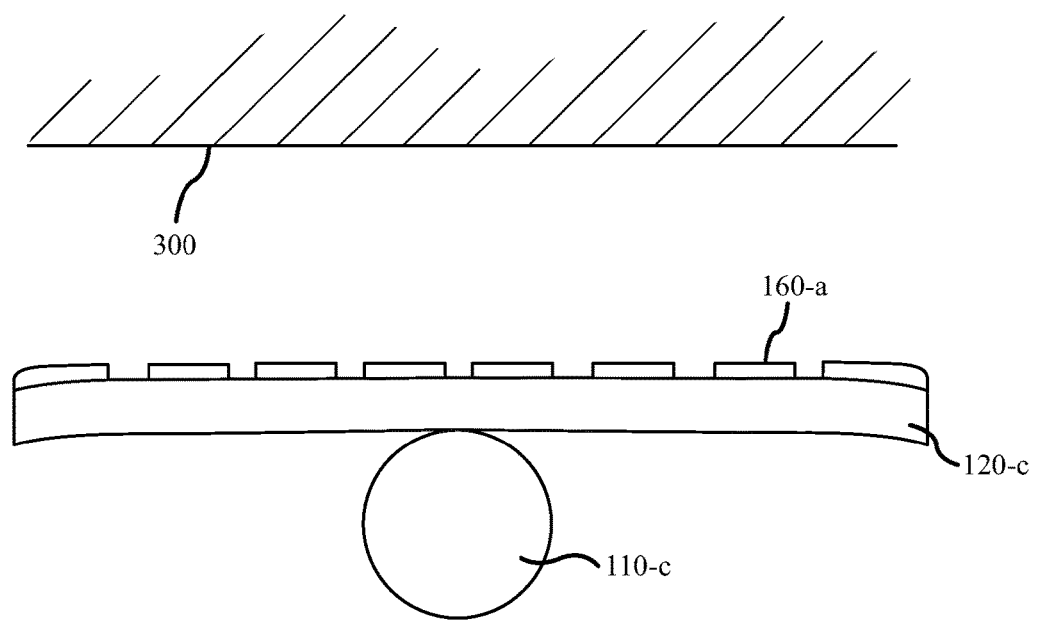

With reference to FIG. 3B, the expanded configuration of the expandable support device 120-c may have a substantially planar shape relative to the collapsed configuration shape shown in FIG. 3A. The expandable support device 120-c may have an expanded configuration whereby a surface of the expanded support device 120-c on which the operative member 160-a may be disposed has a generally flat shape with a minimal, laterally-curved bias. The expandable support device 120-c in the expanded configuration may present an outwardly facing treatment surface towards a target treatment area 300. The expandable support device 120-c in the expanded configuration may have a planar treatment surface. In various embodiments, in the expanded configuration most, or all, of the treatment surface is flat. In various embodiments, in the expanded configuration a central portion of the treatment surface is essentially flat and the outer regions are slightly curved.

With continuing reference to FIG. 3B, the operative member 160-a may be disposed on the expandable support device 120-c. The expandable support device 120-c may be attached to a distal end of a guide assembly 110-c. In an exemplary embodiment, the guide assembly 110-c is positioned within a working channel to guide the expandable support device 120-c through and out of the working channel. The guide assembly 110-c may allow a user to manipulate the expandable support device 120-c from a proximal end of the guide assembly 110-c. The guide assembly 110-c may allow the expandable support device 120-c to be pushed, pulled, and rotated.

Figure 3C:
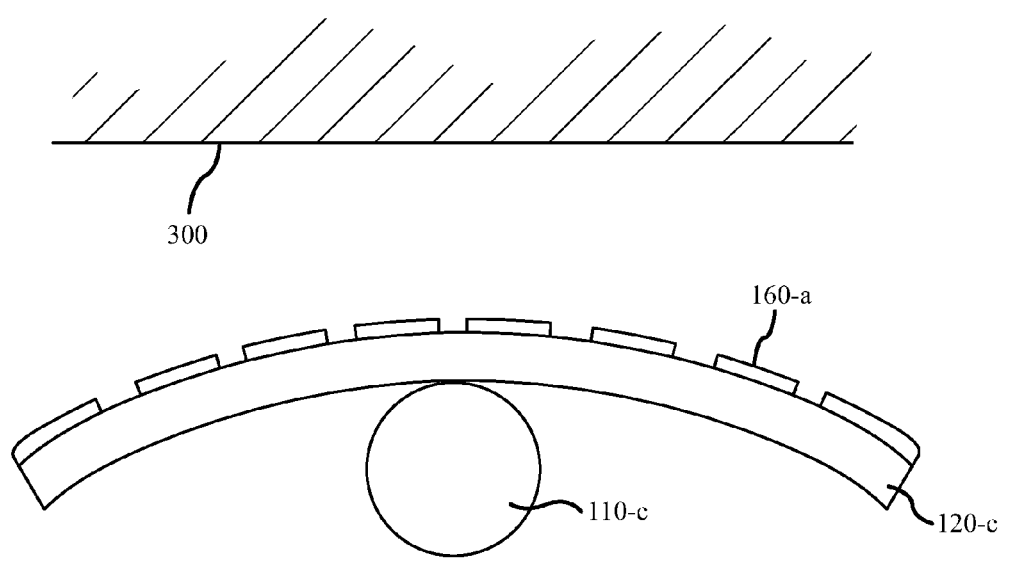

With reference to FIG. 3C, the expanded configuration of the expandable support device 120-c may have a curved shape. In some embodiments, the curved shape of the expanded configuration is less curved than the curved shape of the collapsed configuration shown in FIG. 3A. In other words, the radius of the expandable support device 120-c in the expanded configuration may be greater than the radius of the expandable support device 120-c in the collapsed configuration. Expanded configurations having a curve as shown in FIG. 3C can be beneficial for providing uniform tissue contact against a curved surface, such as can be the case for an esophagus.

Figure 4:
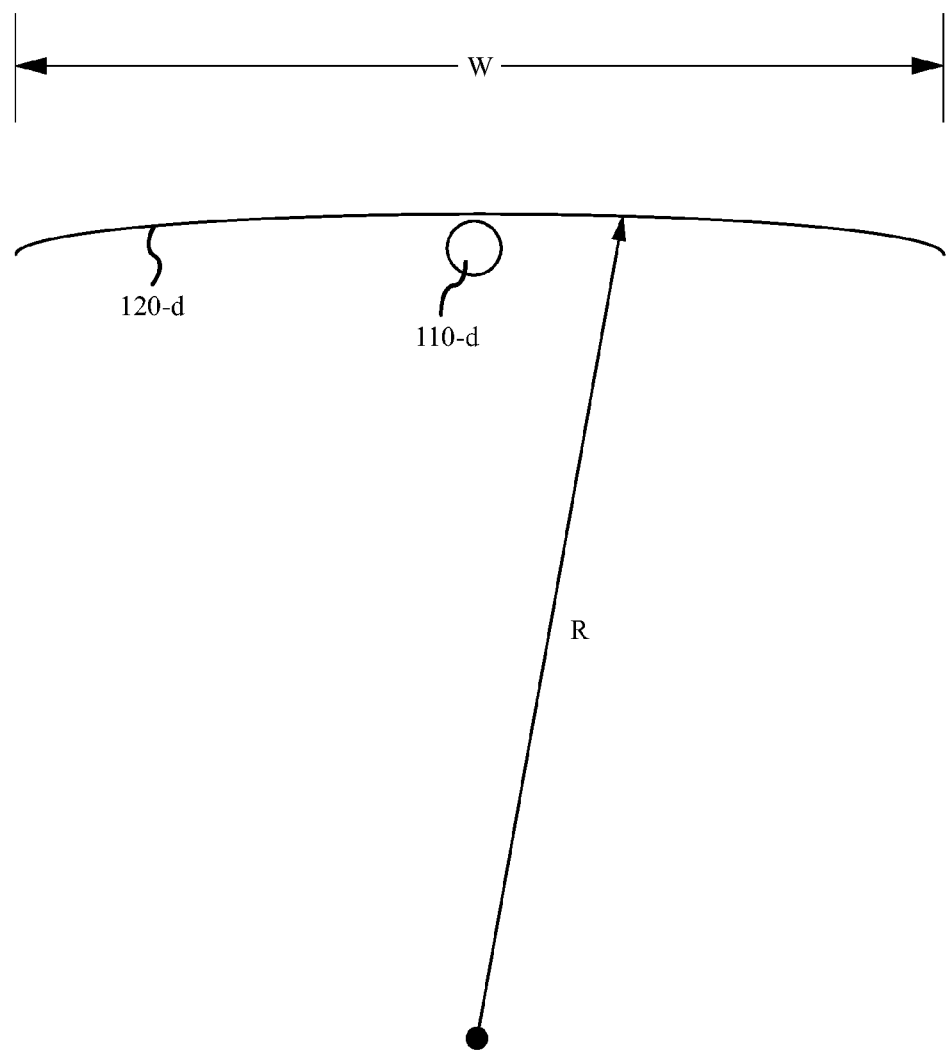
FIG. 4 is a simplified line drawing illustrating an expandable support device in an expanded configuration according to various embodiments.

With reference to FIG. 4, a simplified schematic view of an expanded support device 120-d in an expanded configuration is shown in accordance with various embodiments. The shape of the expandable support device 120-d in the expanded configuration may be planar. The expandable support device 120-d may define a surface with a slight curvature having a radius "R". The surface of the expandable support device 120-d may have a width "W". As will be described below in additional detail, the width W of the expandable support device 120-d may be wider than a diameter of the working channel ($W_c$) from which it is deployed. In various embodiments, however, the radius R is at least an order of magnitude larger than W and $W_c$. In various embodiments, the ratio R/W is at least 2, at least 5, at least 10, or more than 100. In various embodiments, the expandable support device 120-d in an expanded configuration defines a completely flat surface with no radius.

It may be desirable to provide an expandable support device 120-d that deploys a relatively large surface area. In other words, it may be desirable to have an expandable support device 120-d in an expanded configuration that has a large width relative to the working channel. The ability of the expanded support device 120-d to expand from the working channel may allow for a $W/W_c$ ratio greater than 1. In various embodiments, the ratio of $W/W_c$ is at least 1.5, at least 2, at least 5, at least 10, or more than 100. In other embodiments, the ratio of $W/W_c$ may take on other values.

Figure 5A:
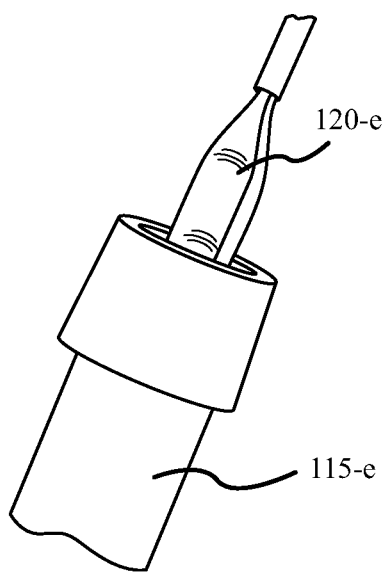
FIGS. 5A-5F are perspective views of various stages of an expandable support device being passed through a working channel according to various embodiments.
Figure 5B:
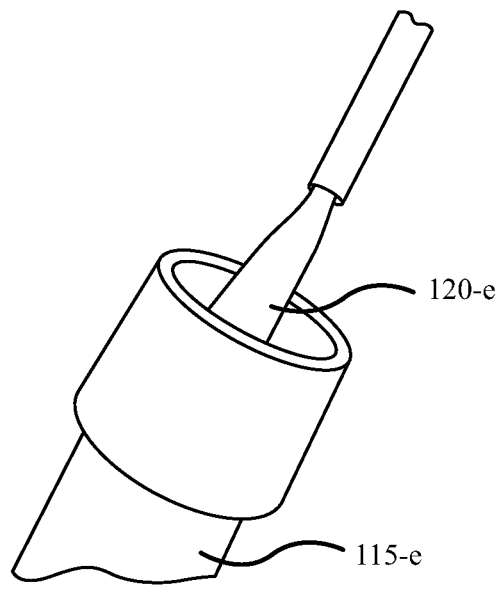
Figure 5C:
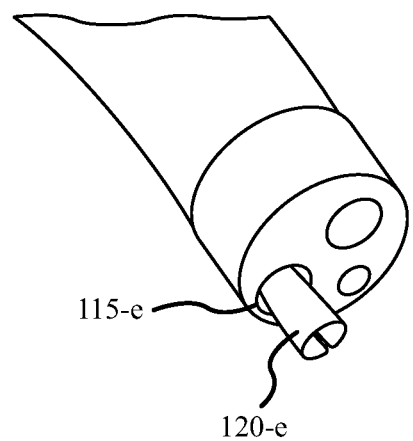
Figure 5D:
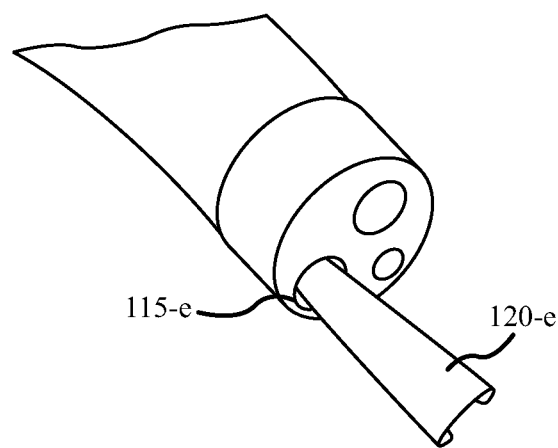
Figure 5E:
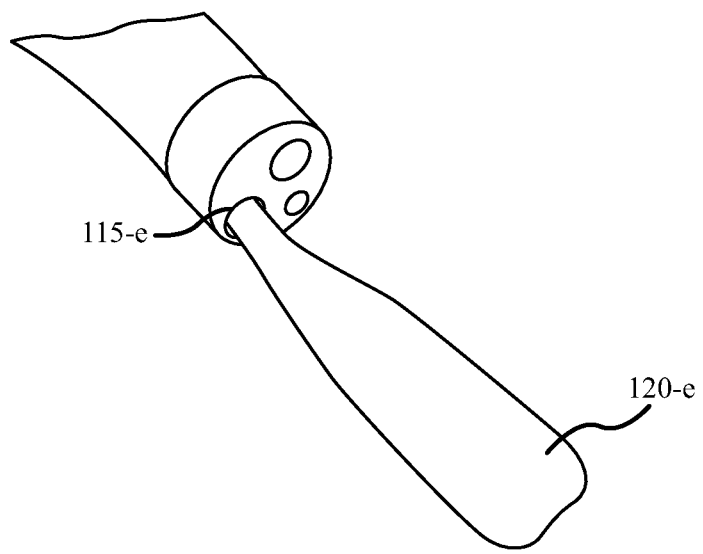

The general nature of delivery and deployment of the expandable support device in accordance with various embodiments may now be described with reference to FIGS. 5A-5F, which are perspective views of an expandable support device 120-e entering a working channel 115-e at a first end and exiting a working channel 115-e at a second end opposite the first end. As shown in FIGS. 5A-5F, expandable support device 120-e may be configured to expand from the collapsed configuration in working channel 115-e to an expanded configuration out of the working channel 115-e. In FIG. 5A and FIG. 5B, the expandable support device 120-e may be rolled or folded to accommodate delivery through a small diameter of the working channel 115-e. In FIG. 5C and FIG. 5D, the expandable support device 120-e may begin to exit the working channel 115-e. In FIG. 5C, only a distal end of the expandable support device 120-e may have emerged from the working channel 115-e, and as a result, the expandable support device 120-e remains mostly in the collapsed configuration. In FIG. 5D, more of the expandable support device 120-e may have emerged from the working channel 115-e, and as a result, the expandable support device 120-e may begin to transition from the collapsed configuration to the expanded configuration. In FIG. 5E, the expandable support device 120-e may fully emerge from the working channel 115-e and is therefore in the fully expanded configuration. In the expanded configuration shown in FIG. 5E, the expandable support device 120-e may be unfolded into a generally planar surface shaped to contact a target area. Although referred to as "expansion," the surface of the expandable support device 120-e may change shape during expansion but does not actually change surface area. Rather, the expandable support device 120-e may open up in a wing-like fashion to present a larger surface area to a treatment area. As shown in FIG. 5E, for example, the expandable support device 120-e in the expanded configuration better conforms to a treatment area.

In various embodiments, the collapsed configuration has a small contact surface and the expandable support device is configured to expand to provide a broad surface. In the case of treating a gastrointestinal (GI) tract, for example, the contact surface of the expandable support device may be significantly larger in the expanded configuration. This may be due in part because the GI tract has a larger diameter than exemplary working channel. The larger radius of the GI tract wall may present a relatively flatter contact surface. However, a completely flat expandable support device may have poor contact of the expandable support device with the comparatively rounded GI tract wall. In various embodiments, the shape and dimensions of the expanded configuration are selected to conform to the treatment site, such as the inner lumen wall. For example, the expandable support device may have a deployed curviplanar shape that corresponds to the radius of curvature of the treatment area.

One of skill in the art may appreciate that the inner walls of many body lumens may not be planar or perfectly round. Many body lumens are rough. Some body lumens include trabeculae or folds along the inner surface. In various embodiments, the expandable support device in an expanded configuration has a shape selected based on the wall surface to be treated. For example, the expandable support device in the expanded configuration may include waves or undulations. The expandable support device in the expanded configuration may have a shape that matches the shape of the target surface. The expanded support device in an expanded configuration may have a flat shape to smooth out a rough or folded target surface.

In various embodiments, expanded support device is configured to improve apposition in the expanded configuration. In various embodiments, the expandable support device has sufficient rigidity in the expanded configuration to provide a contact force at the treatment site and achieve good apposition. In various embodiments, the expandable support device in the expanded configuration has adequate rigidity to apply pressure to the treatment surface, for example, to pressure vasculature in the tissue for hemostasis.

In general, the expanded force is within a range to allow the expandable support device to be collapsed back into the working channel while providing sufficient expansion force for delivering treatment. In an exemplary embodiment, operative member disposed on the expandable support device comprises a malleable copper and a thin insulator. As such, the operative member tends to resist changing shape. Thus the expansion force of expandable support device is sufficient to ensure self-expansion in view of the operative member resistance and other environmental factors.

In various respects, the expansion force is selected to adjust a contact force (also referred to as deflection force) of the expandable support device with the treatment area surface. The expansion force may vary depending on the application. For example, a body lumen in the alimentary tract is typically stronger and able to withstand a greater internal force than a blood vessel. The expansion force may depend on the treatment surface area required. For example, less force may be necessary for an expandable support device configured for deploying in an artery. The expansion force may also vary depending on the treatment. For example, a hemostasis device for the vasculature may require less expansion force than an ablation device for the esophagus. Other factors that can impact the contact force include the flexible support and the working channel deflection.

In various embodiments, the expandable support device is dimensioned and configured to exert an expansion force (i.e., radial force) of at least 5 GPa when it is in the collapsed configuration. In various embodiments, the expansion force is equal to or greater than the bending strength of the operative member disposed on the expandable support device. In various applications, it may be desirable to reduce the expansion force to reduce the risk of injury to the vessel in which the expandable support device is to be deployed. A large expansion force, for example, may damage a blood vessel. In various embodiments, the expandable support device is configured to deploy gradually, or at selected time intervals, rather than snap open. In various embodiments, the expandable support device is configured to exert a non-uniform expansion force. For example, the outer edges of the expandable support device may exert a lower or higher expansion force. In various embodiments, when the expandable support device is in the expanded configuration the expansion force along its outer edge is at least 0.5 GPa, at least 5 GPa, at least 25 GPa, or at least 40 GPa. Some embodiments may utilize other expansion force values. The expandable support device may include features to reduce the risk of injury such as a curviplanar treatment surface and rounded edges.

In various embodiments, the expandable support device is configured to apply sufficient force to smooth out the inner wall surface at the treatment site. For example, the expandable support device can be pressed against the inner wall surface to unfold the folds in the wall.

One may appreciate from the description herein that the expanded configuration of the expandable support device plays a role in the parameters of the expandable support device's contact with the treatment site. If the expandable support device expands to a completely flat shape and is extremely rigid, the expandable support device may not make good contact with a rounded surface. Likewise, if the expandable support device in an expanded configuration has some flexibility, it may be able to conform, to a degree, to the treatment surface. An expandable support device with a rounded surface in an expanded configuration may be less appropriate for contacting a generally flat treatment site. In some applications, it may be desirable to achieve less than full contact of the expandable support member with the treatment site. The expandable support device may have an expanded configuration of a fixed shape and size selected to provide more contact with larger diameter lumens and less contact with smaller diameters lumens, or vice versa. For example, the expanded configuration may have a small radius such that it achieves more contact with a smaller lumen and allows for spot treatment of a larger lumen. This configuration may be appropriate for delivering more energy to differently sized body lumens using the same device.

In another example, the expanded support device in the expanded configuration may include several different treatment surfaces for different parts of a body. In various embodiments, the treatment surface is on an underside of the expanded support device. In this manner, the expanded support device may be deployed through a narrow aperture (e.g., lower esophageal sphincter) to treat abnormal tissue on the other side (e.g., stomach lining). In one example, the treatment surface is cup-shaped, for example, to treat abnormal cervical tissue.

In various embodiments, expandable support device include a first treatment surface and at least another treatment surface. The another treatment surface may be substantially planar or another shape. The treatment surface and the another treatment surface may be contiguous.

In various embodiments, the expanded configuration of expandable support device is adjustable. For example, a supplementary expansion device may be provided to increase expansion—further flatten and unroll the expandable support device—or decrease expansion. In various embodiments, the supplementary expansion device is an expandable member (e.g. a balloon) or an actuator. The expanded configuration may be adjusted manually or automatically. The expanded configuration adjustment may be determined by a user with user controls or predetermined based on preset parameters.

Figure 5F:
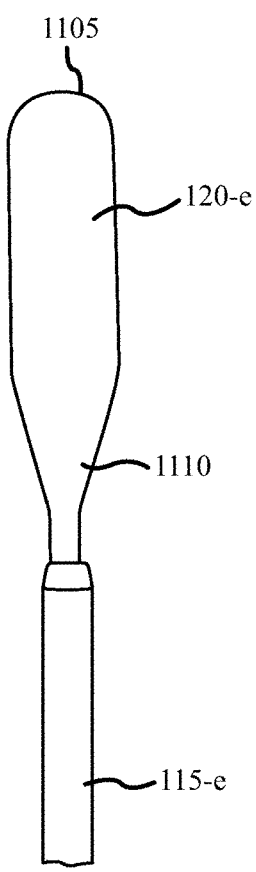

With reference to FIG. 5F, the expandable support device 120-*e* has a particular expanded shape in accordance with various embodiments. In the expanded configuration, expandable support device 120-*e* may have body shaped like a paddle. The expandable support device 120-*e* may have a perimeter with generally parallel sides extending in a longitudinal direction. The expandable support device 120-*e* may include an atraumatic distal end 1105. The distal end 1105 of the expandable support device 120-*e* may be rounded to avoid sharp edges and corners that allow the expandable support device 120-*e* to be moved axially without risking inadvertent perforation or injury of the treatment area. As used herein, the "axial" direction is the direction from the proximal end to the distal end. In various embodiments, the distal end 1105 has a radius of about 0.25 inch. In various embodiments, the distal end 1105 has a radius of about 0.125 inch. The rounded distal end 1105 may meet the side edges at a smooth transition. Thus, at least an outward portion of the periphery of the expandable support device 120-*e* is rounded to reduce of injury or damage. The rounded distal end 1105 may also promote collapsing and insertion of the expandable support device 120-*e* into the working channel 115-*e*.

A proximal end 1110 of the expandable support device 120-*e* may be tapered to promote withdrawal of the expandable support device 120-*e* into the working channel 115-*e*. In particular, the tapered proximal end 1110 provides an angled contact surface for contacting the edges of the working channel 115-*e*. As the expandable support device 120-*e* is withdrawn into the working channel 115-*e*, the walls of the working channel 115-*e* may provide a folding force on the expandable support device 120-*e* to cause the expandable support device 120-*e* to contract to the collapsed configuration. This folding action is similar to a feather withdrawn into a tube. As will be described below, the expandable support device 120-*e* may have a structure and configuration carefully selected to promote and control the collapsing and expanding actions. The proximal end 1110 can also be configured for coupling to the guide shaft 110.

In some embodiments, one side of the expandable support device 120-*e* is textured or otherwise marked at the tapered proximal end 1110 to indicate on which side expandable support device 120-*e* the operative member is disposed. Such texturing or marking can be useful when the expandable support member 120-*e* is transparent and it becomes difficult for a user to distinguish between the sides of the expandable support device 120-*e*. The texturing and marking can also be on an operative member disposed on the expandable support device 120-*e*.

One may appreciate from the description herein, however, that the shape and configuration of the expandable support device 120-*e* may vary depending on the application. For example, the expandable support device 120-*e* may have curved sides or a polygonal-shaped periphery. In various embodiments, the expandable support device 120-*e* is substantially elliptical. The expandable support device 120-*e* may also have different cross-sectional shapes when deployed.

In some embodiments, the expandable support device includes a solid body of elastomeric material. The solid body of elastomeric material can be a molded elastomeric body, including an elastomeric body molded in the shape of a paddle as described above. In some embodiments, the elastomeric material is silicone. The elastomeric body can be transparent, translucent, and/or opaque, for example. A solid elastomeric body can be a suitable material for the expandable support body because of its flexibility and resistance to plastic deformation. The elastomeric material can generally provide the expandable support device with the ability to transition between a collapsed configuration and an expanded configuration, as a generally planar body of elastomeric material can be folded or curved through the application of external force, followed by returning to its planar configuration when the application of external force is removed. The solid elastomeric body used for the expandable support device can have a variety of thicknesses in accordance with various embodiments.

With reference to FIG. 6A, an expandable support device 120-*g* in the shape of a paddle and which can be made from a solid elastomeric body is provided in accordance with various embodiments, and further includes a flexible support 155-*a* coupled with the expandable support device 120-*g*. The flexible support 155-*a* can be provided to add additional structural support to the expandable support device 120-*g* and/or to provide apposition force when the expandable support device 120-*g* is deflected against a target treatment area. Providing additional support to the expandable support device 120-*g* can be useful when the expandable support device 120-*g* is made from a flexible material, such as an elastomeric material. Without a flexible support 155-*a* coupled with an expandable support device 120-*g* made from a solid elastomeric body, the expandable support device 120-*g* may run into problems when being transported through a working channel, such as folding over on itself and creating obstructions within the working channel. When a flexible support 155-*a* is provided, the expandable support device 120-*g* may have suitable structure support so as to maintain the expandable support device 120-*g* in the collapsed configuration while being transported through a working channel.

As shown in FIG. 6A, the flexible support 155-*a* may extend from the proximal end 1110-*a* to the distal end 1105-*a* of the expandable support device 120-*g*. In some embodiments, the flexible support 155-*a* overlaps and is aligned with a central axis extending between the proximal end 1110-*a* and the distal end 1105-*a* of the expandable support device 120-*g*.

The flexible support 155-*a* may be made from a flexible material so that it is capable of bending when the expandable support device 120-*g* is being passed through a non-linear working channel. In some embodiments, the flexible support 155-*a* is made from at least a highly elastic or superelastic material. The superelastic material can be nitinol, for example. The highly elastic material can be spring steel, for example.

Figure 7:
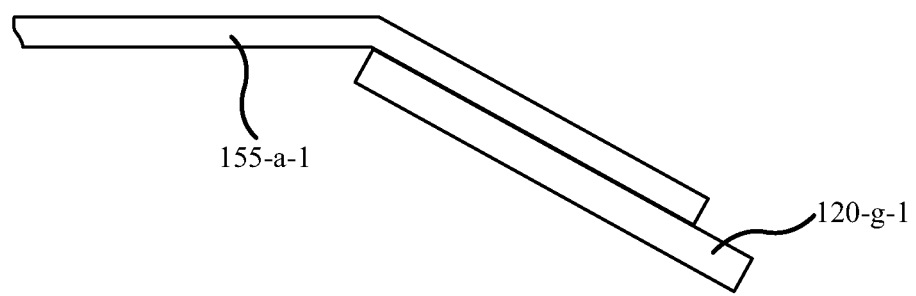
FIG. 7 is a side view of a flexible support coupled with an expandable support device according to various embodiments.
Figure 8:
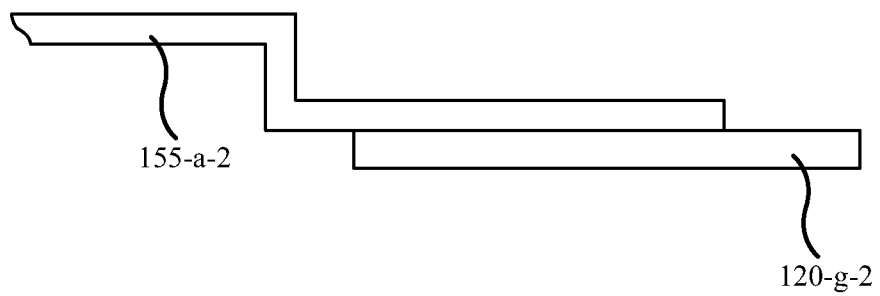
FIG. 8 is a side view of a flexible support coupled with an expandable support device according to various embodiments.

In FIG. 6A, the expandable support device 120-*g* may include a single flexible support 155-*a*, and no further supports may be provided. However, other embodiments may include two or more flexible supports. With reference to FIG. 6B, the expandable support device 120-*h* includes two flexible supports 155-*b*-1, 155-*b*-2 arranged in a "wishbone" configuration in accordance with various embodiments. In this wishbone configuration, the flexible supports 155-*b*-1, 155-*b*-2 may be arranged in parallel to the central axis of the expandable support device 120-*h*, but are located at the peripheral edges of the expandable support device 120-*h*. With reference to FIG. 6C, the expandable support device 120-*i* includes three flexible supports 155-*c*-1, 155-*c*-2, 155-*c*-3 arranged in a "trident" configuration in accordance with various embodiments. In this trident configuration, the flexible supports 155-*c*-1, 155-*c*-3 may be arranged in parallel to the central axis and located at the peripheral edges of the expandable support device 120-*i*, while support 155-*c*-2 is aligned with and overlaps the central axis of the expandable support device 120-*i*. As shown in FIGS. 7 and 8, the peripherally located flexible supports can include taper sections that follow the taper of the expandable support device at the proximal end. While FIGS. 6A-C show using from one to three flexible supports, any number of flexible supports can be used. Additionally, the flexible supports can be linear or longitudinal supports. Other embodiments may utilize other configurations, including open and/or closed configurations.

In some embodiments where more than one flexible support is provided, the flexible supports can be made from different materials. For example, in the trident configuration shown in FIG. 6C, the flexible support 155-*c*-2 located along the central axis can be made from nitinol, while the peripherally located flexible supports 155-*c*-1, 155-*c*-3 can be made from a different material, such as polyimide. The thickness of each flexible support can also be variable, such as when peripherally located flexible supports 155-*c*-1, 155-*c*-3 are thinner than the flexible support 155-*c*-2 located along the central axis.

With reference to FIG. 6A, a protective padding 1245 can encompass the distal tip of the flexible support 155-*a*. When multiple flexible supports are used, a protective padding can encompass some or all of the flexible supports. With reference to FIG. 6B, protective paddings 1245-*a*-1 and 1245-*a*-2 encompass the distal tips of flexible supports 155-*b*-1 and 155-*b*-2. With reference to FIG. 6C, protective paddings 1245-*b*-1, 1245-*b*-2, 1245-*b*-3 encompass the distal tips of flexible supports 155-*c*-1, 155-*c*-2, 155-*c*-3. The protective padding can be provided to prevent the distal tips of the flexible supports from damaging the target treatment area. In some embodiment, the protective padding comprises silicone layered above and below the distal tips.

In some embodiments, the flexible supports are configured as straight flexible supports, with no bends, curves, or the like. In other words, the flexible supports may be aligned generally in parallel to the guide assembly. With reference to FIGS. 7 and 8, some embodiments of the flexible support include one or more bends. As shown in FIG. 7, the flexible support 155-*a*-1 may be angled in a downward direction such that the expandable support device 120-*g*-1 coupled with the flexible support 155-*a*-1 is also positioned at an angle. As shown in FIG. 8, the flexible support 155-*a*-2 may include two approximately right angle bends so that the flexible support 155-*a*-2 has two parallel sections on different planes. The expandable support device 120-*g*-2 can be coupled with the portion of the flexible support 155-*a*-2 that is on different plane from the portion of the flexible support 155-*a*-2 extending out of a working channel. Other configurations are also possible. Generally speaking, the non-linear flexible support can be provided to improve contact between the operative member disposed thereon and the target treatment area.

Any manner of coupling the flexible supports to the expandable support device can be used. In some embodiments, the flexible supports are coupled the expandable support device using a silicone adhesive. With reference to FIG. 9A, FIG. 9B, and/or FIG. 9C, the flexible supports 155-*d*, 155-*e*-1, 155-*e*-2, 155-*f*-1, 155-*f*-2, 155-*f*-3 can be coupled with their respective expandable support device 120-*j*, 120-*k*, 120-*l* such that the flexible supports are positioned outside of their respective expandable support device 120-*j*, 120-*k*, 120-*l*. With reference to FIG. 10A, FIG. 10B, and/or FIG. 10C, the flexible supports 155-*g*, 155-*h*-1, 155-*h*-2, 155-*i*-1, 155-*i*-2, 155-*i*-3 can be coupled with their respective expandable support device 120-*m*, 120-*n*, 120-*o* such that they are partially embedded within their respective expandable support device 120-*m*, 120-*n*, 120-*o*. The expandable support devices 120-*m*, 120-*n*, and 120-*o* can be overmolded with primer for adhesion to the respective flexible supports 155-*g*, 155-*h*-1, 155-*h*-2, 155-*i*-1, 155-*i*-2, 155-*i*-3.

In various embodiments, the expandable support device includes a solid substrate in which portions of the solid substrate are selectively removed from the substrate to form a pattern of splines and voids. The pattern formed in the solid substrate can be specifically designed to control the bending or folding of the patterned solid substrate. Removing portions of the solid substrate can generally result in the solid substrate having less strength and folding more easily. In other words, the pattern formed in the solid substrate can influence the bending strength or rigidity of the solid substrate. The pattern may be selected to provide different bending strength in localized regions of the patterned solid substrate. For example, the pattern may be selected to provide greater rigidity along a central region and relatively less bending rigidity along longitudinal outer edges. The resulting patterned solid substrate can be self-expanding. An expansion force such as a balloon inflation force is generally not necessary to expand the solid substrate. In various embodiments, the solid support self-expands to a predetermined shape.

The selective removal of material and the specific pattern selected can adjust the expansion force of the solid substrate within a specific range to optimize expansion while allowing collapsing back into a collapsed configuration. In some embodiments, the width and spacing of the splines formed by patterning impacts the ability of the solid substrate to transition between the collapsed and expanded configuration.

In some embodiments, the solid substrate begins as a plate of solid substrate material, after which the plate is shaped and patterned to provide the final patterned solid substrate suitable for use as a part of the expandable support device. In some embodiments, the plate has a uniform thickness in the range of from 0.002 to 0.004 inch. In various embodiments, the plate has a variable thickness or is patterned to have a variable thickness (i.e., patterned to have splines of varying thickness). The solid substrate may be thin such that the thickness is orders of magnitude smaller than the width and height.

The solid substrate patterned to include multiple splines and voids can be used alone as the expandable substrate device, or can be used in conjunction with the solid elastomeric body described in greater detail above. When the patterned substrate is used alone for the expandable support device, an operative member can be disposed directly on the patterned substrate. When used in conjunction with the solid elastomeric body described above, the patterned substrate can be disposed on and coupled with a surface of the solid elastomeric body.

In some embodiments, the patterned solid substrate is disposed on a surface of the solid elastomeric body opposite the surface of the solid elastomeric body on which the operative member is disposed. In some embodiments, the patterned solid substrate is disposed on a surface of the solid elastomeric body, and the operative member is disposed on the patterned solid substrate such that the patterned solid substrate is intermediate the solid elastomeric body and the operative member. When the patterned solid substrate is used in conjunction with the solid elastomeric body, the patterned solid substrate can generally have a perimeter shape similar or identical to the perimeter shape of the solid elastomeric body. For example, when the solid elastomeric body has a paddle shape, the patterned solid substrate can also have a paddle shape. The patterned solid substrate shaped like a paddle can have similar features as the paddle-shaped solid elastomeric body, such as a rounded distal tip and a tapered proximal end. The perimeter of the patterned solid substrate can be interior to the perimeter of the solid elastomeric body, coextensive with the perimeter of the solid elastomeric body, or portions or all of the patterned solid substrate can be exterior to the perimeter of the solid elastomeric body.

Figure 11A:
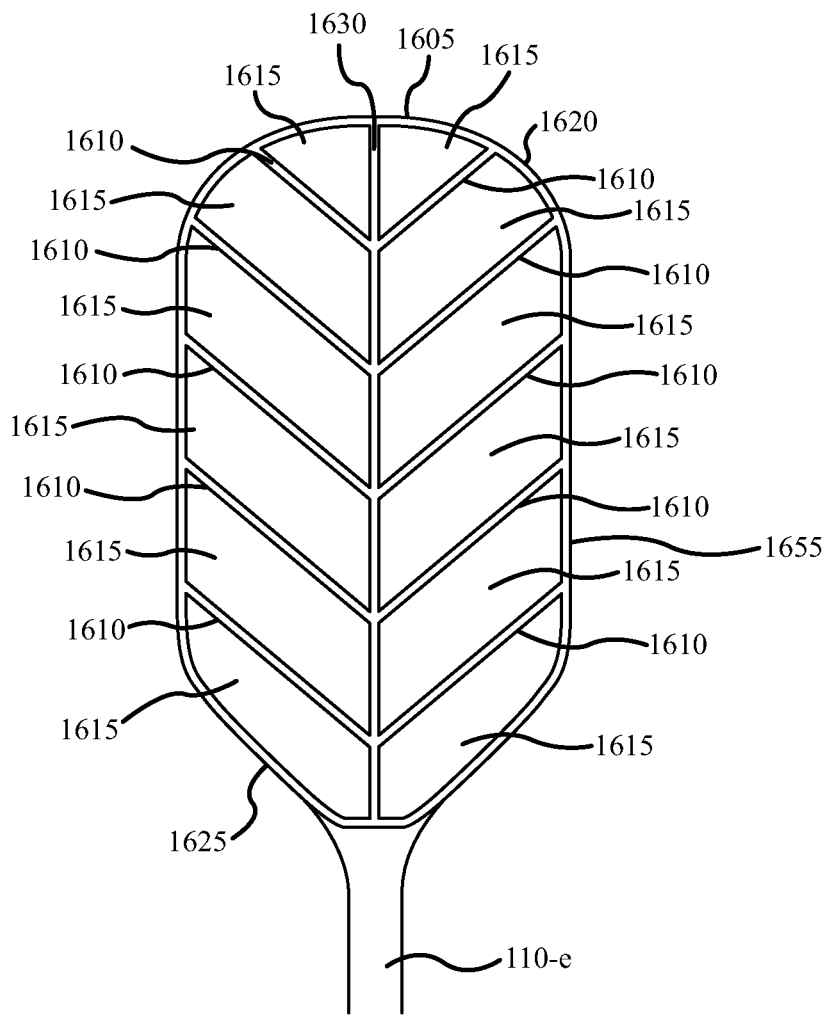
FIG. 11A is a plan view of a patterned solid substrate according to various embodiments.

With reference to FIG. 11A, a patterned solid substrate 1605 having portions of the patterned solid substrate 1605 removed to form splines 1610 and voids 1615 is shown in accordance with various embodiments. The patterned solid substrate 1605 can include a distal end 1620, a proximal end 1625, and a central axis extending from the proximal end 1625 to the distal end 1620 of the patterned solid substrate 1605.

The pattern of splines 1610 and voids 1615 can include any pattern that provides support to an operative member and promotes expansion between an expanded configuration and a collapsed configuration. In FIG. 11A, the patterned solid substrate 1605 is shown in an expanded configuration in accordance with various embodiments, which can generally include providing a substantially planar, curviplanar surface, or surface that conforms to the target treatment area surface.

In various embodiments, including the embodiment shown in FIG. 11A, the patterned solid substrate 1605 includes a central axis spline 1630 that substantially overlaps the central axis of the patterned solid substrate 1605. The central axis spline 1630 can be coupled with the guide assembly 110-e at the proximal end 1625 of the patterned solid substrate 1605. In some embodiments, the guide assembly 110-e and the central axis spline 1630 are a unitary piece. The patterned solid substrate 1605 can also be patterned so as to include an outer perimeter portion 1655 that defines and extends around the outer perimeter of the patterned solid substrate 1605.

In some embodiments, the patterned solid substrate 1605 is patterned such that a first subset of splines and a second subset of splines are formed. The first subset of splines can be arranged parallel with one another and can extend from the central axis spline towards a first lateral peripheral edge of the patterned solid substrate 1605. The second subset of splines can be arranged parallel to one another and can extend from the central axis spline 1630 towards a second lateral peripheral edge of the patterned solid substrate 1605, the second lateral peripheral edge being opposite the first lateral peripheral edge. In some embodiments, the width and/or thickness of the first subset of splines and the second subset of splines is less than the width and/or thickness of the central axis spline 1630. In some embodiments, the first subset of splines and the second subset of splines extend away from the central axis spline 1630 until they each connect with the outer perimeter portion 1655 of the patterned solid substrate 1605.

In some embodiments, both the first subset of splines and the second subset of splines extend away from the central axis spline 1630 and towards the distal end 1620 of the patterned solid substrate 1605. In this manner, the first subset of splines and the second subset of splines extend away from the central axis spline 1630 at an angle, which can range from greater than 0 degrees (which would be close to parallel with the central axis spline 1630) to 90 degrees (which would be perpendicular to the central axis spline 1630). In some embodiments, the angle of the first subset of splines is the same as the angle of the second subset of splines, while in other embodiments, the angle of the first subset of splines is different from the angle of the second subset of splines. In some embodiments, the angle of the first subset of splines and the second subset of splines is about 45 degrees. When the first subset of splines and the second subset of splines protrude away from the central axis spline 1630 towards the distal end 1620, this can help promote the transition of the patterned solid substrate 1605 between the expanded configuration and the collapsed configuration when the patterned solid substrate 1605 is being drawn back into a working channel. This spline pattern can behave similar to a feather being drawn back into a tube.

Figure 11B:
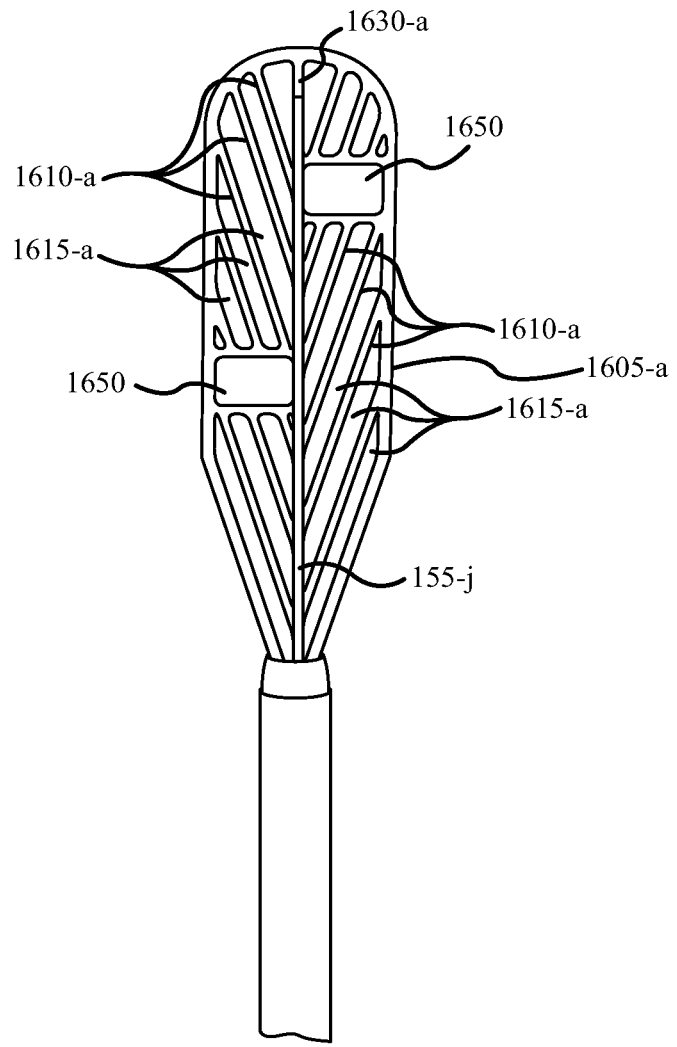
FIG. 11B is a plan view of a patterned solid substrate according to various embodiments.

FIG. 11B illustrates a patterned solid substrate 1605-a in accordance with various embodiments that may be an example of the patterned solid substrate 1605 shown in FIG. 11A. The patterned solid substrate 1605-a may include a central axis spline 1630-a, multiple splines 1610-a and multiple voids 1615-a. The multiple splines 1610-a can be divided up into a first subset of splines and a second subset of splines as described above with reference to FIG. 11A. The patterned solid substrate 1605-a can also include a flexible support 155-j as described in greater detail above with respect to FIGS. 6-8. The flexible support 155-j, which can be made of nitinol, for example, can be located on either surface of the patterned solid support 1605-a. In some embodiments where the patterned solid support 1605-a is used with a solid elastomeric body, the solid elastomeric body can be located between the patterned solid support 1605-a and the flexible support 155-j.

The patterned solid support 1605-a can also include vias 1650. The vias 1650 can be provided for coupling an operative member disposed on one side of the patterned solid substrate 1605-a to buses located on the opposite side of the solid patterned substrate 1605-a. Any number of vias 1650 can be provided, and the vias 1650 can be located anywhere throughout the patterned solid substrate 1605-a. As shown in FIG. 11B, the vias 1650 can interrupt the pattern of the patterned solid substrate 1605-a.

Other patterns in the patterned solid substrate can also be used. In various embodiments, the pattern is a repeating pattern. The pattern may be formed of a repeating shape or shapes. For example, the pattern may be a repeating diamond, triangle, or square. The pattern may be a repeating polygonal shape of three, four, or more sides. In various embodiments, the pattern is formed of two or more different patterns in different regions. For example, outer edges of the patterned solid substrate may have a different pattern than the inner, central region. The patterns may be similarly shaped but formed of splines with different dimensions and spacing. As with the pattern shown in FIGS. 11A and 11B, these other patterns can affect the properties of patterned solid substrate, such as the expansion force of the patterned solid substrate.

Figure 12A:
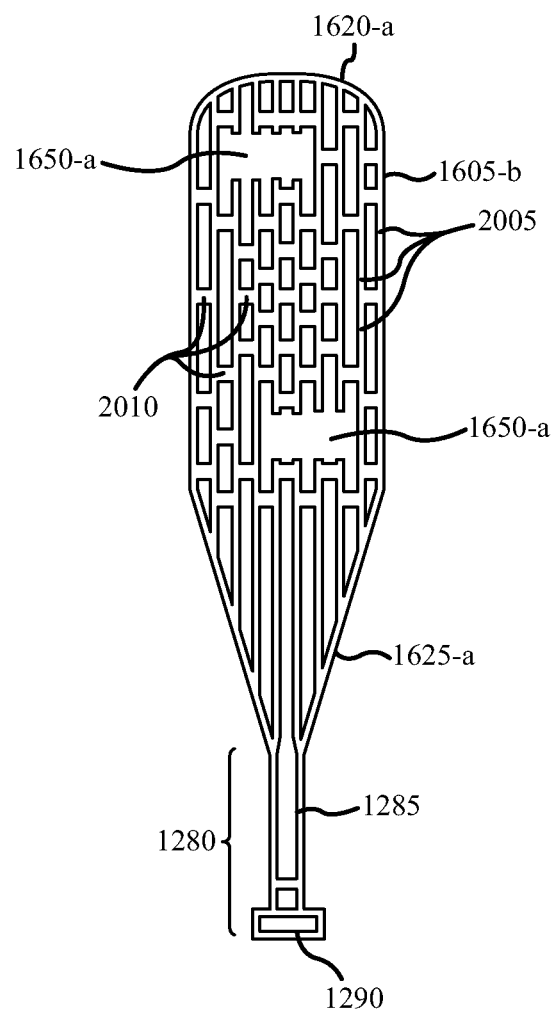
FIGS. 12A-12B are plan views of a patterned solid substrate according to various embodiments.
Figure 12B:
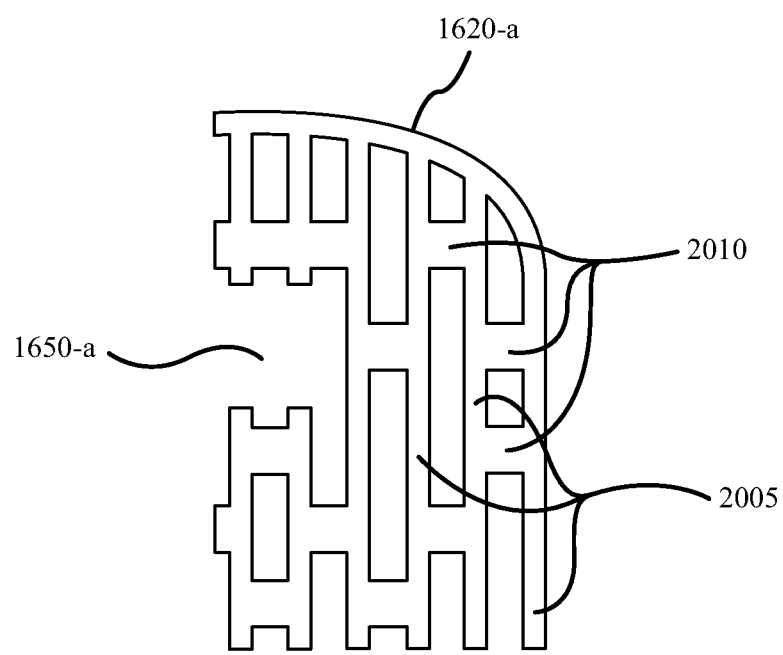

With reference to FIG. 12A and/or FIG. 12B, an alternate pattern can include a criss-cross pattern with vertical splines 2005 and horizontal splines 2010, where the vertical direction generally includes from the proximal end 1625-a to the distal end 1620-a and substantially parallel to the central axis in accordance with various embodiments. The horizontal splines 2010 can be orthogonal or perpendicular to the vertical splines 2005. The vertical splines 2005 and horizontal splines 2010 can have substantially the same width. The vertical splines 2005 can be elongated from the proximal end 1625-a to the distal end 1620-a of the patterned solid support 1605-b. The horizontal splines 2010 can extend a short distance, typically between adjacent vertical splines 2005. The horizontal 2010 can be offset from each other with non-uniform spacing in an axial direction. Adjacent vertical splines 2005 can be spaced an equidistant amount. The patterned solid substrate 1605-b can also include one or more vias 1650-a at various locations, which may disrupt the pattern. Such a pattern of relatively long vertical splines 2005 with regular spacing can promote the folding or rolling action of the patterned solid substrate 1605-*b*. In a transverse direction, by contrast, the patterned solid substrate can be relatively rigid. Such rigidity can improve maneuverability and improve apposition force.

Figures 13E, 13F:
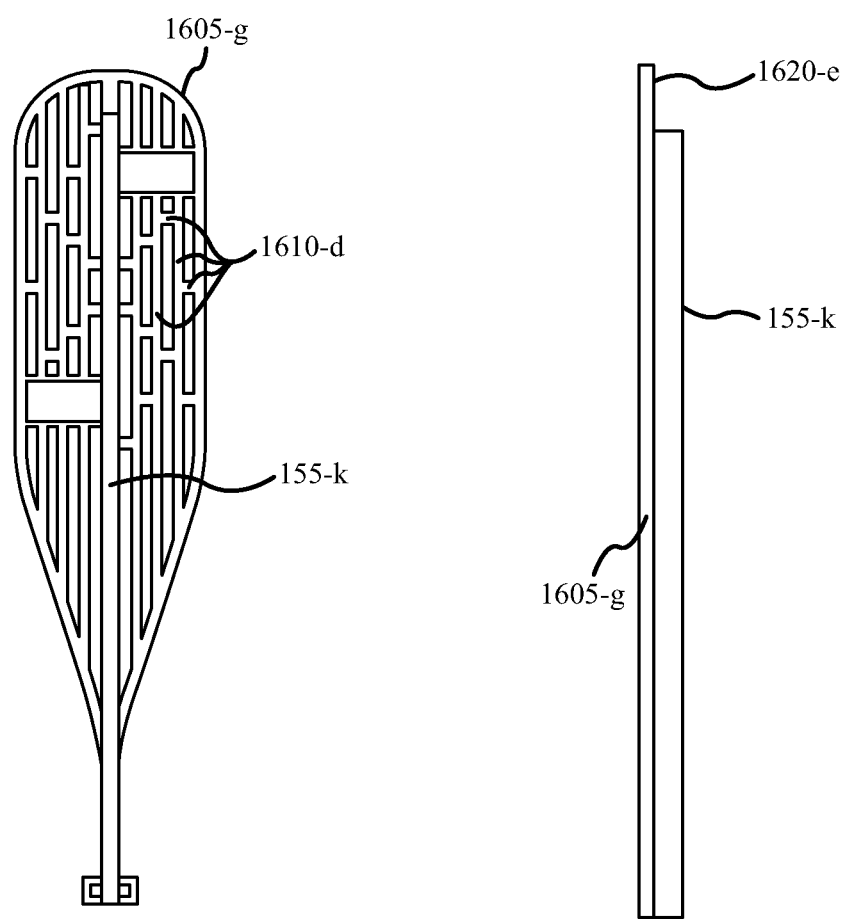

FIGS. 13A to 13L illustrate various alternative patterns suitable for use in the patterned solid substrate in accordance with various embodiments. FIG. 13A illustrates a patterned solid substrate 1605-*c* with a pattern of orthogonal splines that may be similar in various respects to the pattern shown in FIGS. 12A and 12B in accordance with various embodiments. The pattern may include vertically-extending splines 2005-*a* spaced from each other and horizontally-extending splines 2010-*a*. The spacing between the splines may vary. In some embodiments, the spacing between adjacent vertical splines 2005-*a* along the outer edges is greater than the spacing between adjacent splines in the interior of the pattern. This may be useful to increase the elasticity of the patterned solid substrate 1605-*c* along the outer edges. The width of each of the splines may vary across the patterned solid substrate 1605-*c*.

FIG. 13B illustrates a pattern of cross-hatched splines 1610-*b* in accordance with various embodiments. The pattern depicted in FIG. 13B may be similar in various respects to the pattern shown in FIGS. 12A and 12B, except that the pattern may be skewed in accordance with various embodiments. The pattern need not repeat across the entire body of the patterned solid substrate 1605-*d*. The pattern can repeat along distal end 1620-*b* of the patterned solid substrate 1605-*d*. Along an intermediate section, the pattern can be relatively random. One of the series of splines can be incomplete. The pattern can begin to repeat again along the proximal end 1625-*b* of the patterned solid substrate 1605-*d*.

FIG. 13C illustrates a patterned solid substrate 1605-*e* wherein there can be two different repeating patterns of shapes in accordance with various embodiments. The distal end 1620-*c* may include a repeating pattern of squares and octagons. The proximal end 1625-*c* may have a honeycomb-shaped pattern of hexagons.

FIG. 13D illustrates a patterned solid substrate 1605-*f* having a combination of various patterns in accordance with various embodiments. A distal end 1620-*d* can include multiple wavy splines 1610-*c*-1 generally pointed in a common direction, for example, a vertical direction. An intermediate section can have a splines 1610-*c*-2 in a checkered pattern. A proximal section 1625-*d* can have a pattern of different splines 1610-*c*-3. Some of the splines 1610-*c*-3 can be straight, some can be wavy, and some can have jagged shapes.

FIG. 13E and/or FIG. 13F illustrate a patterned solid support 1605-*g* with a pattern of splines 1610-*d* in accordance with various embodiments, which may be similar to the pattern shown in FIGS. 12A and 12B. The splines 1610-*d* can be formed into vertical sections and horizontal sections. The horizontal sections can be staggered and have varying lengths. The lengths can be defined by the spacing between vertical spline sections. A spacing between adjacent vertical spline sections can be about 0.016 inch, for example. A width of each of the vertical and horizontal spline sections can be about 0.016 inch. An exception can be the spline sections defining a border of cut-outs. These splines sections can be about 0.008 inch.

The patterned solid substrate 1605-*g* can be integrally formed with a central axis flexible support 155-*k*. The central axis flexible support 155-*k* can be configured as a backbone that extends along and is aligned with the central axis of the patterned solid substrate 1605-*g*. The central axis flexible support 155-*k* can have a width and/or thickness larger than a width and/or thickness of the splines 1610-*d*. The patterned solid substrate 1605-*g* can overhang the central axis flexible support 155-*k* at a distal end 1620-*e*.

Figures 13G, 13H:
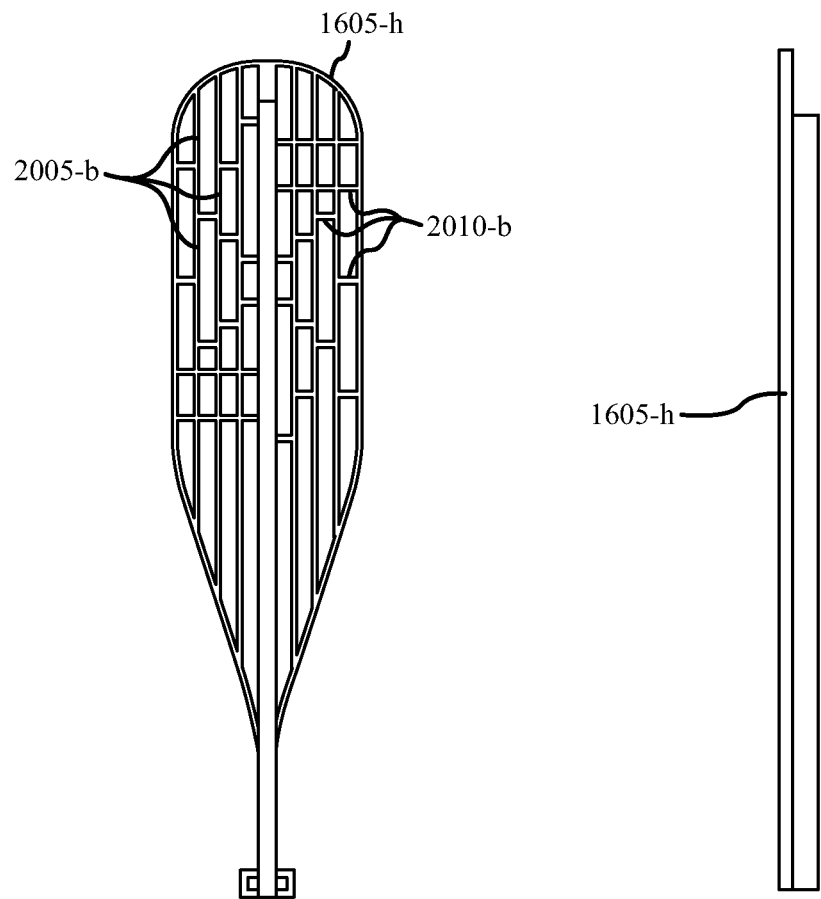

FIG. 13G and/or FIG. 13H illustrate a patterned solid substrate 1605-*h*, which may be similar to the pattern shown in FIGS. 12A and 12B, in accordance with various embodiments. The patterned solid substrate 1605-*h* can have relatively narrower horizontal splines 2005-*b*, such as, for example, a width of about 0.008 inch. As described herein, the horizontal splines 2010-*b* can play a role in the expanding and collapsing of the patterned solid substrate 1605-*h*. In part, the vertical splines 2005-*b* may roll around each other like a flag whereas the horizontal splines 2010-*b* generally bend. The narrower spline sections thus can result in a patterned solid substrate 1605-*h* with a lower expansion/collapsing force. This can make the patterned solid substrate 1605-*h* easier to retract into the working channel while also lowering the force for expansion.

Figure 13I:
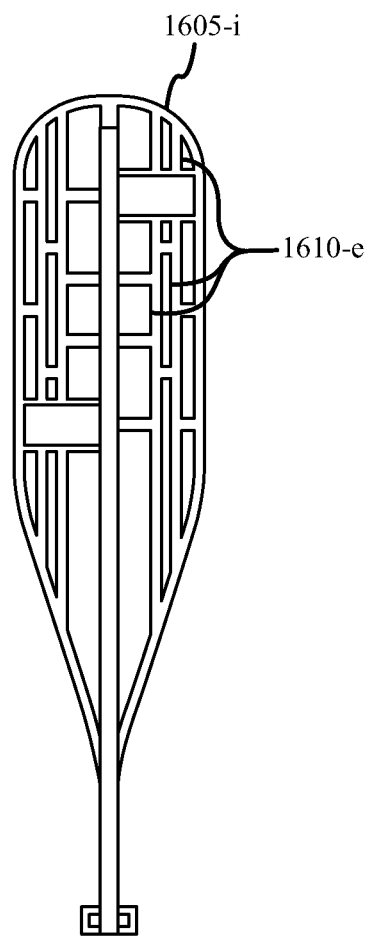
Figure 13J:
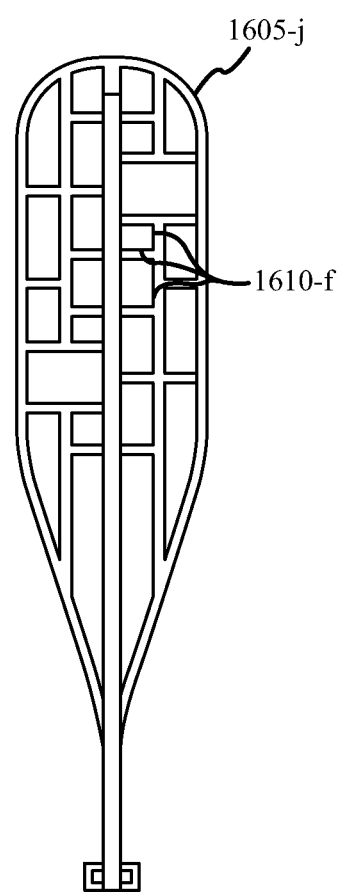
Figure 13K:
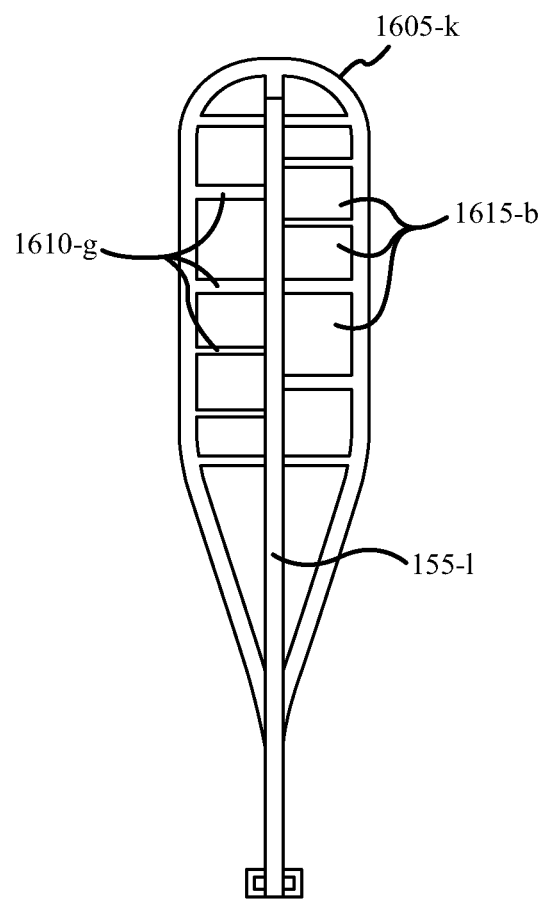

FIG. 13I, FIG. 13J, and/or FIG. 13K illustrate patterns with various spline spacings and alternative void dimensions in accordance with various embodiments. The patterns may be otherwise similar to the pattern shown in FIGS. 12A and 12B.

FIG. 13I illustrates a patterned solid substrate 1605-*i* having a pattern with multiple splines 1610-*e* arranged vertically and horizontally in accordance with various embodiments. By contrast to some of the spline patterns described above, the horizontal sections adjacent the central axis can be relatively longer thereby providing wider voids. This configuration can result in a lower bending force required adjacent the central axis than along the outer edges of the patterned solid support 1605-*i*. In operation, the patterned solid substrate 1605-*i* tends to fold into a U-shape.

FIG. 13J illustrates a patterned solid substrate 1605-*j* having a pattern with multiple splines 1610-*f* arranged vertically and horizontally in accordance with various embodiments. By contrast to some of the spline patterns described above, the pattern has can have relatively large voids. The larger voids can result in a weaker patterned solid substrate 1605-*j*, and by the same token, a lower expansion force. The relatively uniform distribution and size of the voids can lead to relatively uniform bending.

Figure 13L:
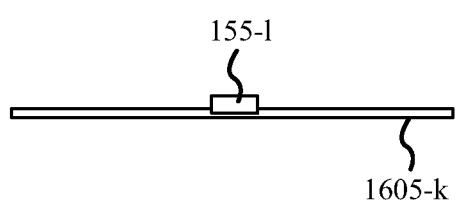

FIG. 13K and/or FIG. 13L illustrate a patterned solid substrate 1605-*k* having a pattern, which may be similar to the pattern shown in FIGS. 12A and 12B, in accordance with various embodiments. FIG. 13L may provide a top end view of the patterned solid substrate 1605-*k* illustrating a central axis flexible support 155-*l* positioning relative to the patterned solid substrate 1605-*k* in the deployed configuration. The patterned solid substrate 1605-*k* may include multiple splines 1610-*g* arranged vertically and horizontally. The pattern of splines 1610-*g* may define voids 1615-*b* with rectangular shapes. The voids 1615-*b* may generally have a shorter height than width. By the same token, a space between adjacent horizontal spline sections may generally be smaller than the length of the vertical spline sections. The patterned solid substrate 1605-*k* can also include a several horizontal spline sections that extend across the entire width of the patterned solid substrate 1605-*k*. The horizontal sections can be interrupted by a central axis flexible support 155-*l*.

The pattern shown can have a lower spline density than some of the previously described patterns. The spline density may refer to a ratio of the area of the splines to an area of the voids in a given section. Put another way, the spline density may refer to the material remaining relative to the amount of material removed to form the voids.

In any of the patterns used, including those described above, the dimensions of the splines and voids can vary greatly to produce varying effects on the ability to transition the patterned solid substrate between a collapsed configuration and an expanded configuration. The overall dimensions of the patterned solid substrate can also impact the collapsing and expanding of the patterned solid substrate.

In various embodiments, the width of the patterned solid substrate is about 7 mm. In various embodiments, the width of the patterned solid substrate is about 3 mm, about 4 mm, about 5 mm, about 6 mm, about 7 mm, about 8 mm, about 9 mm, or more than 10 mm. In various embodiments, the patterned solid substrate has a width of about 0.2 inch, 0.27 inch, or 0.276 inch. Other embodiments may include other widths of the pattern solid substrate.

In various embodiments, the splines may be about 0.015 inch in width. The width of the splines may be based on the thickness of the patterned solid substrate. For example, the width of the splines may be proportional to the thickness of the patterned solid substrate. In various embodiments, a width of the splines is between about 0.008 inch and about 0.02 inch, between about 0.008 inch and about 0.015 inch, between about 0.01 inch and about 0.02 inch, or between about 0.01 inch and about 0.015 inch. Other embodiments may include other widths of the splines.

In various embodiments where the pattern includes vertical and horizontal splines, the patterned solid substrate includes vertical splines having a width of about 0.008 inch, about 0.01 inch, about 0.012 inch, about 0.015 inch, about 0.016 inch, about 0.02 inch, or about 0.03 inch, and horizontal splines having a width of about 0.008 inch, about 0.01 inch, about 0.012 inch, about 0.015 inch, about 0.016 inch, about 0.02 inch, or about 0.03 inch. In various embodiments, the patterned solid substrate includes vertical splines having a width of about 0.03 inch and horizontal splines having a width of about 0.01 inch, 0.02 inch, or a combination thereof. In various embodiments, the patterned solid substrate includes vertical splines having a width of about 0.016 inch and horizontal splines having a width of about 0.01 inch, about 0.016 inch, about 0.02 inch, or a combination thereof. In various embodiments, the patterned solid substrate includes vertical splines having a width of about 0.016 inch and horizontal splines having a width of about 0.012 inch. In various embodiments, the patterned solid substrate includes vertical splines and horizontal splines having widths of about 0.016 inch. In various embodiments, the patterned solid substrate includes splines having widths ranging from about 0.01 inch to about 0.03 inch. In various embodiments, the patterned solid substrate includes vertical splines and horizontal splines having widths of about 0.008 inch. Other embodiments may include other widths of the splines.

In various embodiments, a spacing (void width) between adjacent vertical splines is about 0.016 inch, about 0.024 inch, greater than 0.03 inch, or greater than 0.04 inch. In various embodiments, a spacing between adjacent horizontal splines (void length) is about 0.016 inch, about 0.024 inch, greater than 0.05 inch, greater than 0.1 inch, greater than 0.2 inch, or greater than 0.3 inch. As explained herein, the pattern may include splines in an angled orientation whereby the splines are not horizontal or vertical. In various embodiments, a spacing between adjacent splines is about 0.016 inch, about 0.024 inch, greater than 0.05 inch, greater than 0.1 inch, greater than 0.2 inch, or greater than 0.3 inch. Other embodiments may include other widths of the voids.

The patterned solid substrate can be formed of a material having at least highly elastic or superelastic properties, shape memory properties, or both. In various embodiments, the patterned solid substrate is formed of a superelastic material (SEM). In various embodiments, the patterned solid substrate is formed of a shape memory metal or shape memory alloy (SMA). Suitable materials for the patterned solid substrate may include, but are not limited to, nickel-titanium, copper-aluminum-nickel, copper-zinc-aluminum, iron-manganese-silicon, and alloys of the same. The patterned solid substrate may also be formed of other materials. In some embodiments, the patterned solid substrate is formed of material having highly elastic material, including, but not limited to, spring steel. In some embodiments, highly elastic material includes material having a yield strength in the range of from about 400 MPa to about 1100 MPa.

In some cases the material of the patterned solid substrate is selected based on the application. For example, if the patterned solid substrate may need to collapse to a larger degree and thus may experience large strains, nitinol may be more suitable than spring steel. One may appreciate from the description herein, however, that a number of factors affect the amount of strain experienced by the component such as the shape, the spline pattern, and the interaction with other components.

Superelastic materials typically permit large elastic (recoverable) deformations. For example, SEMs may withstand 22.5% deformation with high damping under loads in the kN/mm range for solid wires and about 10 to about 100 N/mm for tubes with an outer diameter of 0.4-2 mm. Recoverable deformations as great as 60% or more have been observed with thin-walled SEM tubes. This phenomenon is sometimes referred to as "giant superelasticity effect" (GSE). In various embodiments, the patterned solid substrate 1605 is formed of a SEM. In various embodiments, the patterned solid substrate 1605 is formed of a material having GSE properties.

In some embodiments, the patterned solid substrate is formed of nickel-titanium. Nickel-titanium is often referred to as nitinol (i.e., Nickel-Titanium Naval Ordinance Laboratory). Nickel-titanium is known to have both shape memory and superelastic properties. A nickel-titanium alloy is sometimes made from a nearly equal composition of nickel and titanium. The performance of nitinol alloys are generally based on the phase transformation in the crystalline structure, which transitions between an austenitic phase and a martensitic phase. The austenitic phase is generally called the high temperature phase, and the martensitic phase is called the low temperature phase. In the martensitic phase the material has a relatively low tensile strength and is stable at relatively low temperatures. In the austenitic phase, the material generally has a relatively high tensile strength and is stable at temperatures higher than the martensitic phase. The phase transformation is the general mechanism by which superelasticity and the shape memory effect are achieved.

Shape memory generally implies that the alloy can be inelastically deformed into a particular shape in the martensitic phase, and when heated to the austenitic phase, the alloy transforms back to the particular shape. Thus, at elevated temperatures the material can experience recoverable strains. For typical nitinol, the transformation temperature (Af) may be about 50° Celsius. The Af temperature may vary depending on the application. In various embodiments, the Af temperature of the support member is selected to be about 15° C. In various embodiments, the Af temperature of the support member is selected to below 20° C. Methods for adjusting the transformation temperature of nitinol are generally known as exemplified by U.S. Pat. No. 4,283,233 to Goldstein et al, incorporated by reference for all purposes.

Superelasticity or pseudoelasticity generally refers to the relatively high elasticity of the alloy when placed under stress and without the involvement of heat. For example, it is possible to see reversible strains of 8 percent or more elongation in a superelastic nitinol wire as compared to 0.5 percent reversible strain in a comparable steel wire, for example. The superelastic property may appear in the austenitic phase when stress is applied to the alloy and the alloy changes from the austenitic phase to the martensitic phase. This particular martensitic phase may more precisely be known as stress-induced martensite (SIM). The phase is generally unstable at temperatures above the phase transformation temperature and below the temperature known as Md. At temperatures above Md, stress-induced martensite cannot be achieved and the superelastic properties are lost. Within this temperature range, however, the stress-induced martensite may revert back to the austenitic phase after the force is removed. This phase change may enable the recoverable strains characteristic of nitinol.

When stress is applied to a specimen of a metal having superelastic characteristics (at or above the transformation temperature), the specimen generally deforms elastically until it reaches a particular stress level where the alloy then undergoes SIM. As the phase transformation progresses, the alloy may undergo significant increases in strain with little or no corresponding increases in stress until the transformation of the austenitic phase to the martensitic phase is complete. Thus, the metal generally first deforms elastically and then plastically deforms.

In various embodiments, the patterned solid substrate is formed of a shape memory material. In various embodiments, the patterned solid substrate is entirely formed of a shape memory material. In various embodiments, the patterned solid substrate is formed of a material having superelastic properties. In various embodiments, the patterned solid substrate is entirely formed of a material having superelastic properties. In various embodiments, the patterned solid substrate is formed of nitinol. One may appreciate that other superelastic and/or shape memory materials may be used in accordance with various embodiments of the inventions. The patterned solid substrate may make use of the superelastic properties, shape memory properties, or both properties of the shape memory material.

In various embodiments, the patterned solid substrate is formed of a shape memory alloy and makes use of the material's unique properties. The shape memory effect may allow the patterned solid substrate to be deformed into the collapsed configuration to facilitate its insertion into a working channel. Thereafter, the patterned solid substrate may be heated within the working channel so that the patterned solid substrate is biased towards a predetermined collapsed shape. The predetermined shape may be a specific shape as described above.

In various embodiments, the patterned solid substrate is designed to make use of the superelastic properties of the shape memory alloy so it is disposed to expand and collapse within the working channel. The superelastic property may allow the patterned solid substrate to expand against a tissue surface.

In some embodiments, patterned solid substrate is formed from a nitinol plate having a thickness of 0.003 inch. When the support member is collapsed into a working channel, for example a 2.8 mm working channel, the patterned solid substrate may undergo about 3% to about 4% strain, for example. With conventional materials the patterned solid substrate may plastically deform under these conditions. With nitinol, however, it has been found that the material can undergo about 6% to about 8% strain, for example, without plastic deformation. Thus, the patterned solid substrate can easily fit within the working channel without plastic deformation.

In various embodiments, patterned solid substrate is formed of a shape memory alloy and configured to maintain the operative member in at least one of the expanded configuration and the collapsed configuration.

Patterned solid substrate may make use of shape memory properties in other ways. In various embodiments, the patterned solid substrate is formed of a shape memory material with an initial transition temperature (Af) selected to permit the patterned solid substrate to easily roll into the working channel during preparation and expand to a preset shape once exposed to the internal body temperature. For example, the Af temperature may be between room temperature and normal body temperature. In other words, the material may be designed to be in the austenitic phase between room temperature and body temperature. In various embodiments, the Af temperature is between about 23° C. and about 37° C., between about 25° C. and about 37° C., between about 25° C. and about 40° C., between about 25° C. and about 45° C., between about 15° C. and about 45° C., between about 20° C. and about 35° C., between about 15° C. and about 20° C., or between about 20° C. and about 30° C. Thus, the patterned solid substrate Af temperature may be selected so the patterned solid substrate temperature rises in the body at which point it wants to unroll into an expanded configuration. This process could also be aided by the user flushing the patterned solid substrate with cold water to maintain the temperature below 25° C. and flushing the patterned solid substrate with hot water when it is desired to activate expansion.

An expandable support device, such as any of the expandable support devices described above, can be configured to support an operative member. The operative member can be disposed on an outward facing surface of the expandable support device. The operative member can include any operative member configured for providing therapy to a target treatment area. In some embodiments, the operative member is configured for delivering energy including, but not limited to, radiofrequency (RF) energy, thermal energy, and electromagnetic energy. In various embodiments, the operative member is configured for delivering a heated or cooled fluid or cryogenic fluid. In various embodiments, the operative member is configured for laser treatment, microwave treatment, radio frequency ablation, ultrasonic ablation, photodynamic therapy using photo sensitizing drugs, argon plasma coagulation, cryotherapy, and/or x-ray treatment.

In some embodiments, the operative member is also configured for transitioning between a collapsed and expanded configuration such that the operative member can collapse and expand with the expandable support device on which it is disposed. In some embodiments, the operative member is flexible in order to accommodate this transition. In some embodiments, flexible operative member provides negligible resistance to movement of the expandable support device on which it is disposed.

Other features of the operative member can also be designed to assist the operative member in transitioning between a collapsed and expanded configuration, such as the design of electrodes which can be part of an operative member. In some embodiments, electrodes included as part of the operative member are made from a malleable metal that resists changes to shape but which is capable of bending to a certain extent without plastic deformation. If the malleable metal of the electrodes is too rigid, it will affect, and in some cases prevent, the collapsing and expanding movement. Another approach for making the operative member flexible and conducive to transitioning between a collapsed and expanded configuration can be to design the operative member to decrease the resistance to bending in the desired direction. For example, an operative member including multiple electrodes can include electrodes oriented in a direction parallel to the axis along which the bending of the operative member occurs during transition between collapsing and expanding configurations so that the electrodes generally do not bend as the operative member furls into the collapsed configuration.

In the case of therapy using radiofrequency energy, for example, the operative member may include an electrode or electrode array connected to an energy source configured as a radiofrequency generator. The RF generator can be connected using a coupling and connection line suited to the transmission of electrical energy to the electrode array. The electrode array may be configured as at least a monopolar or bipolar array of electrodes. In the case of therapy using microwave energy, for example, the operative member can include an appropriate antenna or array connected to an energy source configured as a source of microwave energy. The microwave source can be connected using a coupling and connection line suited to the transmission of microwave energy to the antenna or array. In the case of cryogenic therapy, for example, the operative member can be an appropriate applicator for the cryogenic gas or liquid such as a nozzle, array of nozzles in the case of a spray delivery, or a receptacle for a cryogenic fluid in the case where the therapy is applied via contact with a low temperature receptacle. The cryogenic applicator can be connected to the cryogenic source using a coupling and connection line suited to the controlled delivery of the cryogenic gas or liquid. In the case of photo-therapy, for example, the operative member can provide the appropriate fixed or moving lens or lens array suited as appropriate for the light source being used. The photonic delivery element can be connected to the light source using a coupling and connection line suited to the controlled delivery of the light or phototherapy energy generated by the phototherapy source.

Figure 14A:
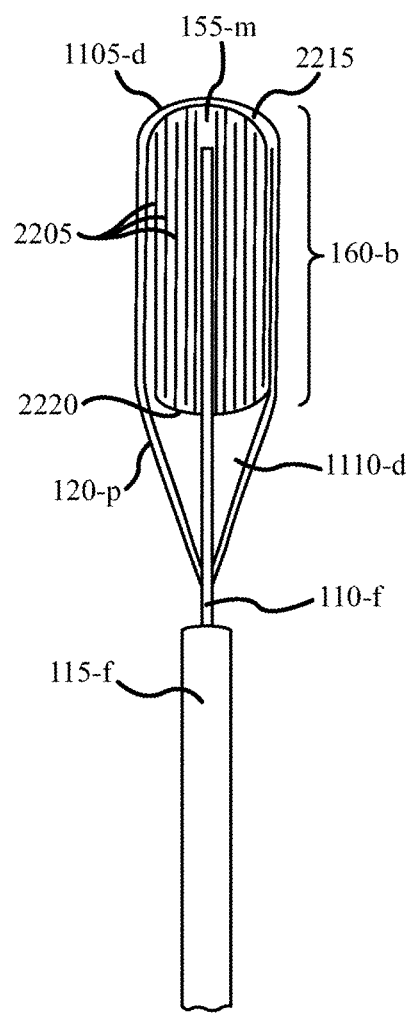
FIGS. 14A-14B are plan views of an electrode structure for an operative member according to various embodiments.

With reference to FIG. 14A, an operative member 160-*b* in accordance with various embodiments is shown. The operative member 160-*b* can be disposed on a surface of an expandable support device 120-*p*, such as a solid elastomeric support. A flexible support 155-*m* can be provided on the same surface or on an opposing surface of the expandable support device 120-*p*. The flexible support 155-*m* can be aligned with the central axis of the expandable support device 120-*p*. The expandable support device 120-*p* can be coupled with a guide assembly 110-*f*, which can be used to move the expandable support device 120-*p* and the operative member 160-*b* through a working channel 115-*f* and around a target treatment area. Both the operative member 160-*b* and the expandable support device 120-*p* can be configured to transition between a collapsed and expanded configuration.

In some embodiments, the operative member 160-*b* includes a flexible circuit. The flexible circuit can include multiple electrodes 2205. In some embodiments, the flexible circuit further includes a backing layer on which the electrodes are disposed. The backing layer, which can include an insulator, can then be disposed on the expandable support device 120-*p*. In some embodiments, the electrodes 2205 are disposed directly on the expandable support device 120-*p*. Various aspects of the flexible circuit are similar to typical integrated circuits and microelectronic devices. The operative member 160-*b* may include various operative and adjunctive medical devices other than electrodes.

In some embodiments, the multiple electrodes 2205 are aligned in parallel to one another and can form a row of electrodes 2205 spanning at least a portion of the width of the expandable support device 120-*p*. The electrodes 2205 can be spaced evenly apart from one another and/or at varying distances. The multiple electrodes 2205 can generally be aligned in parallel with an axis that extends from a distal end 1105-*d* to a proximal end 1110-*d* of the expandable support device 120-*p* on which the operative member 160-*b* is disposed. In some embodiments, this axis will be a central axis and will generally be located half way between opposing sides of the expandable support device 120-*p*. In some embodiments, the expandable support device 120-*p* is configured to collapse around this central axis when transitioning to a collapsed configuration. By aligning the multiple electrodes 2205 to be parallel with the central axis, the flexible circuit and the electrodes 2205 can also be configured to collapse around the central axis, as the electrodes 2205 will generally not resist the collapsing movement due to their parallel orientation. In such embodiments, the individual electrodes 2205 are not bent or deformed to a significant degree. Rather, the folding or collapsing may occur in the spaces between the electrodes 2205, and more specifically, in the flexible expandable support device 120-*p*. Consequently the expansion force utilized for expansion can be decreased.

In some embodiments, the flexible circuit extends to the perimeter of the expandable support device 120-*p*. Each electrode 2205 can extend from a proximal end 1110-*d* of the expandable support device 120-*p* to a distal end 1105-*d* of the expandable support device 120-*p*. In some embodiments, such as that shown in FIG. 14A, the multiple electrodes 2205 do not extend into the tapered portion of the proximal end 1110-*d* of expandable support device 120-*p*. The row of electrodes 2205 can extend to the lateral peripheral edges of the expandable support device 120-*p*. In some embodiments, the flexible circuit is generally coextensive with the shape of the expandable support device 120-*p*. In some embodiments, the flexible circuit is larger than the expandable support device 120-*p* such that a portion of the flexible circuit extends over a portion of the expandable support device 120-*p*. In some embodiments, the flexible circuit is smaller than the expandable support device 120-*p* such that a portion of the expandable support device 120-*p* extends beyond the perimeter of the flexible circuit. One may appreciate from the description herein that the shapes and positional relationship of the expandable support device 120-*p* and the operative member 160-*b* may be varied in other ways.

In some embodiments, the multiple electrode 2205 provide a bipolar electrode array. In such embodiments, the operative member 160-*b* can include a first bus 2215 and a second bus 2220. The first bus 2215 can be either a source line or a drain line. When the first bus 2215 is a source line, the second bus 2220 can be a drain line, and when the first bus 2215 is a drain line, the second bus 2220 can be a source line. Depending on whether the first bus 2215 is a source line or a drain line, the first bus 2215 can be coupled with a positive terminal or a negative or ground terminal. Similarly, depending on whether the second bus 2220 is a source line or a drain line, the second bus 2220 can be coupled with a positive terminal or a negative or ground terminal.

In some embodiments, the first bus 2215 is coupled with a first subset of the multiple electrodes 2205 and the second bus 2220 is coupled with a second subset of the multiple electrodes 2205. The first bus 2215 and the second bus 2220 can couple to alternating electrodes 2205 in the row of electrodes 2205 to thereby define the first subset of electrodes 2205 and the second subset of electrodes 2205.

In some embodiments, the first bus 2215 is located at a first end of the multiple electrodes 2205 and the second bus 2220 is located at the opposite end of the multiple electrodes 2205. The first bus 2215 and the second bus 2220 can be arched. In some embodiments, the first bus 2215 and the second bus 2220 are each a single arch extending the width of the expandable support device 120-p. The arched first bus 2215 located at the distal end 1105-d of the expandable support device 120-p can be parallel to the curvature of the distal end 1105-d, such as when the expandable support device 120-p has a paddle shape. The arched first bus 2215 at the distal end 1105-d of the expandable support device 120-p can be coupled with the first subset of electrodes 2205, which may extend away from the arched first bus 2215 towards the proximal end 1110-d. In some embodiments, the first subset of electrodes 2205 do not connect with the second bus 2220 at the proximal end 1110-d of the expandable support device 120-p. The arched second bus 2220 located near the proximal end 1110-d of the expandable support device 120-p can have an arch shape in the opposite direction of the first bus 2215 located at the distal end 1105-d. In other words, the arch shape of the second bus 2220 near the proximal end 1110-d of the expandable support device 120-p can curve away from the distal end 1105-d of the expandable support device 120-p. The second subset of electrodes 2205 can be coupled with the arched second bus 2220 at the proximal end 1110-d of the expandable support device 120-p and extend away from the arched second bus 2220 towards the distal end 1105-d of the expandable support device 120-p. In some embodiments, the second subset of electrodes 2205 do not connect with the first bus 2215 at the distal end 1105-d of the expandable support device 120-p.

Figure 14B:
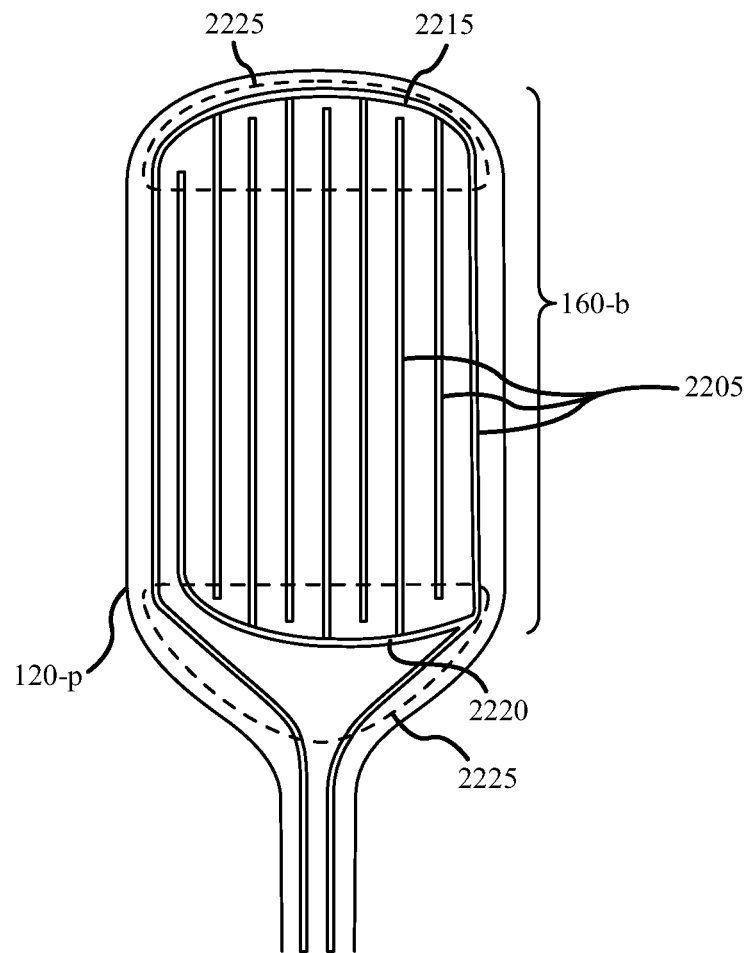

With reference to FIG. 14B, the first bus 2215 and the second bus 2220 can be at least partially covered with a material 2225 that may prevent or impedes the transmission of energy to the target treatment area in accordance with various embodiments. In some embodiments, the first bus 2215 and the second bus 2220 are covered with an insulation material 2225. Any suitable insulation material 2225 can be used, including, for example, polyimide. Covering the first bus 2215 and the second bus 2220 with insulation material 2225 can be useful to provide an operative member 160-b that delivers a more square treatment pattern, which can provide for more accurate and precise delivery of treatment to a target treatment area. For example, when the operative member 160-b is configured to provide ablative energy, the operative member 160-b having a covered first bus 2215 and second bus 2220 can deliver a square ablative pattern rather than one with rounded and less defined edges so as to provide for more accurate and precise ablation of the target treatment area.

FIG. 15A and FIG. 15B illustrate a flexible circuit, which may be similar to the flexible circuit shown in FIGS. 14A and 14B, in accordance with various embodiments. The first bus 2215-a and the second bus 2220-a provided can include multiple arches rather than a single arch as shown in FIGS. 15A and 15B. In some embodiments, the end of each arch is coupled with single electrode 2205-a. Thus, the end of each arch included in the first bus 2215-a may be coupled with a single electrode 2205-a in the first subset of electrodes, while the end of each arch included in the second bus 2220-a may be coupled a single electrode 2205-a in the second subset of electrodes. With reference to FIG. 15B, at least a portion of the first bus 2215-a including multiple arches and the second bus 2220-a including multiple arches can be covered with an insulation material 2225-a, such as polyimide.

Figures 17A, 17B:
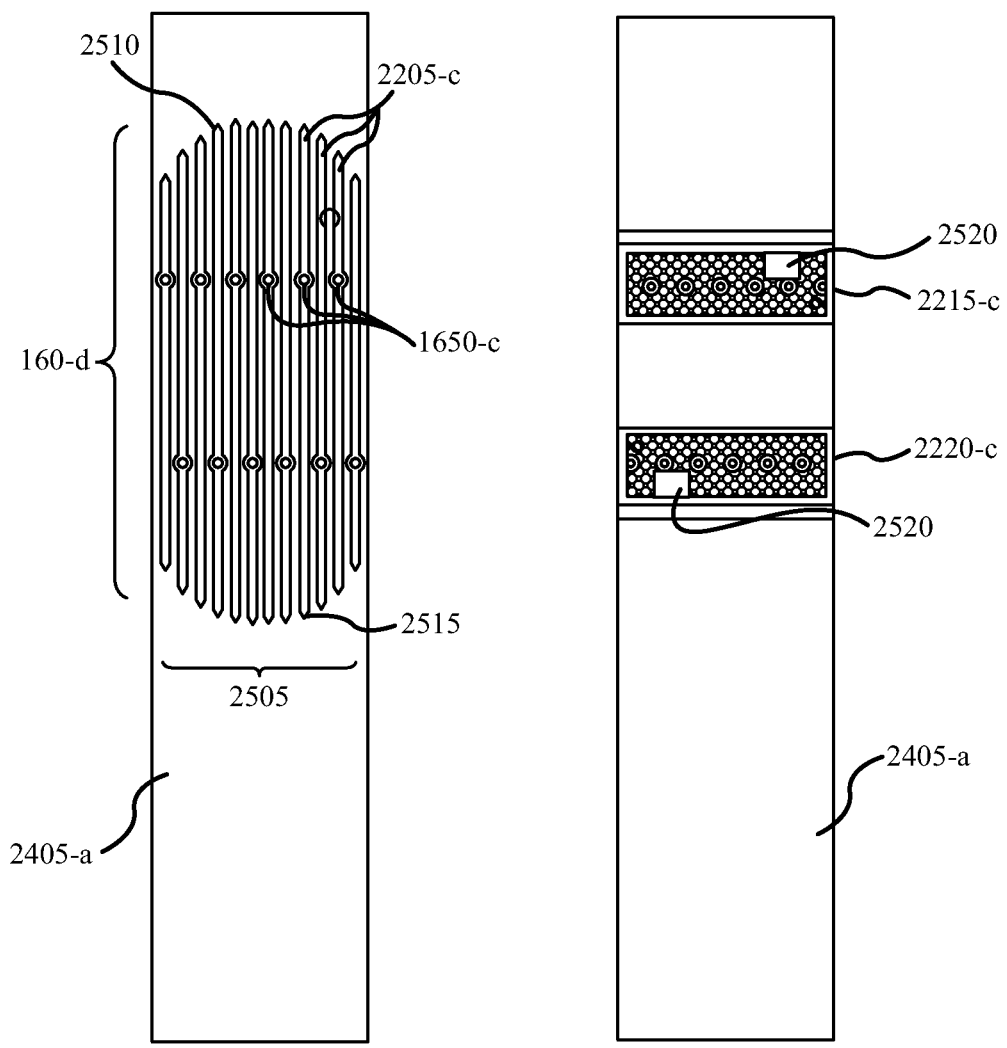
FIGS. 17A-17D are plan views of an operative member according to various embodiments.

While not shown in the FIG. 14A, 14B, 15A, or 15B, in some embodiments, the first bus and second bus are located on a surface of the expandable support device opposite the surface on which the flexible circuit (including the multiple electrodes) is disposed. FIGS. 17A and/or 17B may show such configurations. In such embodiments, the expandable support device can include one or more vias. The first and second bus can be connected to the first subset of electrodes and the second subset of electrodes, respectively, through the vias that provide a passage way between the front and back surface of the expandable support device. The first bus and the second bus disposed on the second surface of the expandable support device can be aligned substantially perpendicular to the electrodes disposed on the first surface of the expandable support device. The first bus and the second bus can be positioned at opposite ends of the electrodes as shown in FIGS. 14A, 14B, 15A, and 15B, at a location between the first end and second ends of the electrodes, or a combination of the two.

Any suitable material can be used for the electrodes, first bus, and/or second bus described above. In some embodiments, at least one of the electrodes, first bus, or second bus are made from copper. In some embodiments, the first bus and the second bus are made from copper. In some embodiments, the first bus and the second bus can include a hash pattern that includes multiple voids within the first bus and the second bus. This hash pattern, and specifically, the multiple voids, can improve the ease with which the first bus and second bus are capable of collapsing when the expandable support device transitions to a collapsed configuration. In embodiments where the first bus and the second bus are aligned perpendicular to the electrodes (and therefore perpendicular to the axis along which the expandable support device will collapse when transitioning to a collapsed configuration), the hash pattern can result in the first bus and the second bus providing less resistance to the collapsing of the expandable support device.

In some embodiments, the electrodes described above are formed from a patterned layer of electrode material disposed on a backing layer or the expandable support layer. After the layer of electrode material, which can include metal, for example, is disposed on an underlying support, traditional etching techniques can be used to remove portion so the electrode material and provide electrodes in desired pattern, including the patterns described above. In some embodiments, a 1 ounce copper can be used as the electrode material layer, and the electrode material layer can have a thickness of less than 0.01 inch thick. Other amounts of copper and/or thicknesses may be utilized in some embodiments.

The operative member can be attached to expandable support device with conventional fastening techniques, such as adhesives. In various embodiments, the operative member is attached to the expandable support device along an entire bottom surface. In various embodiments, only a portion of the operative member is attached to the expandable support device. In various embodiments, all or a portion of the periphery of the operative member is attached to the expandable support device. The operative member may be attached to the expandable support device only in selected regions, such as the center of the operative member. In various embodiments, the operative member is attached to the expandable support device in only selected locations to accommodate slippage or shearing between the structures. The operative member and its attachment to the support member can influence movement of the expandable support device between the collapsed to the expanded configurations.

Figure 16A:
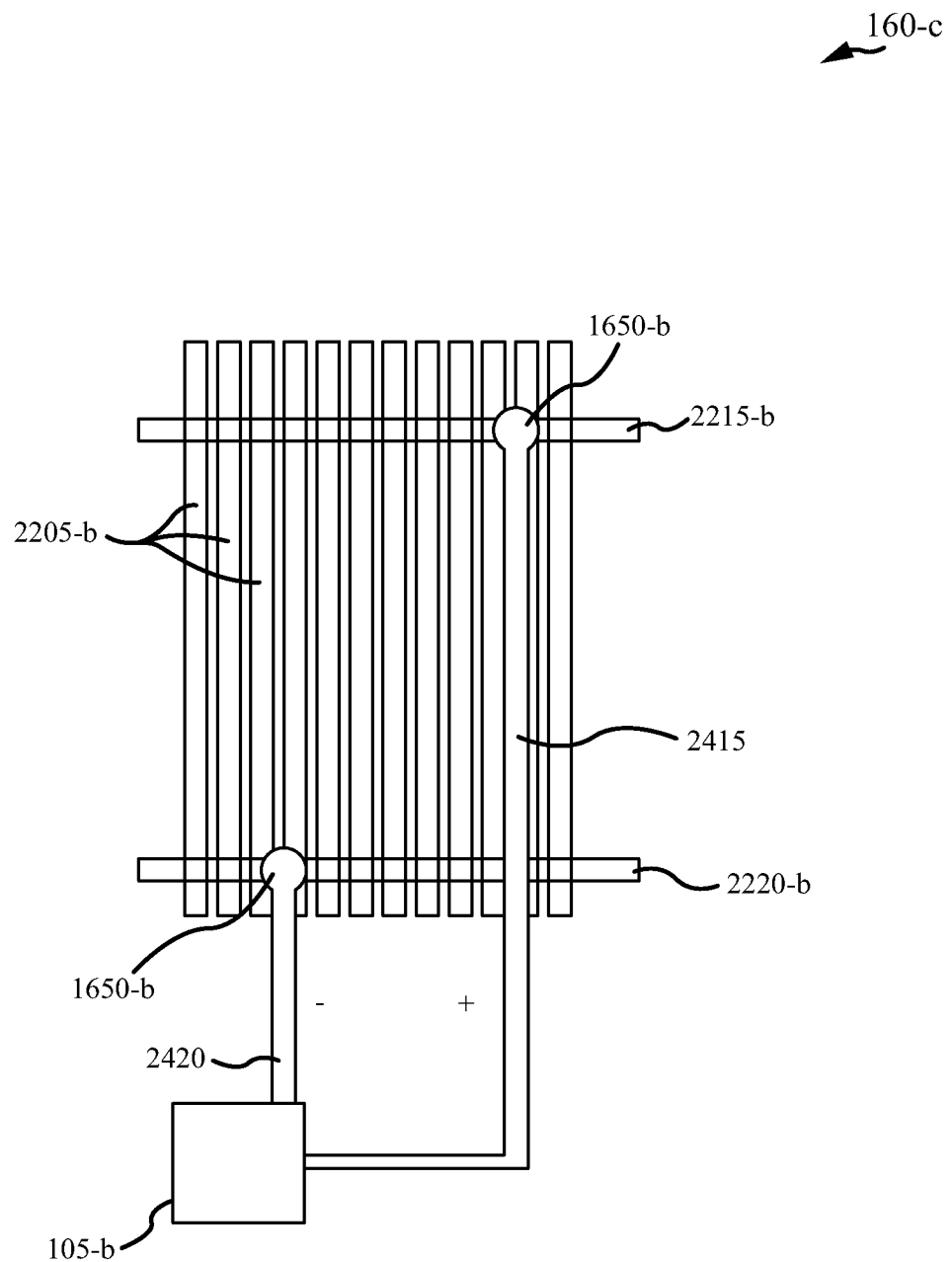
FIG. 16A is a schematic view of an electrode structure for an operative member according to various embodiments.
Figure 16B:
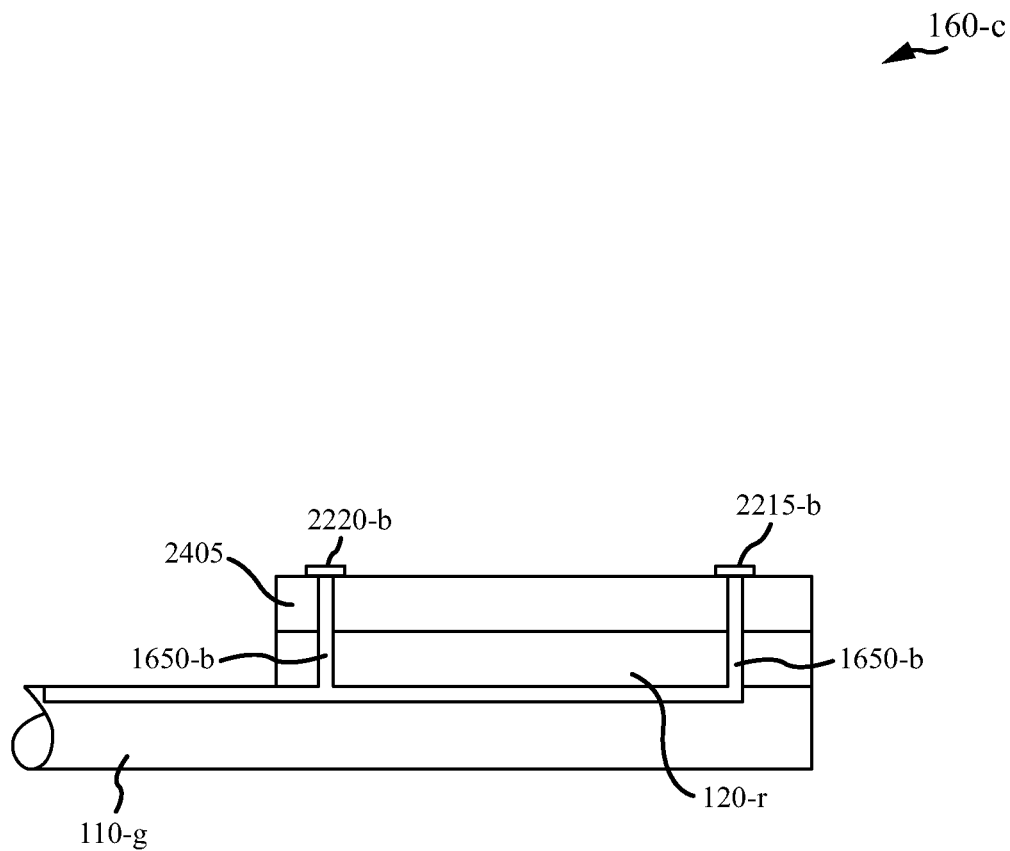
FIG. 16B is a cross-sectional view of the electrode structure shown in FIG. 16B according to various embodiments.

With reference to FIG. 16A and/or FIG. 16B, an operative member 160-c in accordance with various embodiments is shown. The operative member 160-c can be an RF ablation circuit for delivering RF ablation to a tissue surface. The operative member 160-c can include multiple electrodes 2205-b on an insulator material 2405. The electrodes 2205-b can be connected to a power source 105-b. The multiple electrodes 2205-b can be formed in a bipolar array. The electrodes 2205-b can be positioned over a source line first bus 2215-b and a drain line second bus 2220-b. The source line first bus 2215-b can be connected to a positive terminal of power source 105-b by an "in" line 2415, and the drain line second bus 2220-b can be connected to the negative terminal or ground by an "out" line 2420. The source line first bus 2215-b and drain line 2220-b can extend below the electrodes 2205-b. The source line first bus 2215-b and drain line second bus 2220-b may be configured as electrical bus lines. A portion of the multiple electrodes 2205-b can be connected to the source line first bus 2215-b, and the remainder of the electrodes 2205-b connected to the drain line second bus 2220-b. In some embodiments, the electrodes 2205 are alternately connected to the source line first bus 2215-b and drain line second bus 2220-b. When the power source 105-b activates the electrodes 2205-b, energy can travel from the positive electrodes to the ground or negative electrodes.

Source line first bus 2215-b may be connected to "in" line 2415 through a via 1650-b. Likewise, drain line second bus 2220-b may be connected to "out" line 2420 by a via 1650-b. The vias 1650-b can extend through the expandable support device 120-r. In various embodiments, the electrodes 2205-b include wires that are inserted through the vias 1650-b and connected to an electrical component or circuit below the expandable support device 120-r. In some embodiments, the "in" line 2415 and "out" line 2420 include a bundle of wires (e.g., Litz wires). The wires can extend through the guide shaft 110-g and connect to the power source 105-b at an opposite end. In various embodiments, the vias 1650-b are oversized relative to the electrical connections to accommodate lateral movement or shearing of the connections relative to the expandable support device 120-r during expansion and collapsing.

The electrodes 2205-b can be elongated and generally face in a common direction. In various embodiments, the electrodes 2205-b are aligned with a central axis of the expandable support device 120-r and/or the guide shaft 110-g. The operative member 160-c may include other configurations such as one or more monopolar electrodes.

The electrodes may have a length of between about 1 mm and about 10 mm, between about 1 mm and about 7 mm, between about 1 mm and about 6 mm, between about 1 mm and about 5 mm, between about 1 mm and about 3 mm, or between about 1 mm and about 4 mm. In various embodiments, the electrode length is between about 5 mm and about 50 mm, and in various embodiments about 15 mm. One may appreciate from the description herein that the length of the electrodes may vary depending on the application and expandable support device.

Each of the electrodes may have a width of about 4 mm, about 3 mm, about 2 mm, about 1 mm, about 0.9 mm, about 0.8 mm, about 0.7 mm, about 0.6 mm, about 0.5 mm, about 0.4 mm, about 0.3 mm, about 0.2 mm, or about 0.1 mm. In various embodiments, each electrode has a width of less than 1 mm. In various embodiments, each electrode has a width of about 0.25 inch. In various embodiments, an average width of the electrodes is about 4 mm, about 3 mm, about 2 mm, about 1 mm, about 0.9 mm, about 0.8 mm, about 0.7 mm, about 0.6 mm, about 0.5 mm, about 0.4 mm, about 0.3 mm, about 0.2 mm, or about 0.1 mm. In various embodiments, an average width of the electrodes is less than 1 mm. One may appreciate from the description herein that the electrodes may have different widths and/or lengths.

In various embodiments, a spacing between adjacent electrodes is based on the electrode length, width, shape, or a combination of the same. In some embodiments, the spacing between the electrodes is fixed by fastening the electrodes to a backing layer or the expandable support device. The spacing between adjacent electrodes may be between 0 mm and about 1 mm, between about 0 mm and about 0.5 mm, between about 0 mm and about 0.4 mm, between about 0 mm and about 0.3 mm, or between about 0 mm and about 0.2 mm. The spacing between adjacent electrodes may be less than 0.3 mm, less than 0.2 mm, less than 0.1 mm, or less than 0.05 mm. In various embodiments, the spacing between adjacent electrodes is about 0.3 mm. One may appreciate from the description herein that the electrodes may have different spacing.

One may appreciate that the dimensions and lay out of the electrode may vary depending on the application. For example, if the working channel is larger, it may be desirable to use an expandable support device with a larger treatment surface and/or larger electrodes. A larger target treatment surface can typically require scaling up the constituent elements including the operative members.

One may appreciate from the description herein that the operative member may be configured differently depending on the application requirements. In various embodiments, the operative member includes multiple electrode arrays. The arrays can be individually powered. The number and type of electrodes may also vary.

In various embodiments, the dimensions of the electrodes and spacing between the electrodes are selected to enable controlled depth ablation. Examples of electrode configurations for controlled depth ablation are described in U.S. Pat. No. 6,551,310 (Ganz et al.), U.S. Pat. No. 7,150,745 (Stern et al.); U.S. Pat. No. 7,344,535 (Stern et al.); U.S. Pat. No. 7,530,979 (Ganz et al.); U.S. Pat. No. 7,993,336 (Jackson et al.); U.S. Pat. No. 8,012,149 (Jackson et al.); and U.S. Patent Pub. Nos. 2008/0097427 (Stern et al.); 2009/0012513 (Utley et al.), and 2009/0048593 (Ganz et al.); the entire contents of which patents and patent publications are hereby incorporated herein for all purposes. In various embodiments, the power generator and/or a controller are configured to control the application of energy using the operative member to effect ablation of tissue to a controlled depth.

In some embodiments, the electrodes 2205-b shown in FIGS. 16A and 16B are oriented parallel to an axis about which the collapsing and expanding of the expandable support member 120-r occurs in order to promote the collapsing and expansion functions. Although the electrodes 2205-b can be separated from the expandable support device 120-y by an insulator layer 2405, the electrodes 2205-b may influence each other during bending. For example, if the electrodes 2205-b are fastened to a insulator layer 2405 in a way that makes the resulting circuit more rigid, this may resist bending of the expandable support device 120-r. In various embodiments, the electrodes 2205-b are positioned on the expandable support device 120-r to minimize overlapping with other support structures, such as the support splines. In various embodiments, the electrodes and splines are positioned and configured in an intersecting relationship.

Figure 17C:
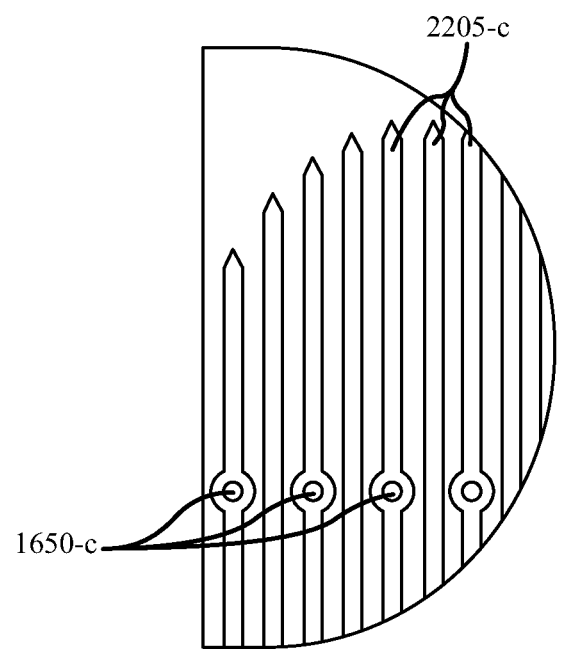

FIGS. 17A-17D illustrate an operative member 160-d in the form of a flexible circuit in accordance with various embodiments. The operative member 160-d can be attached to a top surface of the expandable support device. FIG. 17A shows a top side of operative member 160-d. FIG. 17B shows a back side of the operative member 160-d. FIG. 17C is an enlarged view of a portion of the operative member 160-d as seen from the top side. The operative member 160-d can be configured as an adhesive strip for applying to the expandable support device.

In some embodiments, the expandable support device on which the operative member 160-d is disposed is about 7 mm to about 8 mm in width. The operative member 160-d can include an electrode array 2505 that extends across all or substantially all of the expandable support device width. In some embodiments, the electrode array 2505 can have a width between about 7 mm and about 8 mm. The width of the expandable support device and/or the electrode array 2505 may depend on the size of the working channel through which they are intended to be deployed.

In some embodiments, the electrode array 2505 includes twelve electrodes 2205-z in the shape of bars. In some embodiments, the electrodes 2205-c can be formed of 1 ounce copper on each side of an insulator sheet or backing. In some embodiments, each electrode 2205-c can have a width between about 0.2 inch and about 0.3 inch, and preferably 0.25 inch. In some embodiments, the spacing between adjacent electrodes 2205-c can be between about 0.25 inch and about 0.4 inch, and preferably 0.3 inch. The length of the electrodes 2205-c can vary. In some embodiments, the electrodes 2205-c positioned interiorly are longer than the electrodes 2205-c along the sides of the operative member 160-d. In various embodiments, the electrodes 2205-c along the central axis have the greatest length, and the length decreases moving towards the sides of the electrode array 2505. In some embodiments, electrode array 2505 defines a rounded treatment surface. The distal edge 2510 and proximal edge 2515 of the electrode array 2505 can be curved.

The operative member 160-d can include an array of electrodes 2505 on an insulator material 2405-a with an adhesive backing. The electrodes 2205-c can extend in a longitudinal direction on a top surface of the insulator material 2405-a. As shown in FIG. 17B, the back side of the insulator material 2405-a may include a first bus 2215-c and a second bus 2220-c in accordance with various embodiments. As shown in FIG. 17C, each of the electrodes 2205-z on the top surface can be connected to one of the first bus 2215-c or the second bus 2220-c by vias 1650-c in accordance with various embodiments. The first bus 2215-c and the second bus 2220-c can be formed of copper over the insulator material 2405-a. The first bus 2215-c and second bus 2220-c can have a hatched pattern.

The operative member can include solder pads 2520. In some embodiments, the operative member 160-d includes two pads 2520 for the positive and negative terminals. One may appreciate that the operative member 160-d may include one, two, or more pads and buses depending on the configuration. For example, the operative member 160-d may be configured as a monopolar electrode array with a single bus line.

Figure 17D:
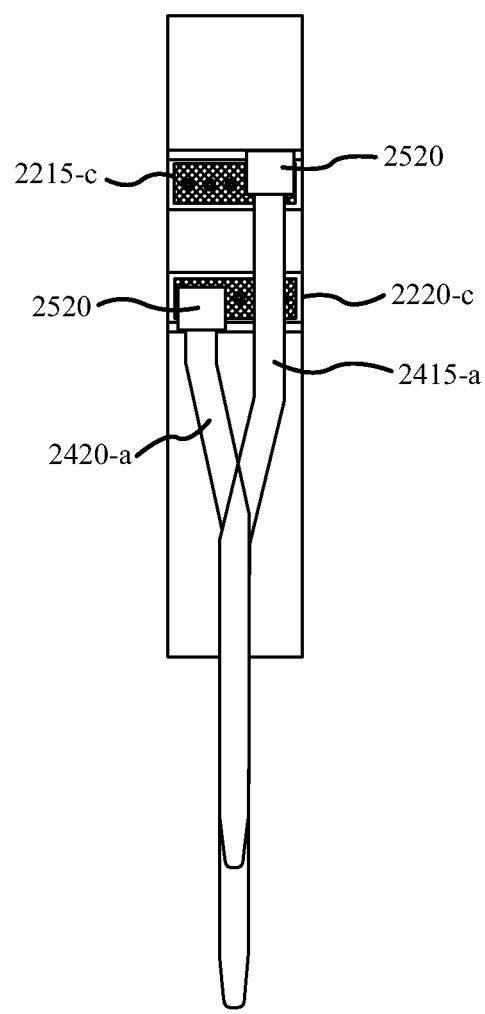

With reference to FIG. 17D, the operative member 160-d can includes line 2415-a for connecting the first bus 2215-c to a positive terminal and a line 2420-a for connecting the second bus 2220-c to ground in accordance with various embodiments. The lines 2415-a and 2420-a can be connected to the first bus 2215-c and the second bus 2220-c, respectively, by the pads 2520. Pads 2520 can be shaped and positioned for inserting into cut-outs in an expandable support device.

Although described in terms of an electrode array for RF ablation, one may appreciate that the operative members suitable for use embodiments described herein may be configured for administering other forms of therapy or diagnosis. For example, the techniques described above may be applied to form an antenna for microwave ablation. In another example, the operative member may include sensor elements overlaying the expandable support device. Monopolar RF configurations can also be used in some embodiments. Some embodiments may utilize bipolar RF configurations.

In various embodiments, the operative members described herein are ablation devices, and in some embodiments, RF ablation devices. In various embodiments, the operative members described herein are configured for thermal ablation. In some embodiments, the operative members described herein are configured to heat surrounding tissue by resistive heating or conduction. Embodiments of operative members described herein can be configured to treat or diagnose the surrounding tissue by other modalities.

In various embodiments, the operative members described herein are configured for ablation of abnormal tissue in the esophagus. In various embodiments, the operative members described herein are configured for ablation of abnormal tissue in the lower esophageal sphincter. In various embodiments, the operative members described herein are configured for ablation of Barrett's esophagus and/or pre-cancerous tissue in the epithelium without injuring the underlying muscalaris. In various embodiments, the operative members described herein are configured for use in a variety of body lumens and organs including, but not limited to, the gastrointestinal (GI) tract (e.g. the esophagus or duodenum), the alimentary tract, the digestive system (e.g. the bile duct), the cardiovascular system, the endocrine system (e.g. the pancreas), and the respiratory system.

In various embodiments, the operative members described herein are configured to ablate tissue to a predetermined depth. In various embodiments, the operative members described herein are configured to ablate mucosal tissue without injuring the underlying submucosal tissue. In various embodiments, the operative members described herein are configured to ablate mucosal tissue without injuring the underlying muscalaris. In various embodiments, the operative members described herein are configured to apply the appropriate level of energy to the tissue to achieve an ablation depth that does not extend beyond the submucosa layer of the esophagus. In various embodiments, the operative members described herein are configured to control the depth of ablation to the epithelium. In various embodiments, the operative members described herein are configured for superficial ablation. For example, various embodiments of an operative member may be configured to sear the tissue surface. In various embodiments, the operative members described herein are configured to deliver sufficient energy to initiate regrowth of tissue, for example, in a mucosal layer.

Controlling the depth of ablation is based on several factors such as power and treatment time. In various embodiments, the power source activates the electrode array with sufficient power and for a sufficient amount of time to ablate tissue to a predetermined depth. In an exemplary embodiment, the power source activates the electrode array with sufficient power and for a length of time necessary to deliver between about 1 J/sq.-cm and about 50 J/sq.-cm, between about 10 J/sq.-cm and about 40 J/sq.-cm, between about 15 J/sq.-cm and about 105 J/sq.-cm, between about 25 J/sq.-cm and about 105 J/sq.-cm, between about 30 J/sq.-cm and about 105 J/sq.-cm, between about 35 J/sq.-cm and about 105 J/sq.-cm, or between about 40 J/sq.-cm and about 105 J/sq.-cm. Other energy per unit area amounts may be utilized in some embodiments.

In various embodiments, the operative member is configured to deliver between about 10 Watts/sq.-cm and about 50 Watts/sq.-cm, between about 10 Watts/sq.-cm and about 40 Watts/sq.-cm, between about 10 Watts/sq.-cm and about 30 Watts/sq.-cm, between about 15 Watts/sq.-cm and about 30 Watts/sq.-cm, or between about 15 Watts/sq.-cm and about 40 Watts/sq.-cm. Other energy per unit area amounts may be utilized in some embodiments.

In various embodiments, the power generator is configured to activate the electrodes for between about 10 ms and about 5 minutes, between about 100 ms and about 1 minute, between about 100 ms and about 30 seconds, between about 10 ms and about 1 second, between about 100 ms and about 1 second, or between about 300 ms and about 800 ms. In various embodiments, the power generator is configured to activate the electrodes for less than 1 second, less than 500 ms, or less than 300 ms. In some embodiments, the operative member is configured to deliver about 40 W/sq.-cm for a duration of about 300 ms to about 800 ms. In some embodiments, the operative member is configured to deliver between about 12 J/sq.-cm to about 15 J/sq.-cm for a duration of about 300 ms to about 800 ms. Other energy per unit area amounts and time amounts may be utilized in some embodiments.

In some embodiments, a guide assembly is provided for delivering and positioning an expandable support device and an operative member disposed thereon through a working channel and to a target treatment area. The guide assembly can include one or more guide shafts. Each guide shaft can generally include a relatively long and thin cylindrical body. Each guide shaft can include a proximal end and a distal end. In some embodiments, the distal end of one guide shaft is coupled with the expandable support device and the proximal end of one guide shaft is coupled with a power source.

The material of each guide shaft is generally not limited. Suitable materials for the guide shafts include, but are not limited to, metals and thermoplastics. The material of the guide shafts can be rigid, flexible, or include sections of both rigid and flexible material. In various embodiments, the guide shafts are formed of the same material as the expandable support device. One of the guide shafts may be integrally formed with the expandable support member or formed as a separate piece. When the guide shaft is a separate piece from the expandable support member, the guide shaft can be coupled with the expandable support device using any suitable material or technique, such as, for example, by welding or adhesives.

In various embodiments, the guide shafts have a uniform thickness. In various embodiments, the guide shafts have a thickness of about 0.01 inch, about 0.012 inch, or about 0.002 inch. In various embodiments, the guide shafts have a thickness of 0.012 inch+/−0.0005 inch.

With reference to FIG. 18A, a guide assembly 110-h is shown in accordance with various embodiments. The guide assembly 110-h can include two separate shaft sections through which one or more transmission wires 3105 can pass. The first shaft 112-a (which can also be referred to as a distal shaft) and the second shaft 114-a (which can also be referred to as a proximal shaft or the power source side shaft) are separated by a break 140-a. The first shaft 112-a can extend from the break 140-a up towards the expandable support device coupled with the distal end of the guide assembly 110-h. The second shaft 114-a extends back from the break towards the power source used to supply power to the expandable support device. The first shaft 112-a and the second shaft 114-a can be configured to axially move an expandable support device and an operative member disposed thereon, such as axially through a working channel.

The one or more transmission lines 3105 can be configured for operatively connecting an operative member to a power source. Accordingly, in some embodiments, the transmission lines 3105 have a proximal end coupled with a power source and a distal end coupled with an operative member on an expandable support device while extending through both the second shaft 114-a and the first shaft 112-a of the guide assembly 110-h. In this manner, the first shaft 112-a and the second shaft 114-a enclose at least a portion of the one or more transmission lines 3105. In some embodiments, the one or more transmission lines 3105 are exposed at the break 140-a due the first shaft 112-a being separated from the second shaft 114-a. In some embodiments, the transmission lines are electrical wires.

In some embodiments, the first shaft 112-a can be configured such that it is capable of rotating independently of the second shaft 114-a. This can be due at least in part to the break 140-a separating the first shaft 112-a from the second shaft 114-a. In some embodiments, the second shaft 114-a is coupled at a proximal end to the power source. The break 140-a between the first shaft 112-a and the second shaft 114-a can help to ensure that that the coupling between the power source and second shaft 114-a does not impede the transmission of torque from the first shaft 112-a to the expandable support device.

In some embodiments, the separation of the first shaft 112-a from the second shaft 114-a allows the first shaft 112-a to be configured for transmitting torque to the expandable support member and any operative member disposed thereon. In some embodiments, this is accomplished by coupling at least a portion of the first shaft 112-a to at least a portion of the expandable support device and/or the transmission lines 3105 so that rotation of the first shaft 112-a is transmitted to the expandable support device and/or transmission lines 3105. When the first shaft 112-a is coupled with the transmission line 3105, the transmission lines 3105 can be coupled with the first shaft 112-a at the distal end of the first shaft 112-a while being decoupled with the first shaft 112-a at the proximal end of the first shaft 112-a. This can help to ensure that the first shaft 112-a is configured to transmit torque to the expandable support device and/or the transmission lines 3105.

With reference to FIG. 18B, in some embodiments, the break 140-a can be covered by a protection element 165-a. The protection element 165-a can be made of any suitable material and can have any shape and/or size that allows it to cover the break 140-a and protect the transmission lines 3105. As shown in FIG. 18B, the protection element 165-a can have a generally cylindrical shape, although other shapes can be used. In some embodiments, the protection element 165-a is coupled with the first shaft 112-a and is sufficiently long to extend over the break 140-a and a portion of the second shaft 114-a. In some embodiments, the protection element 165-a is decoupled from the second shaft 112-a so that the first shaft 112-a can continue to rotate independently of the second shaft 114-a. The coupling of the protection element 165-a to the first shaft can allow the protection element to be configured to transmit rotational motion to the first shaft 112-a. In this manner, the protection element 165-a can also serves as a torque handle that aids a user in rotating the first shaft 112-a to transmit torque to the expandable support device.

FIG. 18B also shows a working channel 115-g into which the first shaft 112-a can be inserted. In some embodiments, an expandable support device located at the distal end of the first shaft 112-a is inserted into the working channel 115-g in a collapsed configuration, and the guide assembly 110-h is used to move the expandable support device through the working channel 115-g. In some embodiments, the first shaft 112-a will be the predominant portion of the guide assembly 110-h that enters the working channel 115-g. The protection element 165-a can serves as a stopper which prevents further insertion of the guide assembly 110-c into the working channel 115-g.

The first shaft 112-a can be made from a flexible material, which will allow the first shaft 112-a to move more readily through a working channel 115-g having tortuous path. In some embodiments, the flexible material used for the first shaft 112-a is stainless steel, such as a stainless steel cable material. In some embodiments, first shaft 112-a includes two or more concentric layers, with each layer being made from two or more stainless steel wires wound around a common axis.

Figure 19B:
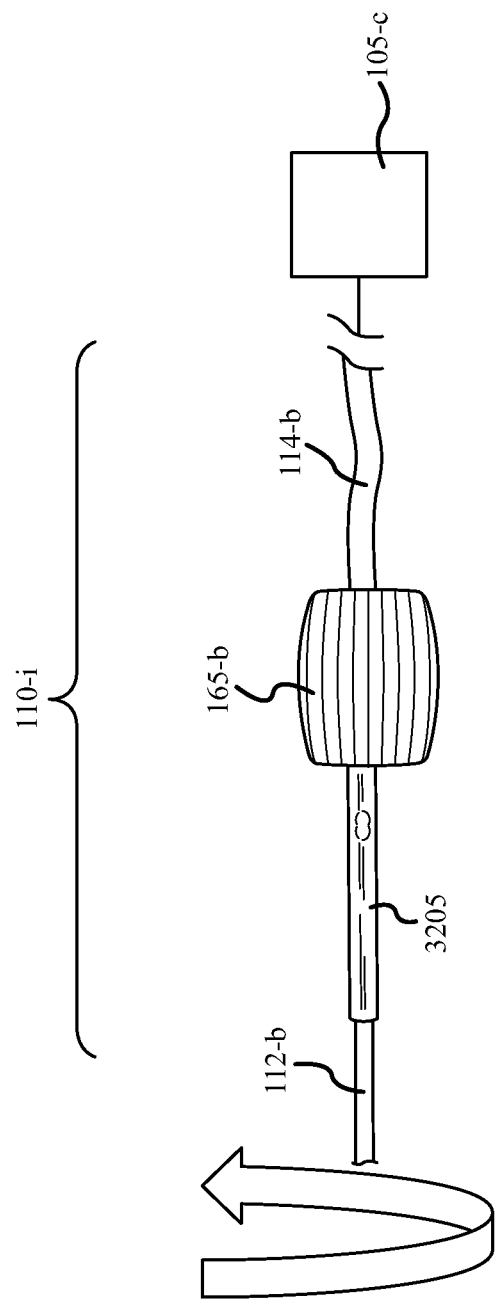

FIG. 19A and/or FIG. 19B illustrate a guide assembly 110-i in accordance with various embodiments. The guide assembly 110-i is similar in many respects to the guide assembly 110-h illustrated in FIGS. 18A and/or 18B. The guide assembly 110-i can include a first shaft 112-b, a second shaft 112-b, and a protection element 165-b located between the first shaft 112-b and the second shaft 114-b. In some embodiments, the first shaft 112-b is configured to extend through a working channel and transmit torque to an expandable support device coupled with the distal end of the first shaft 112-b.

The protection element 165-b can be positioned between the first shaft 112-b and second shaft 114-b. As shown in FIGS. 19A and 19B, the protection element 165-b can include a knurled surface to aid in manipulation by a user. First shaft 112-b can be configured to transmit torque applied to protection element 165-b to an expandable support device to cause rotation. In various embodiments, the first shaft 112-b is configured to transmit up to 5 in.-oz. of torque, and preferably up to 9 in.-oz. of torque.

The second shaft 114-b can include a tubular body through which an one or more transmission line can be routed to a power source 105-c. The second shaft 114-b may also be configured for receiving other connections. The second shaft 114-b may be formed of plastic such as nylon, a thermoplastic elastomer such as Pebax® (polyether block amide), or polytetrafluoroethylene (PTFE). The second shaft 114-b can be elongated to allow the power source 105-c to be positioned remotely from the patient receiving treatment. In various embodiments, the first shaft 112-b and the second shaft 114-b can be transparent to enable visual inspection by the user. For example, the internal components may include markers or indexes to enable the user to visually verify the axial position of the expandable support device when it is inserted into the patient's body.

In some embodiments, the transmission line and/or other internal components extend through the entire guide assembly 110-i. In various embodiments, the components are separated into two sections provided with first shaft 112-b and second shaft 114-b alike.

In some embodiments, the second shaft 114-b is not attached to the internal components such as the transmission wires. This can allow the second shaft 114-b to rotate independently of the internal components. In practice, the second shaft 114-b can be attached to a fixed device like the power source 105-c whereas the internal wires rotate with the expandable support device. Thus, the second shaft 114-b can house the wires without twisting during operation. As may be appreciated by one of skill in the art, the wires are capable of twisting to a larger degree than the second shaft 114-b. This can allow the second shaft 114-b to be rotated to a significant degree without buckling, crimping, or binding.

In some embodiments, the second shaft 114-b generally does not play a role in movement of the expandable support device at the distal end of the guide assembly 110-i. Instead, the second shaft 114-b is simply "along for the ride" to house the internal components. The second shaft 114-b can be rigid or flexible.

First shaft 112-b can be configured to transmit torque to the expandable support device to cause rotation. The first shaft 112-b can be sufficiently flexible to allow it to move through a tortuous working channel, but can also have sufficient rigidity to transmit axial force to the expandable support device. Torque from the protection element 165-b can be transmitted through the first shaft 112-b to the expandable support device thereby causing rotation of the expandable support device. Similarly, an axial force on the protection element 165-b can cause the first shaft 112-b to push on the expandable support device and move it axially.

The first shaft 112-b can be coupled with expandable support device at a distal end and a protection element 165-b at a proximal end. In some embodiments, the first shaft 112-b also includes a rigid section 3205 at the proximal end. In some embodiments, the rigid section 3205 can serve as a fastener between the protection element 165-b and the first shaft 112-b. The rigid section 3205 can connect the first shaft 112-b to the protection element 112-b rotationally and axially. In some embodiments, rigid section 3205 is a stainless steel hypotube connected to the protection element 165-b. The rigid section 3205 can be crimped to fix the protection element 165-b to the first shaft 112-b. The rigid section 3205 can maintain the alignment of the guide assembly 110-i in the proximal end of a working channel and ensures good torque transfer from the protection element 165-b to the first shaft 112-b. The rigid section 3205 can be configured to be inserted into a working channel. In some embodiments, the rigid section 3205 has a length of about 2 cm. When the rigid section 3205 is included, the first shaft 112-b can be considered to include a rigid section 3205 and a flexible section, with the flexible section being positioned between the expandable support device having an operative member disposed thereon and the rigid section 3205. An introducer may also be used in conjunction with the rigid section 3205 to aid in alignment and movement within the working channel.

Unlike second shaft 114-b, first shaft 112-b can be rotationally fixed to the transmission wires and the protection element 165-b. In other words, rotation of protection element 165-b can cause the first shaft 112-b to rotate which in turn causes the expandable support device to rotate. At the same time, the wires can rotate based on rotation of the expandable support device. However, second shaft 114-b can remain fixed to the generator while the wires twist internally in some cases. Thus, the first shaft 112-b can be torqueable with the protection element 165-*b* but the second shaft 114-*b* is not. Put another way, the first shaft 112-*b* and the second shaft 114-*b* can be rotationally decoupled from each other.

The transmission lines extending through the first shaft 112-*b* and the second shaft 114-*b* can be relatively flexible. In some embodiments, the transmission lines are generally not at risk of kinking when the first shaft 112-*b* is rotated. The transmission lines can simply twist and turn inside the second shaft 114-*b*. In some embodiments where the transmission lines are only fixed to a distal end of the first shaft 112-*b*, the transmission lines may be free to also rotate within the first shaft 112-*b*.

In various embodiments, guide assembly 110-*i* is configured to reduce torquing and twisting of the transmission line. The transmission lines may include a proximal end and a distal end that are decoupled from each other. For example, protection element 165-*b* may include a mechanical device for decoupling rotation of the transmission wires extending distally from the protection element 165-*b* from the transmission wires at the proximal end. Suitable devices for decoupling rotation of the transmission wires include, but are not limited to, a bearing, a bushing, a stator and core assembly, and the like.

In various embodiments, protection element 165-*b* is configured as a quick connector. As may be understood by one of skill from the description herein, the first shaft 112-*b* and the second shaft 114-*b* can be configured as independent assemblies, each with their own set of transmission lines. Thus, the protection element 165-*b* can be configured to easily connect and disconnect to the first shaft 112-*b* and the second shaft 114-*b*. This may beneficially improve ease-of-use during surgery. In various embodiments, the first shaft 112-*b* is disposable and the second shaft 114-*b* can be re-used.

Suitable materials for the first shaft 112-*b* include, but are not limited to, thermoplastics and stainless steel. In various embodiments, the first shaft 112-*b* is Nylon 12 with a 0.002"×0.005" stainless steel braid. In various embodiments, the first shaft 112-*b* is a 0.002"×0.005" tube formed of Pebax®. In some embodiments, the first shaft 112-*b* is made of a stainless steel coil shaft. The protection element 165-*b* may be formed of thermoplastics such as acrylonitrile butadiene styrene (ABS) and other materials. In various embodiments, the second shaft 112-*b* includes a lubricious liner (e.g. PTFE or FEP) to aid with assembly and rotation of the transmission lines. In various embodiments, transmission lines are a bundle of one or more conductive wires.

In some embodiments, the guide assembly further includes a handle element. The handle element can be coupled with a first shaft to assist in transmitting torque to the expandable support device and/or to move the expandable support device in an axial direction. In some embodiments, the handle element includes a body and a channel extending through the body. The first shaft can pass through the channel to thereby couple the handle element to the first shaft. In some embodiments, the handle element is configured such that the first shaft can move through the channel. The handle element can also include a rigid section extending off a distal end of the handle element through which the first shaft can also pass. The rigid section on the handle element can be similar in many respect to the rigid section 3205 described above. The rigid section extending from the distal end of the handle element can be at least 2 cm long and can be configured for insertion into a working channel.

In some embodiments, the handle element is positioned at the proximal end of the first shaft. The handle element can be configured to extend over a portion of the second shaft so that it serves as a protection element for any transmission wires that may be exposed due to a break between the first shaft and the second shaft.

Figure 20:
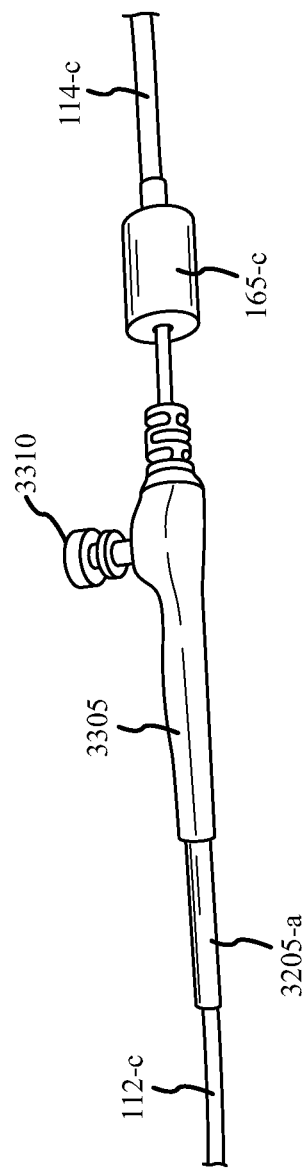
FIG. 20 is a perspective view of a handle element for use with a guide assembly according to various embodiments.

With reference to FIG. 20, a handle element 3305 is shown in accordance with various embodiments. The handle element 3305 can have a generally elongate shape and can be coupled with a first shaft 112-*c* by virtue of the first shaft 112-*c* passing through a channel in the body of the handle element 3305. The handle element 3305 can be configured to slide along the first shaft 112-*c*. In some embodiments, the handle element includes a locking mechanism 3310. The locking mechanism 3310 can be configured to lock the handle element 3305 at a position along the length of the first shaft 112-*c*. This can be achieved using any suitable locking mechanism 3310. In some embodiments, the locking mechanism 3310 is fixed to the handle element 3305 such that when the locking mechanism 3310 is engaged against the first shaft 112-*c* (for example, by screwing the locking mechanism 3310 down against first shaft 112-*c* until the first shaft 112-*c* is pinched between the locking mechanism 3310 and the handle element 3305), the handle element 3305 is locked into position by virtue of being fixed to the locking mechanism 3310.

In some embodiments, the handle element 3305 is provided to control the length of the first shaft 112-*c* that can be inserted into a working channel. The handle element 3305 can serve as a stopper. When the handle element 3305 is moved towards the distal end of the first shaft 112-*c* and is locked in place, the handle element 3305 can shorten the amount of first shaft 112-*c* that can pass into the working channel. When the handle element 3305 is moved towards the proximal end of the first shaft 112-*c*, the handle element 3305 can increase the amount of first shaft 112-*c* that can pass into the working channel. In operation, a practitioner can insert the expandable support and the first shaft 112-*c* into a working channel until the expandable support device emerges from the distal end of the working channel and is brought close to the target treatment area. The handle element 3305 can then slide along the first shaft 112-*c* towards the distal end until the handle element 3305 rests against entry of the working channel. By locking the handle element 3305 in place at that position, the practitioner can effectively set the length of the first shaft 112-*c* and ensure that the expandable support device will stay in the desired location near the target area so long as the handle element 3305 is resting against the working channel entry.

FIG. 20 shows that the handle element 3305 can also include a rigid section 3205-*a* at the distal end that is configured to be inserted into a working channel and help align the handle element 3305. The rigid section 3205-*a* may be similar or identical to the rigid section 3205 described above. FIG. 20 also shows that the handle element 3205 can be used in a conjunction with a protection element 165-*c*. The protection element 165-*c* can be similar or identical to the protection element 165-*b* described above. The protection element 165-*c* can be coupled with the first shaft 112-*c* and can extend over a portion of the second shaft 114-*c* to protect exposed transmission lines at the break. The protection element 165-*c* can also be provided to prevent the handle element 3305 from sliding over the second shaft 114-*c*.

Figure 21:
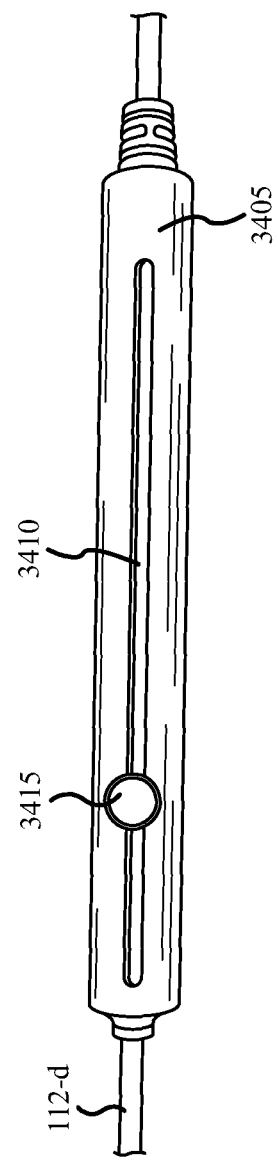
FIG. 21 is a perspective view of a handle element for use with a guide assembly according to various embodiments.

With reference to FIG. 21, a handle element 3405 in accordance with various embodiments is shown. The handle element 3405 can have a generally elongate shape and can be coupled with a first shaft 112-*d* by virtue of the first shaft 112-*d* passing through a channel in the body of the handle element 3405. The handle 3405 can include an axial path 3410 along which a locking mechanism 3415 can slide towards the distal or proximal end of the handle element 3405. The locking mechanism 3415 can be configured to be secured to a portion of first shaft 112-d located within the channel of the handle element 3405. The locking mechanism can also be locked in place anywhere along the axial path 3410. Accordingly, when in an unlocked position, the locking mechanism 3415 can move along the axial path 3410, but when in the locked position, the locking mechanism 3415 is fixed to the handle element 3405 and cannot slide along the axial path 3410.

Whether in a locked or unlocked position, the locking mechanism 3405 can remain secured to a portion of the first shaft 112-d. In this manner, the locking mechanism can move the first shaft 112-d in and out of the handle element 3405 when in the unlocked position, and can hold the first shaft 112-d in place when in the locked position. Thus, the handle 3405 is configured to adjust and control the amount of first shaft 112-d extending out of the handle element 3405 and, correspondingly, the length of the first shaft 112-d that can be fed through the working channel. For example, when the handle element 3405 is positioned against the entry of the working channel, the locking mechanism 3415 can be moved towards the proximal end of the handle element 3405 to shorten the length of the first shaft 112-d and pull the expandable support member back towards the working channel. The locking mechanism 3415 can also be moved towards distal end of the handle element 3405 to increase the length of the first shaft 112-d and move the expandable support member closer to the target treatment area. Once a desired position is achieved for the expandable support device, the locking mechanism 3415 can be locked against the handle element 3405 to fix the position of the expandable support device.

In some embodiments, the guide assembly is coupled with the expandable support device using a torque member. The torque member can be a structure located at the distal end of the first shaft, a structure located at a proximal end of the expandable support device, or a combination of the two. The torque member is generally configured to ensure that torque generated by rotation of first shaft is transmitted to expandable support device. In some embodiments, the guide assembly and/or the torque member are configured such that approximately one to one rotation movement is achieved between the guide assembly and the torque member.

Figure 22:
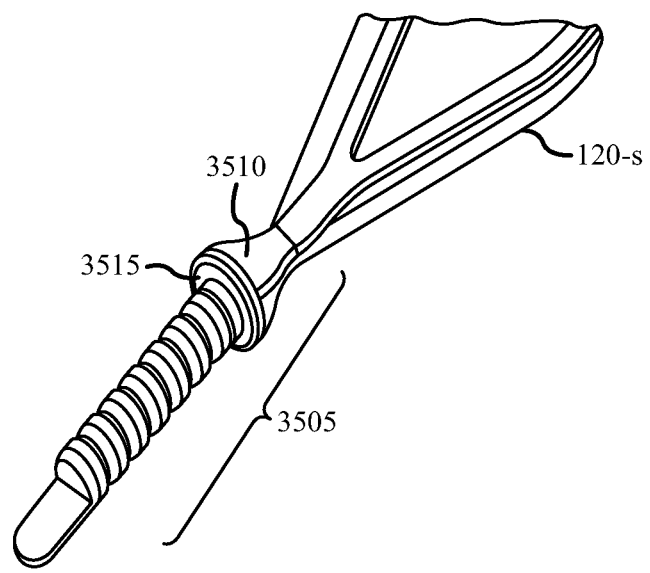
FIG. 22 is a perspective view of a distal plug according to various embodiments.

With reference to FIG. 22, a distal plug 3505 in accordance with various embodiments is shown. The distal plug 3505 may include a structure protruding from the proximal end of the expandable support device 120-s. The distal plug 3505 can include a ribbed portion which is inserted into the distal end of the first shaft of the guide assembly. The distal plug 3505 also may include a cone shaped section 3510 that creates a face edge 3515. This face edge 3515 can rest against the distal edge of the first shaft and is configured to be wider than the diameter of the distal end of the first shaft so that the cone shaped section 3510 cannot be inserted into the first shaft. The distal plug 3505 may be secured within the first shaft by conventional techniques such as glue, adhesives, or interference fit.

Figure 23:
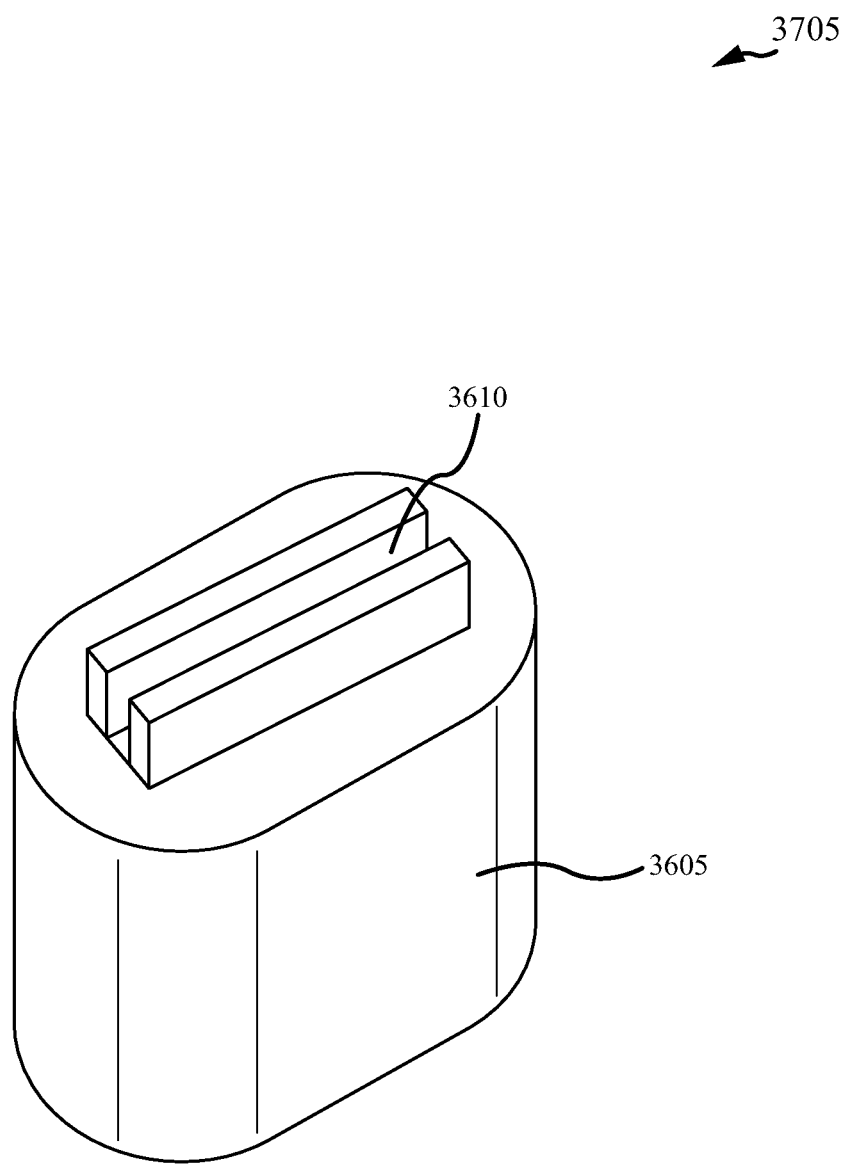
FIG. 23 is a perspective view of a torque member according to various embodiments.

FIG. 23 shows a torque member 3605 in accordance with various embodiments. The torque member 3605 may be configured for transmitting torque between the guide assembly and a locking member extending from a distal end of an expandable support device. The torque member 3605 can be rigid for enabling application of torque to rotate the expandable support device. The torque member 3605 may include a solid, rigid body and a slot 3610. The slot 3610 may have a thickness corresponding to the thickness of a locking member extending from a distal end of the an expandable support device such that the locking member can be securely received within the slot. In various embodiments, the torque member 3605 can have a width equal to or less than the diameter of the guide assembly at a distal end. The torque member 3605 can have a thickness slightly less than a width of the guide assembly at the distal end. Similarly, the locking member can have a thickness equal to or less than a width/diameter of the working channel. In this manner, the locking member may not need to fold or collapse during withdrawal and can be relatively rigid to enable torque transmission. As used herein, "thickness" refers to a direction into the page and "width" refers to a direction from left to right.

Figure 24A:
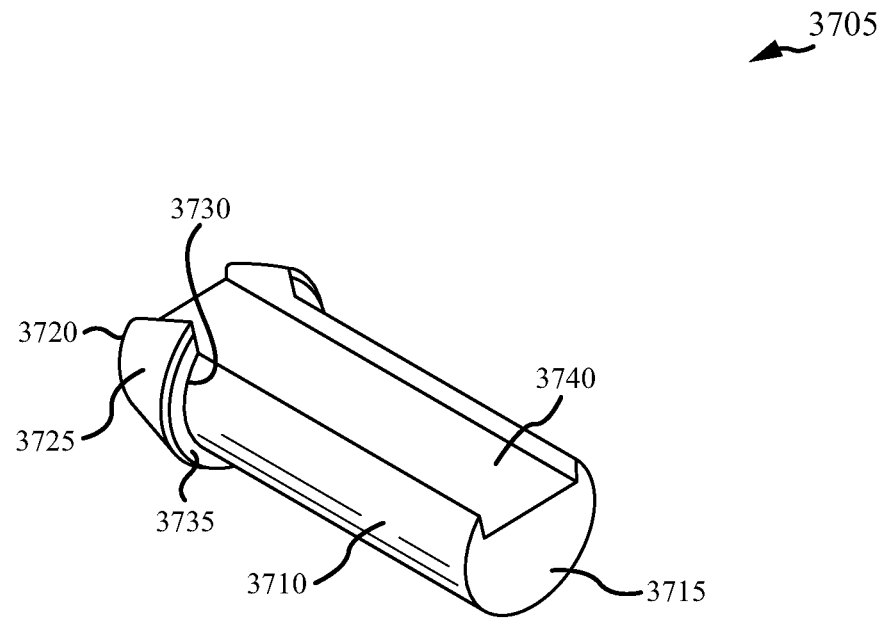
FIGS. 24A-24B are perspective and cross-section views, respectively, of a torque member according to various embodiments.
Figure 24B:
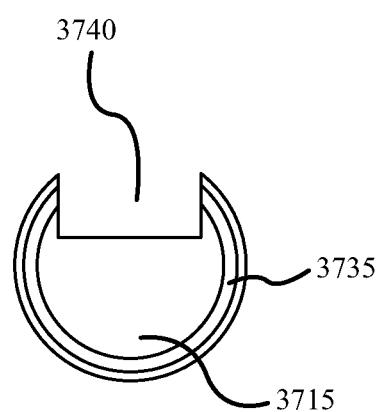

FIG. 24A and/or FIG. 24B show another torque member 3705 in accordance with various embodiments, which is configured for transmitting torque between the guide assembly and a locking member extending from a proximal end of an expandable support device. The torque member 3705 can be formed of a rigid material such as a thermoplastic. In some embodiments, the torque member is formed of polycarbonate.

The torque member 3705 can include a body 3710 having a proximal end 3715 and distal end 3720. The torque member 3705 can be shaped like a peg or a rod with a rounded surface along its length.

Distal end 3720 may be enlarged and may define a fitting portion 3725 of the torque member 3705. The fitting portion 3725 can extend from the distal end 3720 to a point between the distal end 3720 and proximal end 3715. The fitting portion 3725 can have a beveled outer surface with a distal edge having a smaller diameter than a proximal edge. The proximal edge of the fitting portion 3725 can include a breaking edge 3730 and a flat surface 3735. The fitting portion 3725 can be configured to be inserted into distal end of a first (i.e., distal) shaft such that breaking edge 3730 abuts a distal end of a first shaft. In various embodiments, the body 3710 has a shape and dimensions corresponding to the inner wall of the first shaft. In some embodiments, the distal and proximal edges of fitting portion 3725 are rounded to reduce the risk of damage, such as perforating, other components. The torque member 3705 may be secured within the first shaft by conventional techniques such as glue, adhesives, or interference fit.

The torque member 3705 can include a slot 3740 that extends the entire length of the torque member 3705. In various embodiments, the torque member 3705 has a length corresponding to the length of a locking member extending from the distal end of an expandable support device. The slot 3740 can have a width that corresponds to a width of the locking member. The width of the slot 3740 can be less than a width of the torque member 3705. The slot 3740 may be positioned at a distance above a centerline of the torque member 3705.

In some embodiments, the torque member 3705 has a length of about 0.2 inch. The torque member 3705 can have a width (diameter) of about 0.072 inch, and the fitting portion 3725 can have a maximum width (diameter) of about 0.09 inch. The beveled face of fitting portion 3725 can form an angle of about 15° from a longitudinal axis of the torque member 3705. The fitting portion 3725 can extend from an end of the torque member 3705 and have a length of about 0.039 inch. The slot 3740 can have a width of about 0.056 inch. A bottom of the slot 3740 can be positioned about 0.011 inch above a centerline of the torque member 3705. Other embodiments may include different dimensions.

The slot 3740 can be configured to allow interlocking of the torque member 3705 with a locking member extending from a distal end of a expandable support device. Referring to FIG. 12A, a locking member 1280 in accordance with various embodiments is illustrated. A throat section 1285 of the locking member 1280 can be held within the slot 3740 and locking section 1290 can be locked against a proximal end 3715 of the torque member 3705.

Figure 25A:
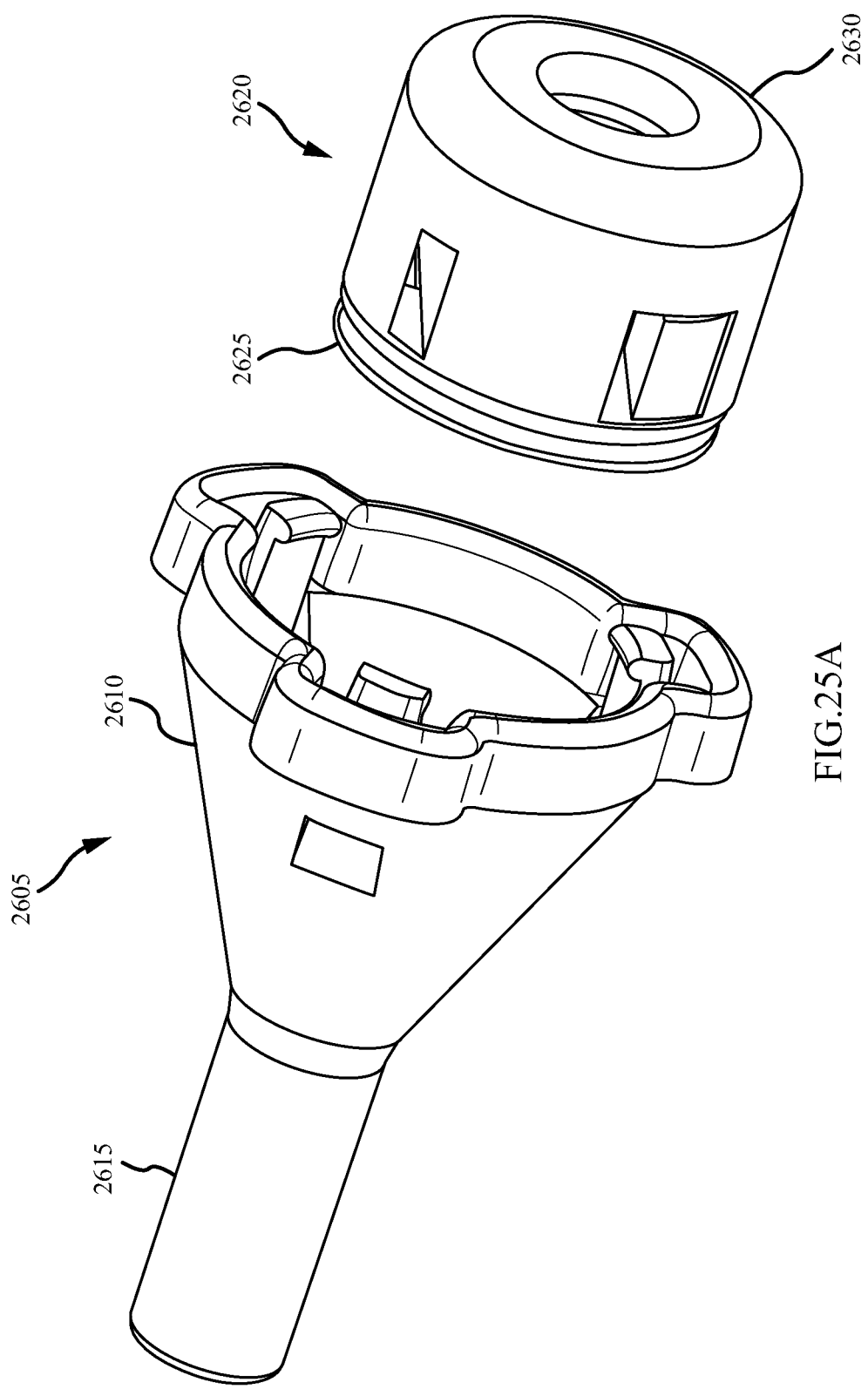
FIGS. 25A-25B are perspective views of an introducer according to various embodiments.
Figure 25B:
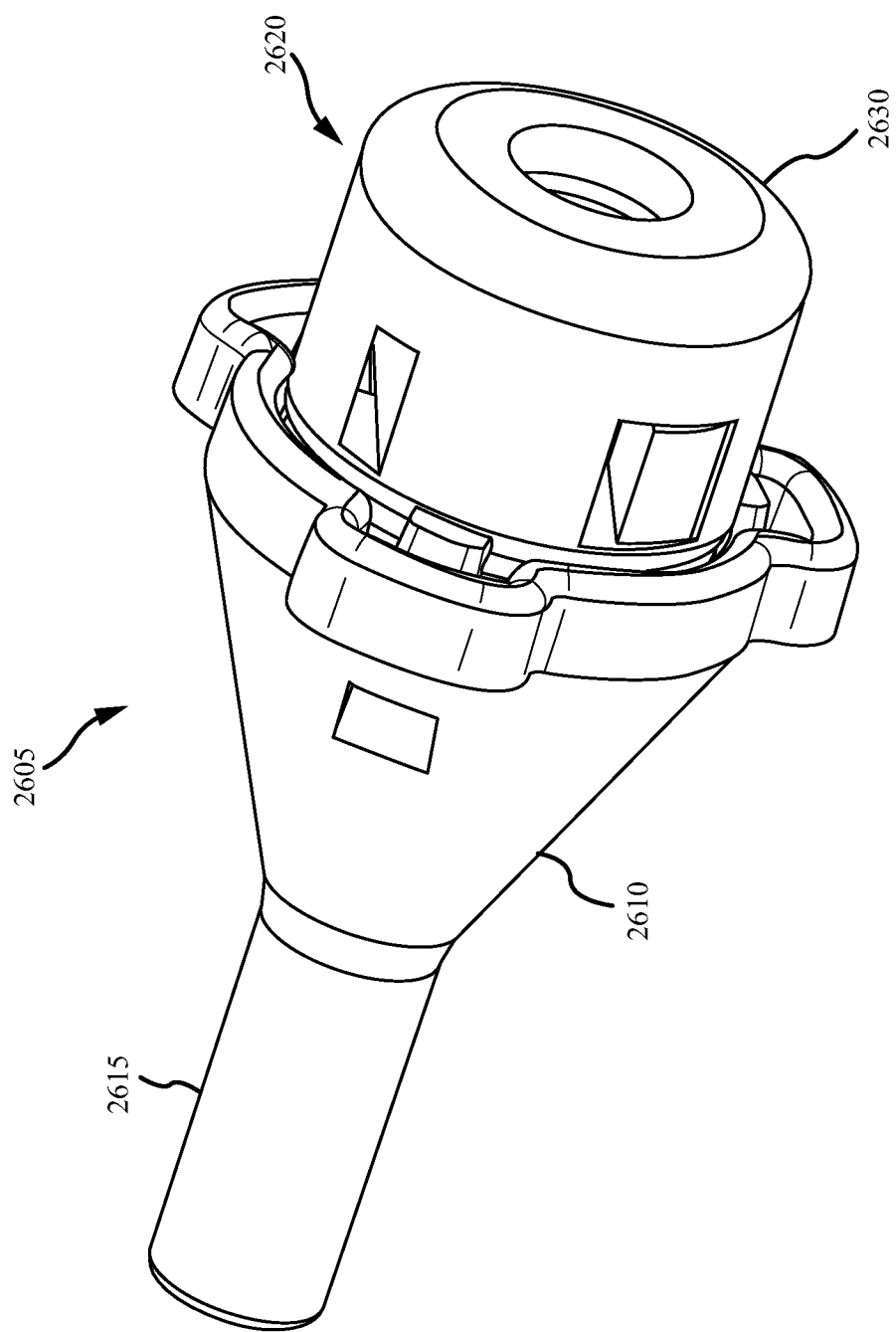

With reference to FIG. 25A and/or FIG. 25B, an introducer 2605 can be used in order to aid with the introduction of an expandable support device into a working channel, such as an endoscope. The introducer 2605 can include a conical section 2610 and a cylindrical section 2615, with a channel extending through both sections. The cylindrical section 2615 can have a uniform outer diameter which can be less than the diameter of an opening of a working channel such that the cylindrical section 2615 can be inserted into the opening of the working channel. In some embodiments, the outer diameter of the cylindrical section 2615 is smaller than the diameter of the working channel opening by only a small degree such that the cylindrical section 2615 fits flushly with the opening of the working channel when inserted in the working channel opening. The conical section 2610 can have a first diameter and a second diameter. The first diameter can be approximately the same as the diameter of the cylindrical section 2615. The second diameter can be larger than the first diameter, and the diameter of the conical section 2610 can increase from the first diameter to the second diameter to thereby form a cone shape. In some embodiments, the cylindrical section 2615 and the conical section 2610 are coaxially aligned.

When inserted in the working channel opening, the introducer 2605 can provide a wide mouth for inserting an expandable support device into a working channel. More specifically, the second diameter of the conical section 2610 can provide a wider area than the opening of the working channel to thereby make it easier for an operator to guide an expandable support device into a working channel.

In some embodiments, the introducer 2605 can be used in conjunction with an docking member 2620. In some embodiments, the docking member 2620 is part of a control element and/or protection element, such as protection element 165 of FIG. 1B. In some embodiments, the docking member 2620 is a separate device from the protection element, but can be coupled with the protection element. The docking member 2620 can have a first end 2625 and a second end 2630, with a channel extending through the docking member 2620 from the first end 2625 to the second end 2630. The first end 2625 can include a coupling mechanism configured for coupling the introducer 2605 with the docking member 2620. In some embodiments, the second diameter of the conical section 2610 includes a coupling mechanism that mates with the coupling mechanism on the first end 2625 of the docking member 2620. Any suitable coupling mechanism can be used to couple the introducer 2605 to the docking member 2620, including, but not limited to, a friction fit, male and female threading, or clips as shown in FIG. 25A. With reference to FIG. 25B, the introducer 2605 is shown coupled with the docking member 2620.

Figure 26A:
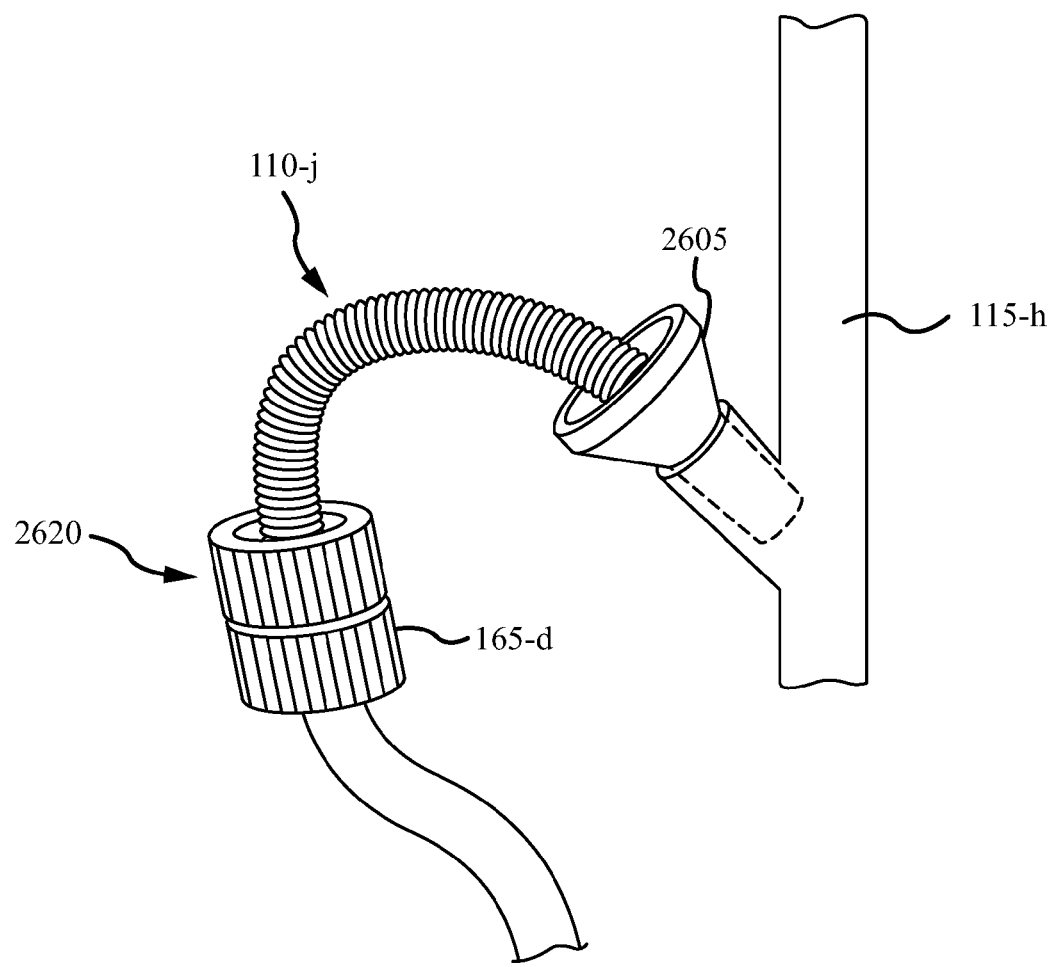
FIGS. 26A-26B are perspective views of an introducer according to various embodiments.
Figure 26B:
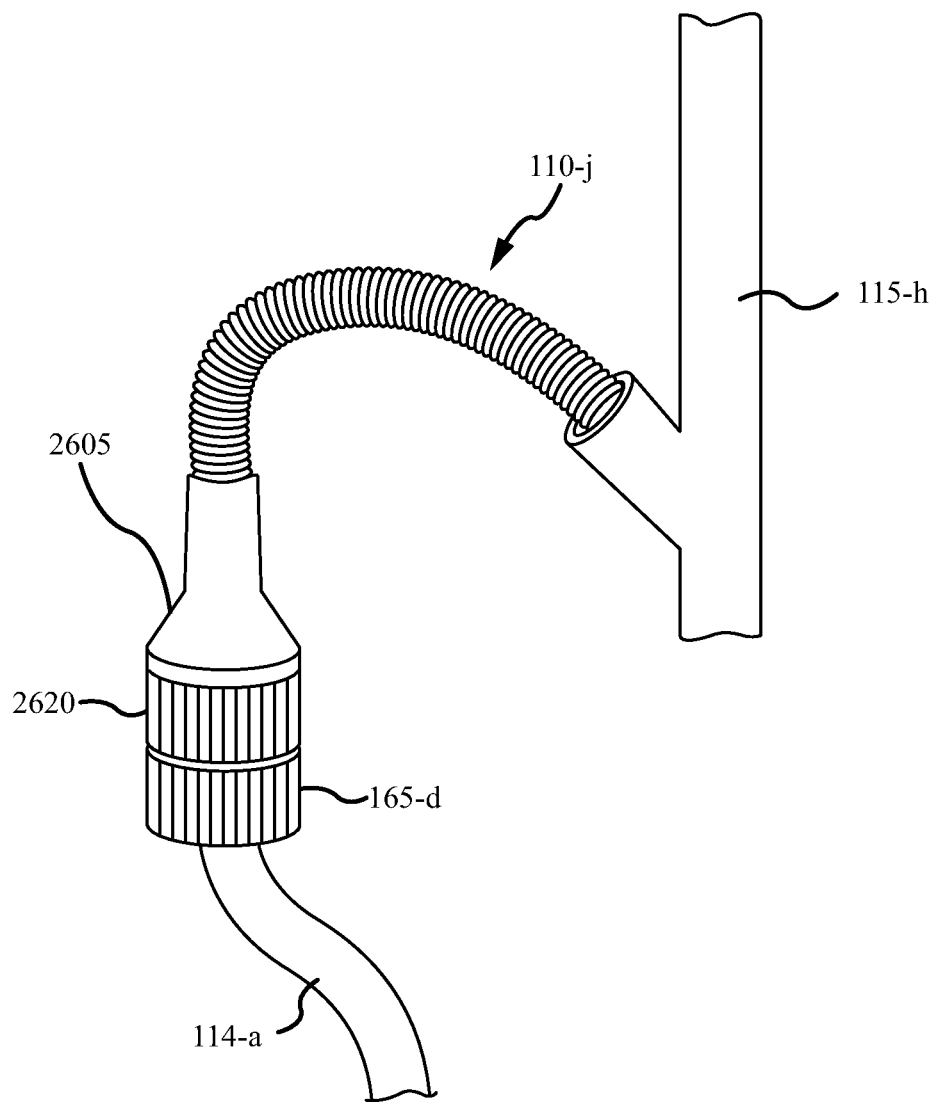

With reference to FIG. 26A and/or FIG. 26B, the docking member 2605 forms a part of the protection element 165-d such that the docking member 2605 and the protection element 165-d are a unitary body. The docking member 2605 can form the distal end of the protection element 165-d and can provide the protection element 165-d with the coupling mechanism used to couple the introducer 2605 to the protection element 165-d. As shown in FIG. 26A, the introducer 2605 can be inserted into an opening of a working channel 115-h and used to aid in the insertion of an expandable support device into the working channel 115-h. As shown in FIG. 26A, an expandable support device has been inserted into the working channel 115-h and a portion of the guide assembly 110-j remains outside of the working channel 115-h.

With reference to FIG. 26B, the introducer 2605 can be moved away from the working channel 115-h and towards the docking member 2620 of the protection element 165-d. The introducer 2605 generally slides along the guide assembly 110-j by virtue of the guide assembly 110-j passing through the channel of the introducer 2605. When the introducer 2605 reaches the docking member 2620 of the protection element 165-d, the coupling mechanism of each device can be used to couple the introducer 2605 to the protection element 165-d. In this manner, the introducer 2605 can be fixed to a location along the guide assembly 110-j and prevented from sliding back and forth along the guide assembly 110-j due to the protection element 165-d being fixed to the guide assembly 110-j as described in greater detail above. As a result, the introducer 2605 may not disturb the operator or interfere with manipulation of the expandable support device via the guide assembly 110-j and/or the protection element 165-d.

The manner in which the above described components of the treatment system are manufactured is generally not limited. With reference to FIGS. 27A-F, a method of constructing an operative member on an expandable support device and attaching the expandable support device to a flexible support in accordance with various embodiments is shown. In FIG. 27A, an expandable support device 120-t, such as a solid elastomeric body in the shape of a paddle is provided. In FIG. 27B, a layer of metallic layer 2705 is disposed on top of the expandable support device using any known technique. As shown in FIG. 27C, the metallic layer 2705 is then etched to form an operative member 160-e (for example, a pattern of electrodes) using any known technique, such as etching using masks. In FIG. 27D, a flexible support 155-n is provided, such as a nitinol flexible support. In FIG. 27E, an adhesive 2710, such as a silicone adhesive, is provided on a surface of the flexible support 155-n. In FIG. 27F, the combination of the expandable support device 120-t and the operative member 160-e is disposed on the adhesive 2710, and time and/or pressure is supplied to secure the combination of the expandable support device 120-t and the operative member 160-e to the flexible support 155-n. Other methods of constructing an operative member may also be utilized in some embodiments.

Figure 28A:
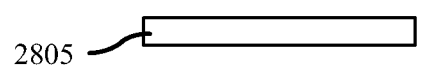
FIGS. 28A-28E are cross-section views of a method for making a patterned solid support and coupling it to an operative member according to various embodiments.

FIGS. 28A-28E are sequential views of a method of fabricating a patterned solid support and providing an operative member on top of the patterned solid support in accordance with various embodiments. FIG. 28A shows a solid support material 2805 for forming a patterned solid support in accordance with various embodiments. The solid support material 2805 can be a solid layer of material formed from a shape memory metal alloy such as nitinol. The solid support material 2805 may be formed into a thin, generally planar sheet using known processes such as cutting and rolling.

Figure 28B:
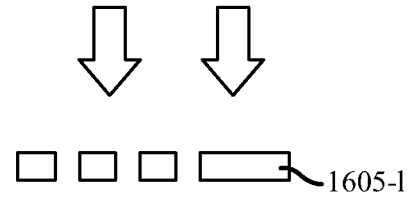

Next, solid support material 2805 is patterned using techniques to form patterned solid support 1605-l as shown in FIG. 28B in accordance with various embodiments. Examples of suitable patterning techniques include wet and dry etching, lithography, deposition, cutting, and milling.

The patterning may define splines in the patterned solid support 1605-*l*. The patterning may be performed simultaneously with the rolling.

Figure 28C:
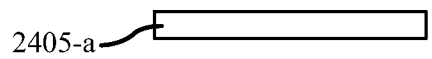
Figure 28D:
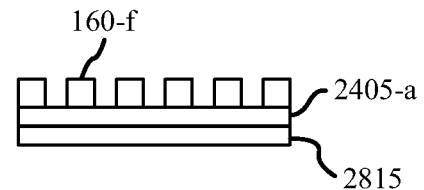

Next, the operative member is formed as shown in FIGS. 28C and 28D. In some embodiments, the operative member is a flexible circuit with RF electrodes. With reference to FIG. 28C, an insulator material 2405-*a* may be formed using conventional techniques. The exemplary insulator material 2405-*a* may be formed of a 0.001 inch adhesiveless polyimide sheet.

As shown in FIG. 28D, conductor material may then be added to the insulator material 2405-*a* and etched to form an operative member 160-*f* of electrodes. In this step, an adhesive 2815 can also applied to a back side to the insulator material 2405-*a*. For example, a thin acrylic and/or silicone sheet adhesive 2815 may be applied to the back of the insulator material 2405-*a*. In an exemplary embodiment, the pattern or electrodes is formed by laser etching.

Figure 28E:
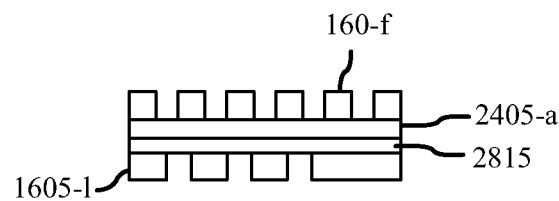

FIG. 28E shows the assembled operative member 160-*f* and patterned solid support 1605-*l* in accordance with various embodiments. As shown in 18E, the electrodes of the operative member 160-*f* may be positioned over splines of the patterned solid support 1605-*l*. FIG. 28E may be a simplified and exaggerated view of the patterned solid support 1605-*l* and operative member 160-*f*. In practice, for example, the relative thicknesses of the layers will vary. Other embodiments may be utilized in fabricating a patterned solid support and providing an operative member on top of the patterned solid support.

One will appreciate from the description herein that other processes may be used in the fabrication process. For example, the fabrication process may include one or more coating processes. For example, the any portion of the operative member may be coated with a material such as a bioactive agent. In various embodiments, the expandable support device is coated with a biomolecule such as a pharmaceutical agent, nucleic acid, amino acid, sugar, or lipid. In various embodiments, the expandable support device is coated with an antihyperplastic agent such as an antithrombotic agent (e.g. heparin), an antiplatelet agents (e.g. aspirin, arachidonic acid, and prostacyclin), or an antibody to platelet-derived growth factors. Other suitable biological coating materials and additives include endothelial cells, stem cells, and cell growth factors. In various embodiments, the operative member is coated with a biocompatible plastic such as polytetrafluoroethylene (PTFE), expanded PTFE (ePTFE), polypropylene, or poly(lactide). In various embodiments, the coating is only applied to the expandable support device so as not to interfere with functioning of the operative member. The expandable support device may be coated with a protective layer at any step in the process. For example, the expandable support device may be coated with a barrier layer to prevent oxidation or bioabsorption.

The fabrication process may also include other steps such as polishing, thermal treatments, and the like. The method of assembling the ablation device may implement other techniques and processes common in the material science, computer, and semiconductor fields. In some embodiments, the operative member is applied directly to the expandable support device via a conductive paint, molding, or laser etching.

Various embodiments of the systems described herein, including various embodiments of the individual components, can be used in a variety of ways. An embodiment of a particular method is described below.

In a first step, a clinician may perform a general clinical assessment. This assessment may include assessing the disease target, the type of necessary treatment, and the mode of delivery of the treatment device. Based on the clinical assessment, the clinician may select a proper treatment device. For example, a kit may be provided with multiple operative members configured for different treatments. The kit may include multiple ablation devices, each with differently-sized treatment surfaces, electrode configurations, treatment modalities, etc. The clinician may select a larger ablation device from the kit if the disease target is large. The kit may include an ablation device for treating larger or smaller circumferential sections of the body lumen, for example, a 90 degree section or a 120 degree section.

Once the operative member has been selected, the clinician may assemble the system. In one example, the kit includes a guide assembly, and multiple expandable support devices having varying operative members disposed thereon. The clinician may slide the selected expandable support device onto a distal end of the guide assembly and secures it in place. In another example, the kit may include multiple pre-assembled systems, each with a guide assembly and an attached expandable support device-operative member combo. In yet another example, the system may include an expandable support-operative member combo configured for treating a variety of disease targets (e.g. one-size-fits-all).

Once the system is prepared, the clinician may insert the expandable support device-operative member combo through a cap at a proximal end of a working channel, such as an endoscope. At this stage the endoscope may be already inserted and positioned in the patient's body. Typically the distal end of the endoscope is positioned adjacent a target site using conventional techniques.

The expandable support device-operative member combo may be inserted distal end first. The expandable support device-operative member combo can be pre-biased in the expanded configuration, in which case it may need to be collapsed to fit into the smaller working channel. The clinician may gently squeeze the expandable support device-operative member combo to collapse it for insertion. An introducer may be utilized in some cases. The rounded distal tip of the expandable support device-operative member combo may aid in rolling the device into the working channel. Once the distal end of the expandable support device-operative member combo is inserted, the clinician eases the rest of the expandable support device-operative member combo into the working channel.

Next, the clinician may push the expandable support device-operative member combo through working channel in the collapsed configuration using guide assembly. The clinician can axially move the expandable support device-operative member combo through the channel like a pipe cleaner using the guide assembly.

The length of the guide assembly may be matched to the length of the endoscope such that a protection element or handle element is located just proximal the endoscope cap at the entry of the endoscope when the expandable support device-operative member combo is fully inserted. The clinician may use an introducer to assist with insertion. The protection or handle element can be larger than the endoscope working channel and thus acts as an insertion stop. The protection or handle element can also act as a visual clue to the user of the expandable support device-operative member combo position at an opposite end. As the protection or handle element approaches the cap of the endoscope, the user can gauge the position of the expandable support device-operative member combo relative to the distal most end of the endoscope.

The guide assembly may be oversized to accommodate insertion into a variety of endoscopes and other delivery lumens. In various embodiments, exemplary an elongated rigid portion extending off the distal end of a protection or handle element can be used for axial positioning adjustment with various working channel lengths. As the user pushes and pulls the protection or handle element, the rigid section may remain positioned in the working channel. The rigidity of rigid section can allow for easier axial movement without binding the guide assembly on the inner wall of the working channel.

The system may be configured for use with a variety of lumens and treatment sites including, but not limited to, the gastrointestinal tract (GI tract), respiratory tract, ear canal, urinary tract, biliary system and bile duct, female reproductive system, organs in the chest (e.g., heart), epidural space, maxillary and face, and hand. The system may be configured for a variety of therapies and procedures using an endoscope including, but not limited to, esophagogastroduodenoscopy (e.g., esophagus, stomach, and duodenum); enteroscopy (e.g., small intestine); colonoscopy or sigmoidoscopy (e.g., large intestine and colon); magnification endoscopy; endoscopic retrograde cholangiopancreatography (ERCP), duodenoscope-assisted cholangiopancreatoscopy, or intraoperative cholangioscopy (e.g., bile duct); rhinoscopy (e.g., nose); bronchoscopy (e.g., lower respiratory tract); cystoscopy (e.g. urinary tract); rectoscopy (e.g. rectum); anoscopy (e.g., anus); proctoscopy; plastic surgery; orthopedic surgery (e.g., hand surgery like endoscopic carpal tunnel syndrome and epidural space); endodontic surgery; gynoscopy, colposcopy (e.g., cervix), hysteroscopy (e.g., uterus), and falloscopy (e.g. fallopian tubes); laparoscopy; arthroscopy (e.g., interior of a joint); thoracoscopy and mediastinoscopy; amnioscopy; and fetoscopy. The system may be configured for a variety of therapies and procedures using other instruments including, but not limited to, dialysis, catheterization, angioplasty, balloon-based procedures (e.g., balloon septostomy and balloon sinuplasty), electrophysiology, monitoring (e.g., cardiac monitoring), drug delivery, and ear wax removal and treatment of cerumen impaction.

The endoscope, or other device that includes a working channel such as a catheter, can be inserted into the body using conventional techniques. For example, the endoscope may be inserted through a body orifice or through an incision site (e.g., laparoscopy). As may be appreciated from the description herein, the system may be used in conjunction with other instruments having a lumen such as a catheter, a robotic surgical instrument, and more.

Typically the working channel may be routed through a body cavity, duct, or vessel to a treatment site. The clinician optionally confirms the working channel distal end is properly positioned at the treatment site before deploying expandable support device-operative member combo. Once the position is confirmed, the clinician may proceed to deploy the expandable support device-operative member combo.

The system can allow for easy and accurate deployment of the expandable support device-operative member combo. The clinician may axially move the protection or handle element so expandable support device-operative member combo is moved out of a distal end of working channel. As the expandable support device-operative member combo extends outside the working channel, the expandable support device-operative member combo may be released from the working channel wall. The expandable support device-operative member combo self-expands from the collapsed configuration to the expanded configuration without any other significant action on the part of the clinician. The clinician may only need to move the protection or handle element close to the cap to ensure the expandable support device-operative member combo has been deployed at the distal end. The natural "spring" force of the expandable support device against the channel wall may also provide haptic feedback to the user to confirm deployment.

In various embodiments, the expandable support device-operative member combo is configured to self-expand to the expanded configuration once it unrestrained. In various embodiments, the expandable support device-operative member combo is substantially planar in the expanded configuration. In various embodiments, the plane of the expanded expandable support device-operative member combo is substantially parallel to the target treatment surface. In various embodiments, the plane of the expanded expandable support device-operative member combo is substantially parallel to the longitudinal axis of the guide assembly.

The torqueable guide assembly may allow the expandable support device-operative member combo to be rotated during or after expansion. The user can easily rotate the expandable support device-operative member combo by rotating, for example, the protection or handle element. Because first shaft is rotationally decoupled from second shaft, the expandable support device-operative member combo can be rotated independently of the second shaft. In an exemplary embodiment, the second shaft is attached to a stationary power source and control unit. Thus, the expandable support device-operative member combo can be rotated without developing kinks and rotational stress.

In various embodiments, after expansion, the user rotates the expandable support device-operative member combo so the treatment surface faces the tissue surface. The protection or handle element also allows a user to rotate the expandable support device-operative member combo after treatment to treatment other areas of tissue. The user may affect desired contact of expandable support device-operative member combo with the treatment site by deflecting the distal end of endoscope. The user may affect contact by deflecting the expandable support device-operative member combo using guide assembly. For example, the protection or handle element may be manipulated to extend the expandable support device-operative member combo away from an end of the endoscope and toward the treatment site.

Once the expandable support device-operative member combo is positioned at treatment site, the clinician can administer treatment using the expandable support device-operative member combo. The clinician may activate the power source to deliver energy through the operative member (such as through electrodes). In various embodiments, the power source performs a pre-programmed treatment protocol. In various embodiments, the power source is manually controlled.

After energy delivery, the clinician may determine whether follow-up treatment is necessary. If so, the treatment site can be prepared for follow-on treatment. For example, the treated tissue can be cleaned away with a cleaning device. The cleaning device may comprise a cleaner attached to the expandable support device-operative member combo. An example of a cleaning device for use with an expandable support device-operative member combo is disclosed in U.S. Patent Pub. No. 2009/0036886 to Utley et al., the entire contents of which is incorporated herein by reference for all purposes.

After treatment is complete, the clinician may pull on protection or handle element to retract the expandable support device-operative member combo. As the expandable support device-operative member combo is withdrawn, a portion of a tapered edge of expandable support device-operative member combo may contact the working channel. As the expandable support device-operative member combo is withdrawn further, the tapered edge may slide against the working channel wall such that a collapsing or rolling force is applied to the expandable support device. This force may cause the expandable support device, and consequently the operative member disposed thereon, to retract back into the collapsed configuration as it is pulled into the working channel.

The fully retracted expandable support device-operative member combo can be repositioned safely while in the working channel. The expandable support device-operative member combo device can then be repositioned at a second treatment location using the endoscope. Once the endoscope is repositioned, the expandable support device-operative member combo may be re-expanded out of an end of the endoscope as described above. Alternatively, the expandable support device-operative member combo can be repositioned through the working channel. For example, the clinician can move the expandable support device-operative member combo axially and/or rotate the expandable support device-operative member combo using protection or handle element. When treatment is complete, the expandable support device-operative member combo can be fully retracted and removed from the proximal end of the endoscope.

Figure 29:
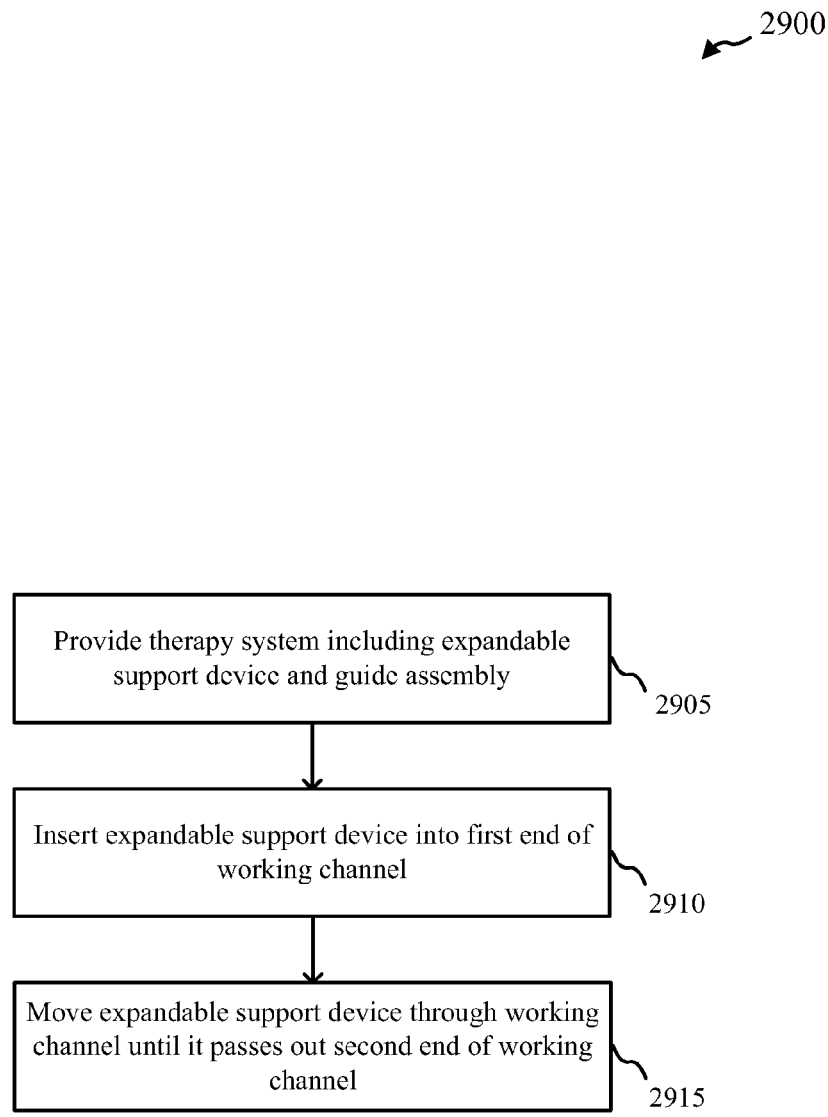
FIG. 29 is a flow diagram illustrating a method for using a therapy system according to various embodiments.

With reference to FIG. 29, a general method 2900 of using various embodiments of the systems and/or devices described herein is shown in accordance with various embodiments. For example, method 2900 may be implemented utilizing the various embodiments of system 100, expandable support element 120, guide assembly 110, operative member 160, and/or other devices and/or components. At block 2905, a therapy system is provided. The system can include any embodiments of the therapy system described herein, including any embodiment of the individual components of the system described herein. Generally, the system will include an expandable support device, optionally with an operative member disposed thereon, a guide assembly to which the expandable support device is coupled at a distal end of the guide assembly, and a working channel configured for receiving the expandable support device and the guide assembly.

At block 2910, the expandable support device is inserted into a first end of the working channel. In some embodiments, the expandable support device is positioned in a collapsed position prior to inserting the expandable support device into the working channel. The distal end of the expandable support device can be rounded for further aid in the insertion of the expandable support device into the working channel.

At block 2915, the expandable support device is moved through the working channel until the expandable support device emerges out of a second end of the working channel. The guide assembly can be used to aid in the movement of the expandable support device through the working channel and out of the second end of the working channel. In some embodiments, the expandable support device will self transition into an expanded configuration after it passes out of the second end of the working channel.

After the expandable support device passes out of the working channel, an optional step can be performed wherein a portion of the guide assembly is rotated to provide torque to the expandable support device. In some embodiments, the first shaft portion of the guide assembly is rotated to provide torque to the expandable support device. The first shaft can be rotationally independent of the second shaft.

Other additional steps that can be performed after the method illustrated in FIG. 29 or any of the methods illustrated in FIGS. 30, 31, 32, 33, 34, and/or 35 can include deflecting the working channel and bringing the expandable support device (which may have an operative member disposed thereon) into contact with a target treatment area and/or providing an apposition force via the expandable support device (and optionally the flexible support coupled with the expandable support device), and/or delivering energy to the target treatment area. Other steps may also be utilized in accordance with various embodiments.

Figure 30:
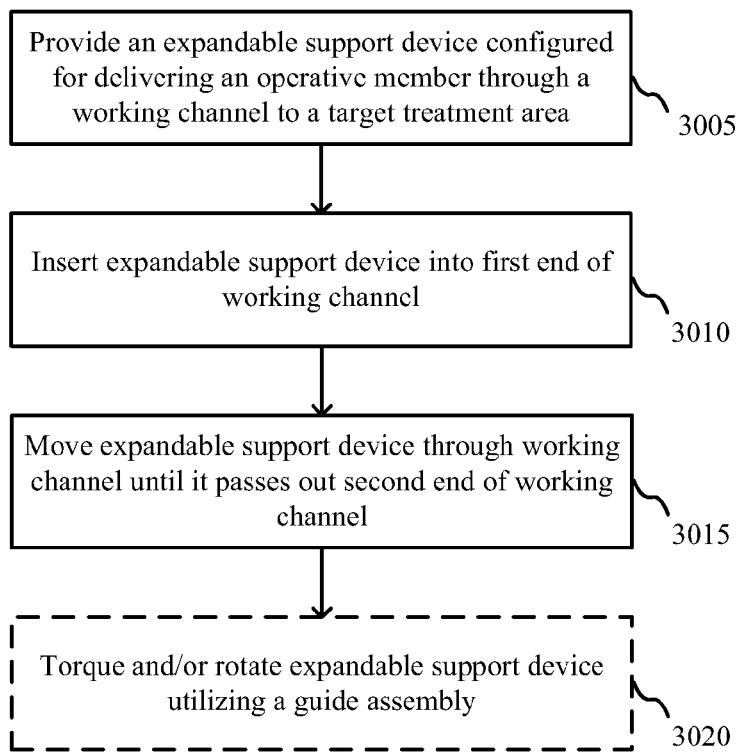
FIG. 30 is a flow diagram illustrating a method for delivering an expandable support device to a target treatment area according to various embodiments.

With reference to FIG. 30 a general method 2900 of using various embodiments of the systems and/or devices described herein is shown in accordance with various embodiments. For example, method 3000 may be implemented utilizing the various embodiments of system 100, expandable support element 120, guide assembly 110, operative member 160, and/or other devices and/or components. Method 3000 may provide for delivering an expandable support device to a target treatment area. Method 3000 may be an example of method 2900 of FIG. 29.

At block 3005, an expandable support device configured for delivering an operative member through a working channel to a target treatment area may be provided. The expandable support device may include an elastomeric body configured to support an operative member. The elastomeric body may include: a proximal portion configured for coupling the elastomeric body with a guide assembly; a distal portion opposite the proximal portion; and a central axis extending between the distal portion and the proximal portion of the elastomeric body. The expandable support device may include one or more supports coupled with the elastomeric body and aligned parallel to the central axis, where at least one of the supports includes a superelastic material.

At block 3010, the expandable support device may be inserted into a first end of the working channel. At block 3015, the expandable support device may be moved through the working channel until the expandable support device passes out of a second end of the working channel.

Some embodiments of method 3000 may include a block 3020 where the expandable support device is torque and/or rotated utilizing the guide assembly. Some embodiments include positioning the expandable support device into a collapsed position prior to inserting the expandable support device into the working channel.

Figure 31:
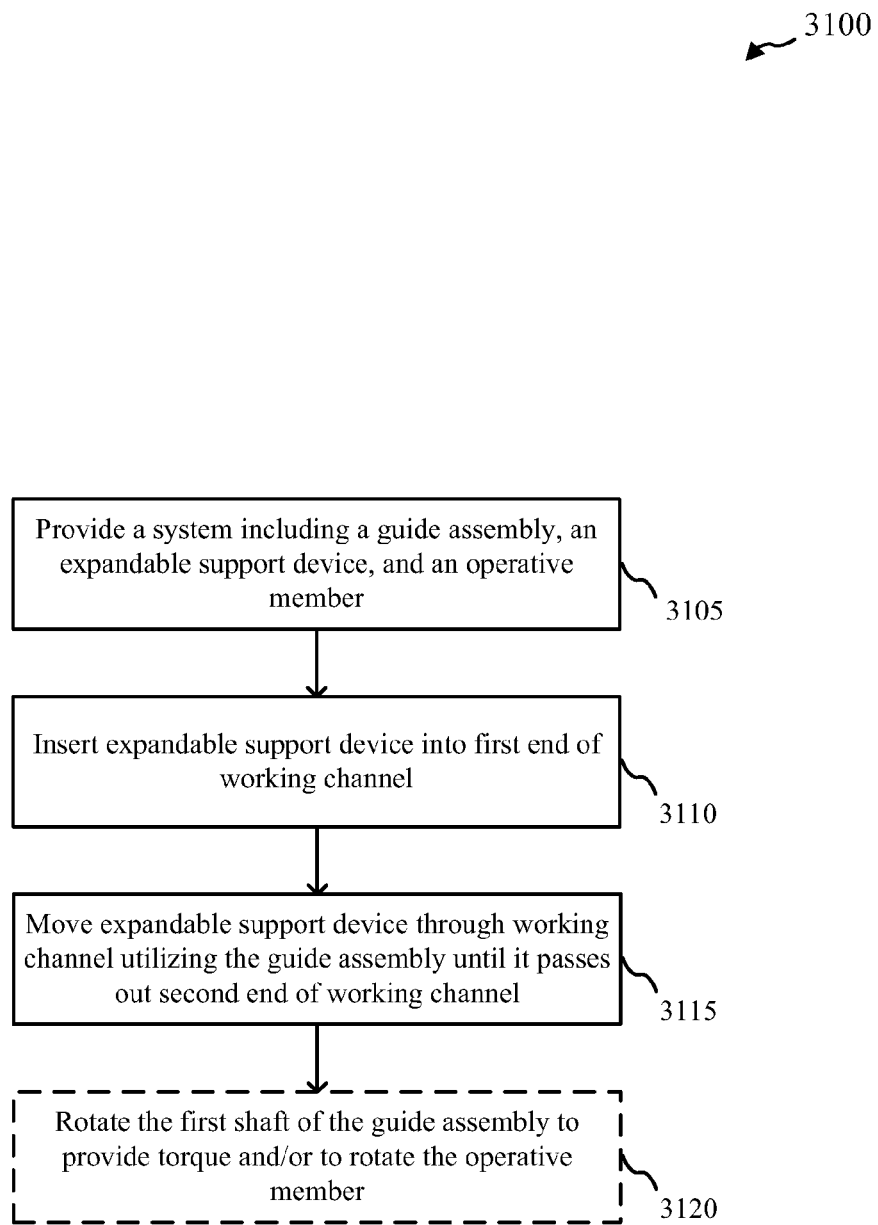
FIG. 31 is a flow diagram illustrating a method for utilizing a guide assembly for delivering an operative member to a target treatment according to various embodiments.

With reference to FIG. 31 a general method 3100 of using various embodiments of the systems and/or devices described herein is shown in accordance with various embodiments. For example, method 3100 may be implemented utilizing the various embodiments of system 100, expandable support element 120, guide assembly 110, operative member 160, and/or other devices and/or components. Method 3100 may provide for utilizing a guide assembly for delivering an operative member to a target treatment. Method 3100 may be an example of method 2900 of FIG. 29.

At block 3105, a system including a guide assembly may be provided. The guide assembly may be configured for delivering and positioning the operative member through a working channel to the target treatment area. The guide assembly may include: one or more transmission lines for operatively connecting the operative member to a power source; a first shaft enclosing at least a first portion of the one or more transmission lines, the first shaft configured for transmitting torque to the operative member; and a second shaft enclosing at least a second portion of the transmission lines. The first shaft and the second shaft may be configured to allow the first shaft to rotate independently of the second shaft. The system may include an expandable support device configured to deliver the operative member through the working channel to the target treatment area and coupled with a distal end of the guide assembly. The system may include an operative member coupled with the expandable support device.

At block 3110, the expandable support device may be inserted into a first end of the working channel. At block 3115, the expandable support device may be moved through the working channel utilizing the guide assembly until the expandable support device passes out of a second end of the working channel. In some embodiments, the expandable support device may be positioned into a collapsed position prior to inserting the expandable support device into the working channel. Some embodiments may include a block 3120 that may include rotating the first shaft of the guide assembly to provide torque to the operative member.

Figure 32:
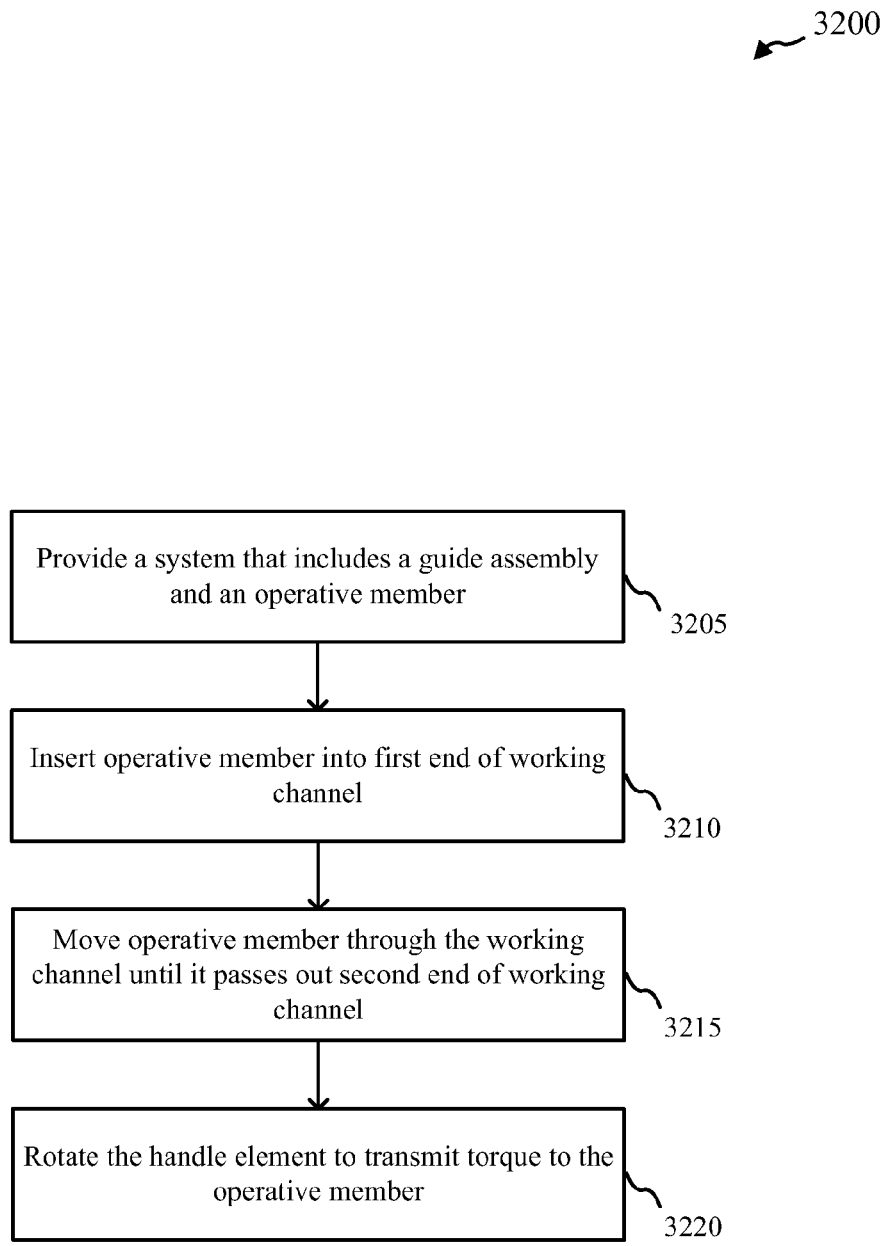
FIG. 32 is a flow diagram illustrating a method for delivering an operative member to a target treatment area according to various embodiments.

With reference to FIG. 32, a general method 3200 of using various embodiments of the systems and/or devices described herein is shown in accordance with various embodiments. For example, method 3200 may be implemented utilizing the various embodiments of system 100, expandable support element 120, guide assembly 110, operative member 160, and/or other devices and/or components. Method 3200 may deliver an operative member to a target treatment area. Method 3200 may be an example of method 2900 of FIG. 29.

At block 3205, a system may be provided that includes a guide assembly. The guide assembly may include: one or more transmission lines for operatively connecting an operative member to a power source; a flexible shaft enclosing at least a portion of the one or more power transmission lines, the first shaft configured for transmitting torque to the operative member; and a handle element comprising a body and a channel extending through the body and through which the flexible shaft passes, the handle element configured such that the flexible shaft moves through the channel. The system may also include an operative member coupled with a distal end of the flexible shaft.

At block 3210, the operative member may be inserted into a first end of a working channel. At block 3215, the operative member may be moved through the working channel until the operative member passes out of the second end of the working channel. At block 3220, the handle element may be rotated to transmit torque to the operative member. Some embodiments may include positioning the operative member into a collapsed position prior to inserting the operative member into the working channel.

Figure 33:
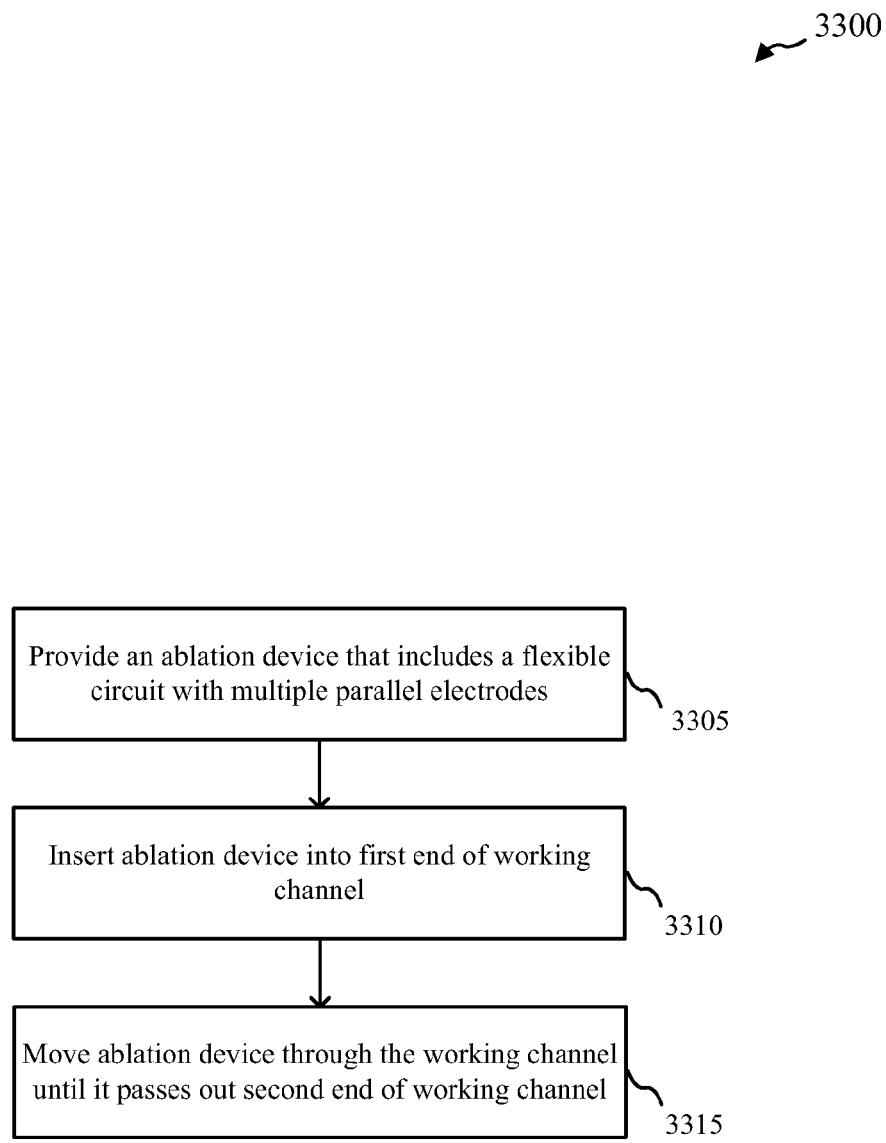
FIG. 33 is a flow diagram illustrating a method for delivering an ablation device to a target treatment area according to various embodiments.

With reference to FIG. 33, a general method 3300 of using various embodiments of the systems and/or devices described herein is shown in accordance with various embodiments. For example, method 3300 may be implemented utilizing the various embodiments of system 100, expandable support element 120, guide assembly 110, operative member 160, and/or other devices and/or components. Method 3300 may deliver an ablation device to a target treatment area. Method 3300 may be an example of method 2900 of FIG. 29.

At block 3305, an ablation device may be provided. The ablation device may include a flexible circuit configured to transition between a collapsed configuration and an expanded configuration. The flexible circuit may include multiple parallel electrodes configured to collapse around an axis parallel to the multiple parallel electrodes.

At block 3310, the ablation device may be inserted into a first end of a working channel. At block 3315, the ablation device may be moved through the working channel until the ablation device passes out of a second end of the working channel. Some embodiments of method 3300 include positioning the flexible circuit into a collapsed configuration prior to inserting the ablation device into the working channel.

Figure 34:
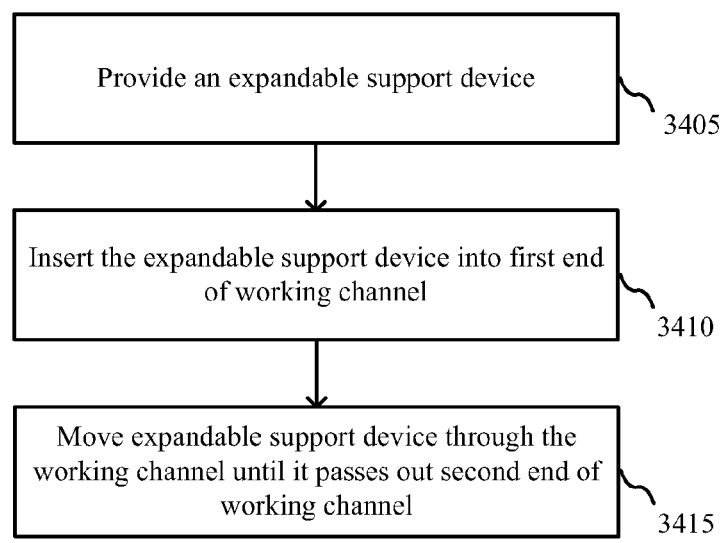
FIG. 34 is a flow diagram illustrating a method for delivering an expandable support device to a target treatment area according to various embodiments.

With reference to FIG. 34, a general method 3400 of using various embodiments of the systems and/or devices described herein is shown in accordance with various embodiments. For example, method 3400 may be implemented utilizing the various embodiments of system 100, expandable support element 120, guide assembly 110, operative member 160, and/or other devices and/or components. Method 3400 may deliver an expandable support device to a target treatment area. Method 3400 may be an example of method 2900 of FIG. 29.

At block 3405, an expandable support device may be provided. The expandable support device may include: a solid support member comprising a perimeter and superelastic properties; and multiple splines formed in a pattern interior to the perimeter of the solid support member and multiple voids between adjacent splines. A width and a spacing of the multiple splines may be configured to promote expansion of the support member between a collapsed configuration and an expanded configuration providing a substantially planar support surface.

At block 3410, the expandable support device may be inserted into a first end of a working channel. At block 3415, the expandable support device may be moved through the working channel until the expandable support device passes out of a second end of the working channel. In some embodiments, the expandable support device is positioned into a collapsed configuration prior to inserting the expandable support device into the working channel.

Figure 35:
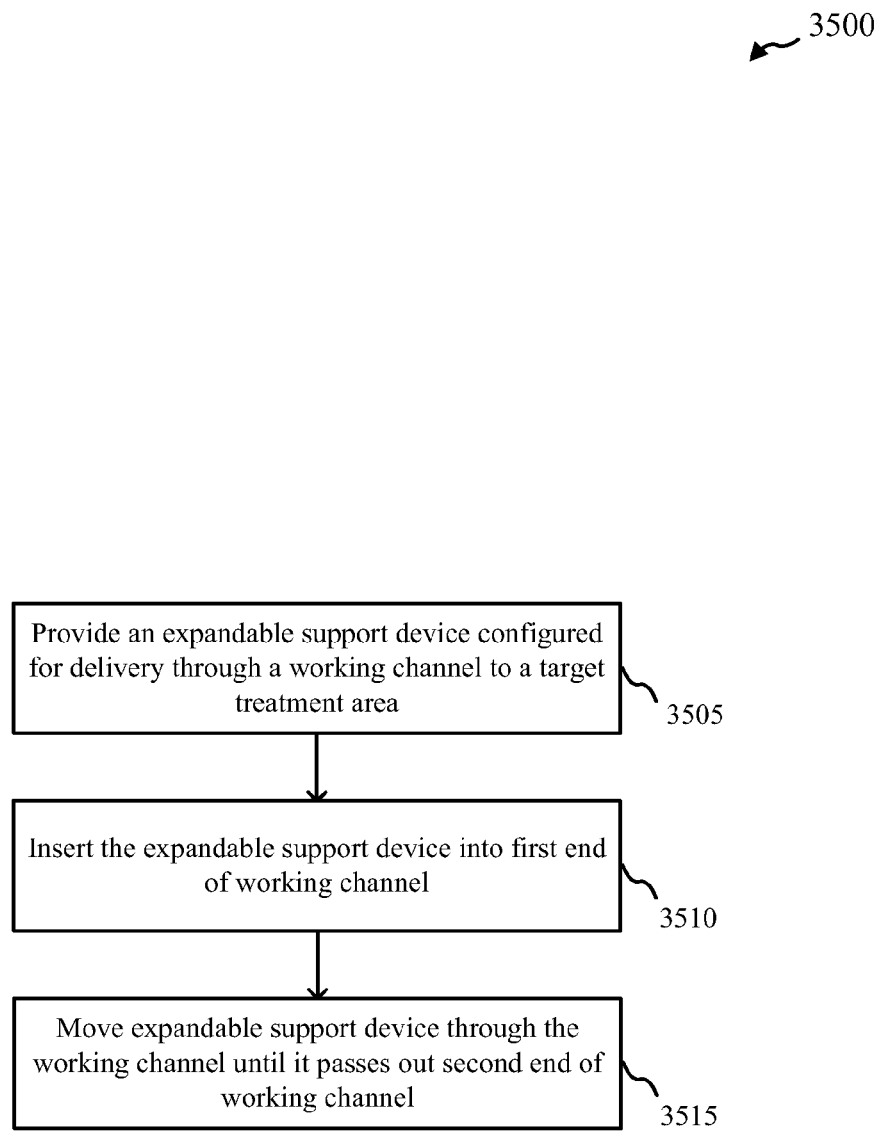
FIG. 35 is a flow diagram illustrating a method for delivering an expandable support device to a target treatment area according to various embodiments.

With reference to FIG. 35, a general method 3500 of using various embodiments of the systems and/or devices described herein is shown in accordance with various embodiments. For example, method 3500 may be implemented utilizing the various embodiments of system 100, expandable support element 120, guide assembly 110, operative member 160, and/or other devices and/or components. Method 3500 may deliver an expandable support device to a target treatment area. Method 3500 may be an example of method 2900 of FIG. 29.

At block 3505, an expandable support device configured for delivery through a working channel to a target treatment area may be provided. The device may include: an expandable support member configured for supporting an operative member, the support member comprising multiple splines having a width and a spacing selected to promote expansion of the support member between a collapsed configuration and an expanded configuration. A portion of the support member may define a substantially planar surface in the expanded configuration.

At block 3510, the expandable support device may be inserted into a first end of the working channel. At block 3515, the expandable support device may be moved through the working channel until the expandable support device passes out of a second end of the working channel. Some embodiments include positioning the expandable support device into a collapsed position prior to inserting the expandable support device into the working channel.

The foregoing description provides examples, and is not intended to limit the scope, applicability or configuration of the various embodiments. Rather, the description and/or figures provide those skilled in the art with an enabling description for implementing various embodiments. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, and devices, may individually or collectively be components of a larger system, wherein other procedures may take precedence over or otherwise modify their application.

The foregoing descriptions of specific embodiments have been presented for purposes of illustration and description. They are not intended to be exhaustive or to limit the invention to the precise forms disclosed, and obviously many modifications and variations are possible in light of the above teaching. The embodiments were chosen and described in order to explain the principles of the various embodiments and its practical application, to thereby enable others skilled in the art to utilize the various embodiments with various modifications as are suited to the particular use contemplated. It is intended that the scope of the various embodiments be defined by the Claims appended hereto and their equivalents.

The invention claimed is:

1. An expandable support device configured for delivery through a working channel and to a target treatment area, comprising:
    a support member comprising a perimeter and highly elastic or superelastic properties; and
    a plurality of splines formed in a pattern interior to the perimeter of the support member and a plurality of voids between adjacent splines of the plurality of splines, wherein a width and a spacing of the plurality of splines is configured to promote expansion of the support member between a collapsed configuration and an expanded configuration providing a support surface,
    wherein the expandable support device further comprises an operative member comprising a flexible circuit disposed on the support member and capable of bending with the support member on which it is disposed.

2. The device of claim 1, wherein the support member comprises a proximal end, a distal end, and a central axis extending from the proximal end to the distal end, and wherein the pattern of the plurality of splines comprises:
    a central axis spline substantially overlapping the central axis of the support member;
    a first subset of splines extending from the central axis spline towards a first lateral peripheral edge of the support member;
    a second subset of splines extending from the central axis spline towards a second lateral peripheral edge of the support member opposite the first lateral peripheral edge.

3. The device of claim 2, wherein the first subset of splines and the second subset of splines have a thickness less than a thickness of the central axis spline.

4. The device of claim 2, wherein the first subset of splines is arranged in parallel to one another and the second subset of splines is arranged in parallel to one another.

5. The device of claim 4, wherein the first subset of splines and the second subset of splines extend from the central axis spline at an angle such that the first and the second subsets of splines extend from the central axis spline towards the distal end of the support member.

6. The device of claim 5, wherein the first subset of splines and the second subset of splines extend from the central axis spline at an angle in the range of from greater than 0 degrees to 90 degrees.

7. The device of claim 5, wherein the first subset of splines and the second subset of splines extend from the central axis spline at an angle of about 45 degrees.

8. The device of claim 1, wherein the support member comprises of a metal having shape memory properties.

9. The device of claim 1, wherein the support surface defines a predetermined shape corresponding to a tissue surface at a treatment site in a patient.

10. The device of claim 1, wherein a thickness of the support member is about 0.003 inch.

11. The device of claim 1, wherein the pattern of the plurality of splines comprises a plurality of equally spaced vertical splines interconnected by horizontal splines.

12. The device of claim 1, wherein the operative member is supported by the plurality of splines.

13. The device of claim 12, wherein the operative member extends across an entire width of the support member.

14. The device of claim 1, wherein the operative member is coupled with the plurality of splines with an elastomeric adhesive.

15. The device of claim 1, wherein the flexible circuit comprises: a plurality of electrodes patterned to mirror the pattern of the plurality of splines.

16. The device of claim 1, wherein the support member includes a rounded distal edge.

17. The device of claim 1, wherein the support member includes a tapered proximal edge for promoting retraction of the device into the working channel.

18. A system for delivering treatment to a target area comprising:
    a support member comprising a perimeter and at least a highly elastic or superelastic properties;
    a plurality of splines formed in a pattern interior to the perimeter of the support member and a plurality of voids between adjacent splines of the plurality of splines, wherein a width and a spacing of the plurality of splines is configured to promote expansion of the support member between a collapsed configuration and an expanded configuration providing a support surface; and
    an operative member wherein the operative member comprises a flexible circuit disposed on the support member and capable of bending with the support member on which it is disposed.

19. The system of claim 18, wherein the support member has a first surface and a second surface opposite the first surface, and wherein the plurality of splines are disposed on the first surface and the operative member is disposed on the second surface.

20. A method of delivering an expandable support device to a target treatment area comprising:
    providing the expandable support device comprising:

a support member comprising a perimeter and highly elastic or superelastic properties; and a plurality of splines formed in a pattern interior to the perimeter of the support member and a plurality of voids between adjacent splines of the plurality of splines, wherein a width and a spacing of the plurality of splines is configured to promote expansion of the support member between a collapsed configuration and an expanded configuration providing a support surface, wherein the expandable support device further comprises an operative member comprising a flexible circuit disposed on the support member and capable of bending with the support member on which it is disposed;

inserting the expandable support device into a first end of a working channel; and moving the expandable support device through the working channel until the expandable support device passes out of a second end of the working channel.

21. The method of claim 20, further comprising:
positioning the expandable support device into the collapsed configuration prior to inserting the expandable support device into the working channel.

* * * * *